(12) United States Patent
Kohwi-Shigematsu et al.

(10) Patent No.: US 10,364,470 B2
(45) Date of Patent: Jul. 30, 2019

(54) LONG NON-CODING RNA EXPRESSED IN AGGRESSIVE CANCER

(71) Applicant: The Regents of the University of California, Oakland, CA (US)

(72) Inventors: Terumi Kohwi-Shigematsu, El Cerrito, CA (US); Yoshinori Kohwi, El Cerrito, CA (US); Ellen C. Ordinario, Oakland, CA (US); Michael A. Balamotis, Fremont, CA (US); Hye-Jung Han, Lafayette, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/353,710

(22) Filed: Nov. 16, 2016

(65) Prior Publication Data

US 2017/0067125 A1    Mar. 9, 2017

Related U.S. Application Data

(63) Continuation of application No. PCT/US2015/031431, filed on May 18, 2015.

(60) Provisional application No. 61/994,732, filed on May 16, 2014, provisional application No. 62/002,125, filed on May 22, 2014.

(51) Int. Cl.
*C12Q 1/68*    (2018.01)
*C12Q 1/6886*    (2018.01)

(52) U.S. Cl.
CPC ........ *C12Q 1/6886* (2013.01); *C12N 2310/20* (2017.05); *C12Q 2600/158* (2013.01); *C12Q 2600/178* (2013.01)

(58) Field of Classification Search
None
See application file for complete search history.

(56) References Cited

U.S. PATENT DOCUMENTS

| 5,990,299 A | * | 11/1999 | Ruzdijic | C12N 15/1138 |
| | | | | 536/23.1 |
| 7,745,391 B2 | * | 6/2010 | Mintz | G16B 40/00 |
| | | | | 514/19.3 |
| 2003/0082742 A1 | | 5/2003 | Astolfi et al. | |
| 2003/0198961 A1 | | 10/2003 | Spelsberg et al. | |
| 2004/0038240 A1 | | 2/2004 | Sinha et al. | |
| 2004/0053962 A1 | | 3/2004 | Adrian | |

FOREIGN PATENT DOCUMENTS

| EP | 2 524 968 A1 | 11/2012 |
| EP | 2524968 A1 * | 11/2012 |
| WO | 2007/075206 A2 | 7/2007 |
| WO | 2012/122101 A1 | 9/2012 |

OTHER PUBLICATIONS

Liu et al Clinical Immunology. 2004. 112: 225-230.*
Coleman, R. Drug Discovery Today. 2003. 8: 233-235.*
International Search Report and Written Opinion from PCT/US2015/031431 dated Mar. 2, 2016, 11 pages.

* cited by examiner

*Primary Examiner* — Carla J Myers
(74) *Attorney, Agent, or Firm* — Kilpatrick Townsend & Stockton LLP

(57) ABSTRACT

The invention described in the application relates to a long non-coding RNA expressed in cancer. The invention thus provides methods and compositions for evaluating levels of the long non-coding RNA to assess the aggressiveness of a cancer and for modulating levels of the long non-coding RNA.

13 Claims, 9 Drawing Sheets

Specification includes a Sequence Listing.

Knockdown of *SAILOR* by shRNA reduces the growth rate of agressive BT549 cells in culture (assayed in sub-confluent cell density conditions)

| P value by two-tailed t-test for: | |
|---|---|
| Day 2 control vs. #3 | 0.4101 |
| Day 3 control vs. #3 | 0.0033 |
| Day 4 control vs. #3 | 0.0009 |

Figure 8
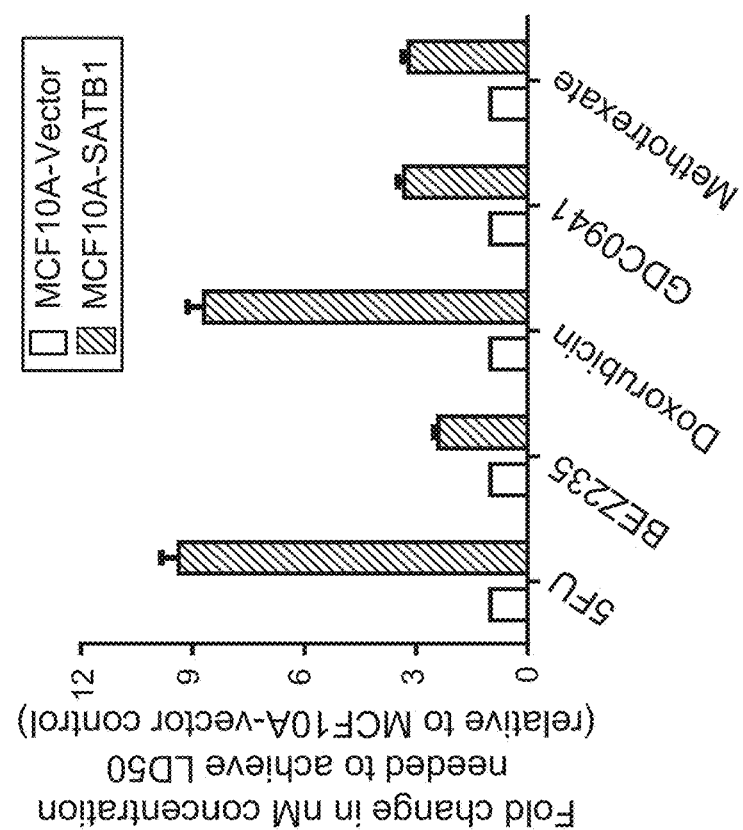
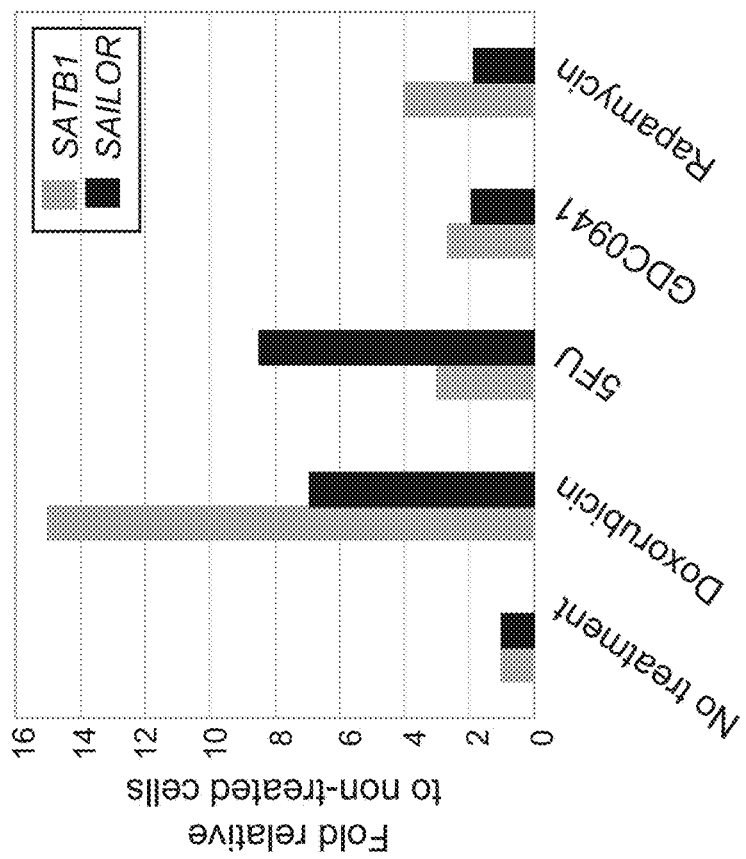

SEQUENCE LISTING

<160> NUMBER OF SEQ ID NOS: 15

<210> SEQ ID NO 1
<211> LENGTH: 1944
<212> TYPE: DNA
<213> ORGANISM: Homo sapiens

<400> SEQUENCE: 1 cgtttccccca gtaagcacgt ggcactcccc ggacctgcca cctgcctgct tcgtccttct    60
cgtcgtggtt tcccaaaccc cggttctgcc ggcccgggag ccttagcact ggagcaatag   120
gaaaaggcca ccgcgctcgg gtctgacag caggaggaa acacggtgtg gactgcgagg   180
ctgcacctgt gatgtcccgg ccctgctaa gaggacggcc ctttcttctg cctcttgccc   240
aactccaaac ccacattcac gccagcagcc tctccaggac cggcctcgct acagccagcg   300
agggctcgaa atgaggagtg ccgcggcttt caaactccgg gctccaactt gagcgccccg   360
gcgcccgagt agctcccggg atgcagaagt tgccacaaac ttcccaggcc cctcttcgcc   420
gatgcttaca atcagccgcg caggcaggga gcggaggag cggagatgg accggaaag   480 gatgctgagc agactcgcga tccggtgggg gaacattacc actcccgcag cccactcctc   540
caggcacctt actgccgcc cggctccaga acgcaccgag aggctcccct tttcccatt   600 tgcttccttc ggtctttcc actccccttt cctttctaa aaggggccat accggtgacc   660

```
tgaaggagtt tgttcagcca gggtctattg ggcaggtgtg gtggtgtgtc cacacccaga    720
cagaaaacga atggcatctt caaatccccc atcccgaccg ctctccccta ctctaccagc    780 ccaccccctcc aaggtccgtc tgcgtgagaa aaggggctcg aagaccgtt gaagccctgc    840 gcccacgaga ggggagccca gccgcccccaa taggggacga ggagtgggtg ctacggagaa    900
gtttggattg attccggaaa aagagggaca gagataaaac agcaagagta gcaaggggaa    960
aagggaggca aaagagcaga actcactcag gcatggacgt tgggggcggc ggtggctgtc   1020
gagtgcgggc ctgaaaccaa gaacggctcc ccgggcgggc gcgccggcgt cggacttccg   1080
aggcggcggc ttctgcctct cctgccgccg ccgccgccgc cggagctgcg gctgccgcgg   1140
aagttaattg caacttgact tcaagttgtc ctctttcccc atacgaagtg ggcgtttaaa   1200
ggggagagcg aggcgaggag cgagcgagcg agcgcgcggg gccaagggaa ggaagagaag   1260
gagggggagg gaggagatgt taacgggcgg gggggggaga aggggagggg ggcggcggcg   1320
ggggcgggag ggggaagggg ccggcgggag ctgctctcgt ctcgtcggtc gcggcgcctg   1380
cagtctggag gcgcaccgga gcggccgggg cgtccccgc gggagcccgc agccacccgg    1440
gacgcgcatc cagacgtggc gcttcggacc gggcacgctg cgcccggggg ctcggcggac   1500
cccgcgtagc cgccgcttcg gagcttgtgc ggcgcgggct ggccagcggg gcggccaggg   1560
cccgccccgc ctccccagcg cccgcccggc ttctcccccct ggcggtggga gcctcggcgg   1620
ccgctggcga cactaggcgc actgaagccc gagccgagcc gagcccgagc cgccgccgcc   1680
gccgccgctg ctgcgcaccg ctcccgggct ccctcccagc gcgccggccg gggtgtgggg   1740
ggcggcgggc cggaggggcg agggcgggcc agggggcgca cacggggggtt ggcgcggaag   1800 acaggaccct cagcctcgag gggtaagtgt gggcgcttgg gggtgcgctt ggggtgcgcg   1860
gcgcggttct cgtcgcccgc caaccctgcc ccctcacctc tccgggggcc cccaacacgc   1920
gcactcctcc tcttgtcgcc tgcg                                          1944
```

<210> SEQ ID NO 2
<211> LENGTH: 843
<212> TYPE: DNA
<213> ORGANISM: Homo sapiens

<400> SEQUENCE: 2

```
gcggccgctg gcgacactag gcgcactgaa gcccgagccg agccgagccc gagccgccgc     60
cgccgccgcc gctgctgcgc accgctcccg ggctccctcc cagcgcgccg gccggggtgt    120 gggggggcggc gggccggagg ggcgagggcg ggccaggggg cgcacacggg ggttggcgcg    180
gaagacagga ccctcagcct cgagggagcc cctaggtgac caggcaaaat ggcagttcct    240
tccagctggt cctcagatgg gcacatctat tagcctctgc tcttgtaaga agttagctgc    300
agaacccaca tgtgaatcct tgtaggactc tggagaagat caaatgggag cttagatgtg    360
gaagctcttt ggaaaccaag aaacactctg aaaatgaaaa gggtggaaga gtaaactgtt    420
cctgtttctc catcttgaca ggaagcagaa gttctcctta gctgattttt cttcttgcct    480
tatactgggt tctttaacac cagaacaaaa ataaataaat aaaagaatct tccagaaatt    540
catgaagaga cttcaggtca ggaaagcctg aactttctca tccaacaccc gttcaagtcg    600
gaggatgctg attaattcat gatggaaagg tatcaatttc acagcccaga cctctacatt    660
cttgaaatgc tcttctcatg ggagacatta aataagcttt gaattaactg agacctctgt    720
ggattctata actcaaagac ccaggctgac ggctggtgga atagctacca tctcaaacat    780
```

```
ggcgtgatgc tgcatcagag agaaaaataa gctcttgcat tgacaatgaa atgtctaccc    840
tgt                                                                 843
```

```
<210> SEQ ID NO 3
<211> LENGTH: 737
<212> TYPE: DNA
<213> ORGANISM: Artificial Sequence
<220> FEATURE:
<223> OTHER INFORMATION: synthetic DNA construct
<220> FEATURE:
<221> NAME/KEY: misc_feature
<222> LOCATION: (615)..(635)
<223> OTHER INFORMATION: shRNA target sequence

<400> SEQUENCE: 3
gccggggcgt cccccgcggg agcccgcagc cacccgggac gcgcatccag acgtggcgct     60
tcggaccggg cacgctgcgc ccgggggctc ggcggacccc gcgtagccgc cgcttcggag    120
cttgtgcggc gcgggctggc cagcggggcg gccagggccc ggcccgcctc cccagcgccc    180
gcccggcttc tcccctggc ggtgggagcc tcggcggcc ctggcgacac taggcgcact     240
gaagcccgag ccgagccgag ccgagccgc cgccgccgcc gccgctgctg cgcaccgctc    300
ccgggctccc tcccagcgcg ccggccgggg tgtgggggc ggcgggccgg aggggcgagg    360
gcgggccagg gggcgcacac gggggttggc gcggaagaca ggaccctcag cctcgaggga    420 gccctaggt gaccaggcaa atggcagtt ccttccagct ggtcctcaga tgggcacatc     480
tattagcctc tgctcttgta agaagttagc tgcagaaccc acatgtgaat ccttgtagga    540
ctctggagaa gatcaaatgg gagcttagat gtggaagctc tttggaaacc aagaaacact    600
ctgaaaatga aagggtgga agagtaaact gttcctgttt ctccatcttg acaggaagca    660
gaagttctcc ttagctgatt tttcttcttg ccttatactg ggttctttaa caccagaaca    720
aaaataaata aataaaa                                                  737
```

```
<210> SEQ ID NO 4
<211> LENGTH: 84878
<212> TYPE: DNA
<213> ORGANISM: Homo sapiens

<400> SEQUENCE: 4
gcggccgctg gcgacactag gcgcactgaa gcccgagccg agccgagccc gagccgccgc     60
cgccgccgcc gctgctgcgc accgctcccg ggctccctcc cagcgcgccg gccggggtgt    120 gggggcggc gggccggagg ggcgagggcg gccagggggg cgcacacggg ggttggcgcg    180
gaagacagga ccctcagcct cgaggggtaa gtgtgggcgc ttgggggtgc gcttggggtg    240 cgcgcgcgg ttctcgtcgc ccgccaaccc tgccccctca cctctccggg ggcccccaac    300
acgcgcactc ctcctcttgt cgcctgcggc ttcctcttgt tgcttgttgt ttggctgggt    360 tttgggggt gagtagaggg ggttactgta gtgtgtgtgc aggcggagga ggaagtcagg    420
tgagaggccg cgaagcaccc ccaccccaac ccagcctgcg tggggtgtat gcttcccac    480 tagggcatt tgggccattt tttttttctc cgtcaatgtt cggtcgagac gatgtttcct    540
agagggcctc cttcacttac agtctggtct gtccatctcc cttcatccca ccctcgtccg    600
tcttagcccc ttgtccagga gccctgcacc ccaagtgagg agcacgtggc ggaaggagga    660
ggaggccctc tcttgaagac ccccacgctg tgacccagcc cattagttta aatatttatc    720
ctcacatcac cagctgtact tttcaaccca ctggaacaag acgcctaggc aaggtccaat    780
ttccccaaaa agctgggggc aaagcgggag agatgagggt tttattgaca ttgggagaga    840
```

```
aggggccaag gaaccttccc aagtggagac tgaaactcaa aaaatctcta caaaaagact    900
agggtgactg gaggctcagg actgcaggct taggagaaac tggagctcca tcaactttat    960
ttctctcccc ctgcctctcc tcccccagc tctgaggaag ctaacaggtc ttttgttttg    1020
tattgtgtag cctttgggaa atttgcattg agtatgtcaa cagaaaatta ctactgttta    1080
ctcaaaggga ttgcagaaag ataaaacata gtaacatagt ttttactttt cctcttcttt    1140
gtacgcttgt gtgtatttgg caagaagtgt agttaggttc atggcatgaa ctgcaaaacg    1200
tcaggttgta acaataagga ctgtagagct gcctaggtgt attttttagaa gccgcacttt    1260
cttgaattcc tttcacacaa ggcttgctct ctcattaagt ccccataaat aattttattt    1320
agagaggagg aaactatgga agcaggaggg agattgctaa gatttccatc ctgccagcgc    1380
acagcactgt tgcagggaa gttcctggaa agtgattgtg ggctgagaat tcagtttttc    1440
ctaaaagctc tgttaggtcc tgttgtgtca gatggctatg aataaagcac gctgggaaaa    1500
tcctgatatc cgtgcagtct tattttatct tttacacagt ggttgattcg actttcaagc    1560
cctggtgaca aacacatcaa ctctgctgta ttttttgtgtg cttttttctaa ataaaggaga    1620
atacagcatg tattcatgct gcttttttcc cctcatccat ggttattgaa ttcactggaa    1680
gttattcatc ttttttcagt tgatcatcat tttatgccga gaccacaatt ccaaacatat    1740
aggaatttt taaaattatg aattagggtt cttttaggga accaaccctc ctttttaaag    1800
atacaagtgc ccaccacaac tcctagtttt gtaaagcaaa gcaaaaggt ataaatgatt    1860
ataatgagca aaacatagta aaacgttttc cttcttggat cactttctgt ccccacaggt    1920
cccaggagac attaaatcct cctgccttaa tttaccaaaa tgctgcattt cctaaccagt    1980
aacaatatct gtgtctgaga aagacatcag gtttggaatg gaaaaaaata cattctcggt    2040
atttaattac tgcttaacag taatttattg tagcaggcag ttgattttcc aattctgaaa    2100
gcctgaaatg aagctgaaca gaaatttgaa attttttaaaa aaggtttttt tttctttctt    2160
acactcttat atactcatct gcttccccaa gttatcagcc aagcccctat aactgaaagt    2220
atgatatgct cctctgagtt gaaccgagac cattttgccc ctcatttttt gaatttgctt    2280
tttcctccca atagtcttgt atagaaagca catgggctct gttagaatac agaattatgc    2340
aattctgggt gcagtgcatt aaatgacata gtttgataaa ctcttaagcc ttacagctca    2400
gatgttaata aaatattgta gttggccaca aatttcatag cacaaggcta agatcatttt    2460
tcagaagaaa ggggcattta atctggatta tttggttagt tgctatggtc tgaatgttag    2520
tgttccccca atattggggt tcatgtgtta gaacctaata tcaaagtga tggtattaag    2580
aagtagggcc tttgggaagt gattaagtca tgaaggcttc aaccctcatg agtgacagga    2640
gtgcctttgt aagacaggct gaatctagct accttgcccc ttccactgtg tgaggacaca    2700
gcaacaaaag tgccatctgt gaagcaagga gtgagccttc accagatact gaatctgctg    2760
gtgctgtaat cttggactcc tcagcttcca gaactgtgag caataaattt ctgttgctta    2820
taaattaccc agtcaaagat aatttgttgt agcacctcaa atgaactaac acaataatac    2880
atttgtgcta ctagattttt ttaacaagtc caaatgtgac ttaaatgact gaaagacaaa    2940
tctggaacat atcaaatggc caataatagt agctggtatc aaaagctgca ctggttattt    3000
ccttaaaaga atagacaata aaatattgcc tactaaatat tagaagaaag atcaagggaa    3060
aggataaaac agcattggcc ttgaaggaag ttatttgctg gaaaaagac atcaaaatgt    3120
gaaaagacaa tggatcagtt agtggtttga atcaaagaaa tacttgagga agaaaaaata    3180
```

```
tatatatata tgtacatatt tttctcttaa gaccagagga atcagagatc ctaaagctct    3240
aggttggaag gtattttaa agttaattg ttctgtcaaa tctttagagg ccattcaatg     3300
cagatatttt gggtgtgaag gggaacttac tacttaccgc cattaaggca aggattttta    3360
cctataccgt acttaccaga gaatagagtt cactatatat tgtgcaagtg aatggataat    3420
ttcaaaagta tttcatcttt atatacttta ttatgttttt accttatata tattttttta    3480
ccttatattg cacagaatta gtcttcctga aacttccaac cgttagtctt cgtcctgcca    3540
gttgcagcca aacagaacaa atttgtttat cagtcaagat aggcaatgtg ctggagtaac    3600
aattccaatt ttttagtggc ctgtaacagc aaacgttttc ttggttatgg tttgaatcca    3660
ttgcagttca gctggtctgt tccatgtctg tcactccagg tccctggcta atggaacagt    3720
tgccatcttg aatgtttcat gttgttatgg caaaaataaa gatcactctg agggtttca    3780
tgcagacatt taaatgctat ggcccagaaa tgccatacat catatggcct cacaaagaat    3840
taaccaggat tagttgtgtg gctccaaaga atcatgacaa gaaggtcgga tagtgcagcc    3900
tatcttgtac ccaacagtag agagctgtgg tacacaattc tgcagactac tgctactggt    3960
agtaatcctt gtccatatga taacctgcca gctaaacagt ctcttcctgt agctttatgg    4020
cccaagtctt ccatttttta gggcaaactg ccagagtagc caccagctta gagggaaaca    4080
ttgttatcag gggaacccgc ccccaatatt tcaacataga ttctttatat tttccctaag    4140
tgtcggccag tctgagcaat aaagagaaag aatacaaaga gaagaatttt acagctgggc    4200
cgctggggat gacatcacat atcagtagat ccgtgatgcc cacctgagct gcaaaacctg    4260
caagttttta ttagggattt caaaagggga aggtgtgtat gaacagggag taggtcacaa    4320
agatcacctg cttcaaaggg caaaaggcag agcaaagatc acatgcttct gaggaaacag    4380
gaccagagca aaatcagaaa ctcctgataa gggtctatat tcagcggtgc acgtattgtc    4440
ttgataaaca tcttaacaga aaacagggtt cgagagcaga gaaccggtct gacctcaaat    4500
ttaccagggc tggtgtttcc caatcctagt aagcctgagg gtactgcagg agaccagggc    4560
atatctcagt ccttatctca accacatagg acagacactc ccggagtggc catttgtaga    4620
cctcccccca ggaatgcaat tcttttccta gggtcttaat attatattcc ttgctaggaa    4680
aagaatttag cgatatctct cctacttgca catctgttta taggctctct gcaagaagaa    4740
aaatatggct ctttttccc aaccccacag gcagtcagac cttacagttg tcttcccttg    4800
ttccctgaaa attgctgtta ctccgttctt tttcaaggtg cagtgatttc acattgttca    4860
agcacacatg ttttacaatc aatttgtaca gtttaacaca atagtggtcc tgaggtgatg    4920
tacattctca gcttacgaag ataacaggat taagagatta aagacaggca taagaagtta    4980
taaaagtatt aattttggga actgataaat gtccatgaaa tcttcacaat ttatgttcag    5040
agattgcagt aaagacaggt gtaagaaatt ataaaactat taattttggg aactgatatg    5100
tgtccatatt aaagtgaaat cttcacaatt tatgttcctc tgctgtgact ccagccagtc    5160
cctctgtttg gggtccctga cttcctgcaa cacattgtgt gacttctttt actctctact    5220
gtctctttga atgcaacact acaacctcct gtacccttag aaccccctaac aaagtgtggc    5280
ctcttatcaa ttttatgtca ctcttttata tttactaata ttatatacat tgtatttct    5340
caggacttat tttcctggca agggtataat aaacaggcat ttttaacaac tgttttctga    5400
aaatgtcatg gtcattatca aaatttgaaa tttggtctga gtagctactt cccttgttgt    5460
gaacatcaaa tgtgttatat gatttgtaa cacaaatttt aaaaatcctt cattcattca    5520
tttatcctac ttttgttcat tcaataaata ttcattttct acctagtaga aggcaggcac    5580
```

```
tcttttaagg attggggata tggagatgat taagagttct cctcttcaag aaacacattt    5640
tctgattggg cagacagaat taaaagtcat tataatgcta atagaagcac aaagtgttat    5700
gtgaacattt agaaagaagc aaatagctag ctggcaggat ttagaaaagt tccatagagg    5760
aattgacact taaactaagt cttgaggata agtgagactc ctccaggcag aaagaggagg    5820
gagagagggg atatttcaac caaggagacc agcatggaca aaggcactga acatgacaaa    5880
gcttattgtt tatggaactg taaggaattc agtgaggctg gcgcatgggg tctttgtaaa    5940
ggctgaaaat tctgaagggc cttgcagaca ttctctggag tttggacatt atcccataca    6000
tcaggaactg caaactctta tgtctacctt gggccatgca tggatgtaca tgactaaagc    6060
agaccaagtt aagactataa gcagtcgtgg ggctgtggca atgtgaagaa tatatcctct    6120
gtccaaatgg gatagtaaat gccattggtg cctccattct ccaaagaaaa gcaggaaatt    6180
tagatgtata tgaaaaattg aatattaaat gttgtcaact tatccatatt ttgaagtaca    6240
ctgttagtcc ttaagctaat tttgacctac agacaaattt tgtatagctt ttgcatgtat    6300
atttctactg aaggtcaaag tgtttatacc cattggagaa tagtagccac tctttatctg    6360
caagttatat gttccaagat ccccagtgga tacctgaaac tgtggatagt actgaactgt    6420
atgtatactg ttttgtccta tacatgcata cctgtgatga agtttaattt ataaattagg    6480
caaagtaaga tattactaac aatagctaat aataaaattg aatagttatg atacactgta    6540
ataaaagaga ctatgatctc tctctttcaa agttatctta ttacactgta ctcacctatt    6600
ttcagactgc aattgacctc aggtaactga aactccagaa gagaaacctc aaataaagga    6660
agactattgc ctgtttatc tcaacctatc ccatagccat gtgcctaagg actgtcttga    6720
ggatatttaa tttttgtcat ttttttaatt gagtccacta attacttact cttcctagct    6780
gctctcttgc tttcatgcca gacttgctgc cactcaatag tcagaaatat gcagcaacac    6840
cccacacttt cctatagcaa ttataatgtt agaaatacta ggtatccttt cataacgcat    6900
gctgaccatt ttcttgtaga tttggtccca tgggtacatc cagattctta aagtcattca    6960
attcactggg ccatcaggtc tttaagttct tgacaacttg gctgtacaga ttacaaattt    7020
tattcgatct tcttgactga agaaagtca acgttcctgg gttgttttgt ctaacttata    7080
aacaataaca atcatccatt ttatgtgttc tgtgagtttt gaatatgaag gggcagcatg    7140
agcaaattat attttatgtg aactttgaag taaataaata tatctaggca aagccacttt    7200
aggtgtccaa ctgtctggat tctaatcctg gttcaattag ttgctaccta tatgacctag    7260
agcaaatctc ctaatttctt tatgcctcaa tttcctcatc catgttacag ggatgctaat    7320
agttagtaga tggggttagt aggtgcagag tgcttcagaa tagaaaaatg aatttactag    7380
gatgtaagtg ggatataagt acttaactcc tggatgacat gatgttgtgc tgggggtaca    7440
caagccaaag aagaattatg gcttctattt ctggaatatt tatttttttac ttgaggattt    7500 tagaaattat tttcttatga aaacagtgac acatataatg gaattaactg tagcattttg    7560
catgaatttt aaagaaaaac aagagtcttt aaagatcttt cagctgcttc ggattttggg    7620
gggaagaatg ggaactgcat tttcttcctt ttgctgcact ctctccttta tcaggttggt    7680
ggaaatgctt atgattagca gaccatatac actagttaca ttagttacat ttgcctcaaa    7740
actgtgaaag tacctcctgt atttatgtgc tatgaatgct gcccaagtgc agaatctttg    7800
ccatttaaat gttcagattt taaaccagaa atgtgttggg gtaaagaaga aaattattag    7860
agcatgacct tagggaaatc aagtcacaaa aaagaaaaga gctgaactga attctatttc    7920
```

```
ccattctgtt actaaccagc tggcttatta atgtccataa agagagagat ttttgtcctt    7980
ttcactgata atcctccaca ccttgaataa atagataatg ttgaatgatc ttgggaaaga    8040
cactttgtta aagtctcagt ttcctcagct gcaaaacaaa gatgtgatct taaacttaaa    8100
ctttattgtg tatggaatta aatagagttt ttgtttaaaa tgcaggttct ttgagtccat    8160
gcccagaaat tcagatttgg tagaaccaga tgctattcag caatccacat ggatttgggg    8220
cttgggttgt aaggagcaaa aatccaactt aaaagaaag gttttatttt ttattttgct     8280 tcatttttg tcccccctct cttcccctcc ccgcacataa attggaaaat acaatgcaag     8340
gactgcttaa ggcataatta gatctagctg ttcaaataat gtcaccaacc atcttttggt    8400
tatgctttct tctcttttaa ctttatactt agtctggttt ttcctttaag gagttcattt    8460
ttaagaactt cattcttaat ctgccttttc tcctagcttc cattcttctg acatagaaac    8520
cccagcacaa agagtattcc ttttttctcaa attttccagc taaagaaact cacccaact    8580 tgactgtatt agattatgtc aggtacccgt acctgcactc atcaccatgg tcagcacctg    8640
tgattcacac ctcagcagcc ttgagtcaaa tgcccacctt ggatttggga gtacagtcac    8700
tcaactcaaa ccatgtgggc ttggacgtga aggtgggatg ttctccaag acaaattgga     8760 attaattttt ttagaaataa ggaaatggg tgcttttag ccaaaactat agatctcctt      8820
ccactactga gcattttaa gacgtattta gagatgaatg atccaaaaat gttacaaaaa     8880
tataaccagt attccaagac attgaggcat tcagccctca atgtgacaaa gcaggggctg    8940
agaagtacct aagatggtca cagtcccagt gccaggtgcc tcacctattt acctcagtgt    9000
ttggggaaaa tattaagtat tttccacgtg ttattgtatt agttttcaca ctgccataaa    9060
aactacctga gactgggtaa tttataaaga acagaggttt aattgactca cagttccaca    9120
tggctggaga ggcctcagga aacttacagt catggcagaa ggcaaaggga aagcaagaca    9180
tgtcttacgt ggcagcacga gagagagaga gagagcaagc gaggaactgc catacacttt   9240
taaaccatca gatatcatca gatcttgaga cagcactagg gggatggtgc taaaccatta    9300
aaaccacccc catgatccag tcatctccca ccaggtccca cgttcaactt gtggggatta    9360
caatttgaca tgagatttgg gtggggacac agagcaaaac catatcagct atgaaggtga    9420
tctatgtgca ggtgaactgt gacttgtgct atgggaatca gtggattttg agaatcagtc    9480
aaaatcatta ttgttatgtt tgacatgaca ttttgaagtc atctcaggca tacaataata    9540
gtactactct aggatcttca tgcataaacc tggaagttgg ttgatgcaat tgaaaagaca    9600
aagccctagt acaaaaaaaa atgggacaaa gaaacaggca ggaccagcaa ttaaatcttg    9660
ctttgatttg gttatcagtt tgtgtttatt taataatctt ggacaaatgt attcatctaa    9720
tgaatacagc cccagcctgg atcccagcat gcctggttcc aattaatgtt tgaaacataa    9780
tggatacatg ctatacagat aatgaaaagg ggtaagcagg caacagtgtg aagacaaaa    9840 ctgagttgac ttagttatca gataggtctt aggtgtatta catgcgagtt catgaagta    9900 aattcggatg aatgaattat taacccctat ttttgttaag tgaagaagct gctatcattt    9960
ccttaagctc attaatacaa ttaataaaaa taaaatgtct acctcttcat tttagtatta   10020
agtcattagt ttagtttcag atgctttttcc atacccttgc cccactgtta ccttcaccaa   10080
agtaatccaa tgtgcagaga aaagtgtttt caacaaataa tgctggaata aatagatatc    10140
cacgtgggaa aacaaaacaa catttatcca tatcatacca tacacaaaat tcatttgcaa    10200
tggattatag atccaaatgt agaaggtaca agtataaagc ttttataggg aaacataatg    10260
taaattgtag atagacaaag atttcttaga tgagccatag aaaacaataa ccataaaata    10320
```

```
aaaaataggt aaattacatg ttaaaatgta aaacttagca taatggcatg tgcctgtagt    10380
cccagctacc caggaggctg aggcaggagg atccctttag ctcaggagtt caagtcaagc    10440
cggggcatca tagcaagact gcatttctat gattaattaa ttaaaaagtt atgtttaaag    10500
aaaagcagag tgaggagtga tatctggaaa ttccttatta aacaaacatt actactagaa    10560
ggatttcctc tcttgtgcat ttagttcaag ttttttgttt gttttgtttt gttgtttttg    10620
agacagggc tccactctat cacccaggct gcagtgcagt gatagaagct gactctgtga     10680
gcttaagcaa agcacatggg ggatttttcat gcaatccaaa atcagggatg caatggagcc   10740
ttaagaatag aagaactggc tcggcacagt ggctcacgcc tgtaatccca gcactttggg    10800
aggccgaggt gggcggatca tgaggccagg agattgagac catcctggcc aacatggtga    10860
aaacctgtct ctactaaaaa tacaaaaatc agctgggcgt ggtggcacac acctgtagtc    10920
ccagctactt gggaggctgg ggcaggagaa tcacttgaac ctgggaggcg gaggttgcag    10980
taagccaaga ttgcaccact gcactccagc ctgggtgaga gagagagact ctgtctcaaa    11040
aaaaaaaaaa aaaaaaaaa gaatagaaga actattgaag tgctataggg aaccaagtca     11100
attctttctc tccatatctc atctttgtct ttcttcctca gagtagtcca gctccctgcc    11160
tcctcagttc acacagtgaa tcatggtttc taattgttct tgagccattt tcagtcagtc    11220
caccctgaga aaggaccatc ttcctgtctt tcacaattct cagggaagag tctgattggc    11280
ctgcttgggt ccagtgacca cccttattcc aataagctgt gaccagaggc aggatgatgt    11340
ttaaagaaac atagcatttt ctttcatctc ttgtaatgtg gagtgaaaag aaattgcatc    11400
acagttgaga tccactgtac atttactctt cattagacat gagacagagt tcacaaaaat    11460
tttgcatttg gtcacagttt ttaatggcaa caattattgt tgtgttggtt ttttactttt    11520
ttgattatct aatatcggca tctcctctct gcatatctat gtattgacta atacatatta    11580
agggccataa acaaagatgg ttcattttag aaatgggcac atttgtttat aaattattag    11640
ccaagatcta ttcaaatcca gacatgattt gttctagtct ggatatacaa taaaattaat    11700
ttaataatt ttaatcaact tcaaaaacag caaattccaa gacaattagg ataacttaa      11760
gaactcatat ttattgagtt aacagatggt aaattaaaaa acaatgaagc taattttaa     11820
aatcattcat tgaattaaaa aatagactta tttaacaaaa ctgtttttaa gctgcttttt    11880
tatcctaata tgcatgtttt aagattccaa tttgggggac tctagaaaga cgcagagtga    11940
gtttcagtat atgaacactc ttctactgag ttacttttta aaagcttcag aatcatctga    12000
aaaaaaaact atcaacaata aaaatataag aaataagaat atttcagtta ttggaaggga    12060
tggagggttt gcttcttcaa ttccagtttg cttgctaaca tggtcctatg gtgtattagt    12120
ttgttttcac actgctgatg aagacatacc tgagactggg caatttacaa agaaagagg     12180
tttaattgaa cttacagttc catgtggcta gggaagcctc acgattatgg tagaaggcaa    12240
ggaagagcaa gtcatgtctt gcatggatgg cagcaggcaa agagagagaa cttgtgcagg    12300
ggaactcctc ttttttgtga gacttattca ctatcaggag aacagcatgg gaaagacttg    12360
ccccagtgat tcaattccct cctaccaggt tcctcccaca acatgtgaaa attcaagatg    12420
agatttgggg ggagacacag ccaaacccta tcatatggtc ttctgtattt ctgacccttga   12480
aatatcttga gagtttcctc tgctaacaga gtgaaagttg ctcctggcca gaactttatt    12540
tctgcatttt aatggacaaa cataaaaaac ttcccatctg atggcttctt gagcctagtg    12600
catgggtgac ttgaaatatg ctagcaccac acagatattt tttctttgat cttttctgtt    12660
```

```
ttctcctttg ttttctagtt gtaagtgcca gaagctgact gtgagcttat aggaaaagga    12720
gaatttcatg gaagcacact gaaagcatgg gttcttttcc ttttgggttc tcacttggtg    12780
gggtctcctt gcagcttttg gaggtggggc aattaacatc ccccagtaca tgaagtgtac    12840
cagaaactgt ggttgttttc aaatgagagt tcaatcactt ctacttcctg aggattttat    12900
agatgaagtt ggagataaca ccattgatac attaggatac atcatttgca ttttaccagc    12960
tattattagt tttaacatga tggcatattt agaactagag ttatccatgt agaaatgaag    13020
ttgttccata aaaaaaatgg gaatacattt gtttgaatgg ctagttgctc aattactgtt    13080
atagtcttta ccatgggcag tcacaaactg ttgcaattta ttttatggtc ctggaaactt    13140
cttgtctaag atctgatctt attttacgtt gtaggtattc cattacttga tcaataatgt    13200
ttagaattgt atatatttgt ttttgtagac caattcatta gttgtaattt gagttagaaa    13260
acatttagag atatagaaac acatttattg ttgagattgt agtaaaaatt attttattgt    13320
tatgcatttg aaactctttg gcccctagcc ccctttcctc tggaaataat tgtttttata    13380
ataccaattt gataatatga atgttcttag gaatgtaatt ataacagtat agtaggagag    13440
actatattgt ttttaattaa caagaacag gtgaaaataa aatagatca tgaccaaatg    13500 aaaaaatgta ctagagagat gtaacttctg ttttgcagaa atagaaatca aagatataga    13560
ggaaaaactt cataacttca taaacatcca aggaaattaa taagagttaa atggataaga    13620
ggtaattaga tgacaaatta tggagctcta atttagaatg taagctactt aatggcaata    13680
aacatcttgt tgttacccaa cccctaagac atagcttaac atatagcata gcttaacata    13740
tagtatatac tattattgtt aaataaacat tattttcttg aatttataaa taaaataatg    13800
agtgttttaa aaatagagca gatggatcag aagtaaaaac ttgttataat gttataataa    13860 aataaaacatt tccatatgta acaactacac tgacattgta ggatttcttt tgagcaaaat    13920
taaggaatgc aaggcataag taaataaatt tttaaatttc tgggacgaag aaaatttctt    13980
aaagtacatg tgaaggaaaa acatacacgc ttttgtagat tgccttcatc tttcttatat    14040
agaacaagaa cttttttaaag aacacaggta aatgtccaca taattttaag agaaacaagt    14100
ttgaagtata ctagaaactc tggttgtttc cgtatgagag ttcaatcact tctacttcct    14160
gatattttac aaatgcaatt ggagataaca ccaatgatgc actaagctac aacatttgca    14220
ttgtaccagc tagtattagt tttaacacga tggtatattt ggaactacag ctatttatgt    14280
agaaatggtg ttgttctata aaacgttttta tgcctaccca attatcagct tatacataaa    14340
agcaacagaa taacaaaatc ttccaggtat cagagaacat aacaaccgaa tgtcttttcc    14400
ttaaaaattg caggaaatat tgtccagatc actgagaggt gaggtagtat aaaaactcaa    14460
gaataagaaa ttccaataaa aaagattaat actaagcatt gaaggcaaag acaaaataag    14520
tgaaatatag tgaaatcaaa gtgaattggg aattgatgct gatagctaga tatttttttac    14580 taagggagca atgttttcaa taaaataatc ctggagggtt ttacattttt aaataaagca    14640 tctatacccta gtgatcacaa tatggaaaga ggacaggaag gaaataaaag cattataaga    14700
agcagcattt ttgctttatt ttcaagtcat taaataagaa tgcatataaa agtatagttg    14760
tagacaattt aatgtcggca ctagtagaat tgaaagcagg atatctattt tctaaataat    14820
tatcaaagat aaaaaagcaa acatagtcca ttcaaaagac aaaatgaaag gcaacaacaa    14880
ggaattattg aagagaagaa agtttaagtc caatcaagct taaaaaatat gacaagtata    14940
aatggcttaa attttcctat tcaaatggaa agatccttat attaaattaa aatcaaagtc    15000
taatggtttg gtggtgctta aaaaagtcat acgtaaagga aaagaacaca gaattatttt    15060
```

```
ttaatggcaa agttttttcc agcctaacat gttcacatcc aaatcaaaaa tacaatatga   15120
atatcaaaca gggcagaatt tttggcagaa aaactccaaa acagtaatca tgacaaaagg   15180
gactatttta tacttgttaa taatgtcgtt ctactgaagg aataatagta ctgaaagagt   15240
atgcattaaa taactacaaa taaaaaataa tttatacatt ctgttttaaa aatacagtat   15300
tacttaccac agcaaaataa tatatataca agcagtacaa aagtttacaa atttaggagc   15360
tatacaagtg aaatactttg tatcagtagg ttaaataaga aataaattat taatttaata   15420
cattttttga aagcagaaga gaaaatttac tatctgttcc tgaaaaaatg ttgaaaatag   15480
aataaaatat tttatcttaa ttattaatat caaaattaat taagaattct aaaaatgtac   15540
atatttaaaa caggatggga tgaaagttgc tataatggtt ttgccataat aatatcattt   15600
aatagtattt ttaaaactct gatcaatgta ataaaacata ccaaggaaag aaaagctata   15660
tagaatgaaa aaagagatac aacattatgt attgaaaaaa tatttttata gtttaaaaac   15720
ccaaagtagt caatgaaaac ctaaataaaa ataattggta aaatattaaa acatataaac   15780
attaacataa atcagcagta taaatgtaag caatcattaa ctcaaacata aactttaaaa   15840
agagagaact ataaaaaaca aattcacaga ctggtttcaa gtgtgaacga taacattttt   15900
atattgttat ttcccaagtt taatggaaat gtaataacaa tctccctttc atttttact   15960
ttttgaggta gtggtgagag gaatttgatt ttagtgtaaa tctagaagaa aaagtagtca   16020
agaatagcaa agttcaattt ttagaaagaa ggagtgacta gtcttatcaa atattaaaat   16080
atataataaa gttataataa ttaaaactat actggcacca aaataaatat attaatgagg   16140
caaaacatgt gggcaaataa attatatata aaatgaaat atttgataat ggctggacca   16200
cagattaaag gagagggaaa atgttttgca atatatgggc taatggaaaa aaaaaatcag   16260
cttttacact cattatgtac ataaaataca ttatgcaaac taaaaccttta ggaagtctaa   16320
cgagacttta ttttataggc ttaaaacatt gtaacaaaat tgcaaagtga acagtaaaat   16380
agatttgatt atattaaaca cttgattagt taaaacaaca atgtaacaag caaagggtgg   16440
cctatgtgca attgcaatta tttgaacata ataacaaaga gttgatatga tttcacaaga   16500
gctcatacaa actcatactt aatcaatata tgagataaga atgaaatcac atttcataaa   16560
atatgaaata taacacattt gcaagcacat aaaaatccag ccttaataac aatcaaatga   16620
atatacacta aaacaaaaaa aaatgagtta tgtttaggtt taatcaacta tttaaaattg   16680
atgtcaagga cttacacttt cagctgttac atttagatca gctcatccta taaggacaag   16740
tagaacaaat agaaaagttg aataaaatct accaaacgtt tgtttaaaag cactggagag   16800
ctccacagtg gagagagctt gagagcagag aatttaagaa agatcctaac tgcctgtcag   16860
aaactaaagt aaaacatcac ttaaagaaga gatgatcttc cagaggtcta aattatctct   16920
acaattttc atacacaatg tctggcattc aataaaatta ccaggcatac cagaagacaa   16980
gataaaatga ctgaaaacag agctagagga gatccagata taggagtaac aaattttaaa   17040
atatctatgc tatcttttaa aaattatatg agtagataga aaatttcaac agactactat   17100
taactgtgat aaagaatcaa atggaaattc cagaactgaa aaattaactg aaattaaaaa   17160
ctcaatagtt ggatataaga gcagattaga aattcttgaa gaacaaactt atgagcaata   17220
gaaattttga tgttaatacc taacaaagtc agaaaaggtg tattggaaaa tggtttctct   17280
catgtaactg gtgacatgta aacctatata ccactttttg gaaatacttt gataatgtga   17340
attcactatt tgaacaaaaa aatttatatc ttttaacccca gtaatcttat ctctgggaat   17400
```

```
gtgccatagg aaataagttt ttaaatccac agtgcctcat gtatgaagat attcactaca   17460
gacttatgat agtaataact atctacagac aatgtttaaa tactttattt caattaatgc   17520
aggttaatcc tcacaacaat ctatggtgct agtgaacatt actatcctca ttgtacagat   17580
gagaaaactg aaacattgag aagtcaagta acttgctcaa gattatatag ctagtgcata   17640 gagggcaaa gatttgaacc agattgcctg gttccacatg cactttaacc tgctttattt   17700
aggcttttga aagcaaccta aatagctaac attgactaaa taagtgcagt atacctggtc   17760
tgtgtgacat tttgcaggta ttaaaaagtg aacattctga acccttttag caatatggca   17820
aatacttctg atgtgatgta tgcatataaa tatgatcgaa agcaaatatc ccaaaaggtt   17880
gatggcagtt atgtcaggtt agtagcacaa tagtttcttt tctcattttc tcacattttt   17940
agtaatgtgt gttgcctata ttaaaaaaca aatattaaaa agtagtagca tgtattagat   18000
cagagcatgg gctcagactg cctgtgtcat ctcttattag atgtatgacc agggacaagt   18060
tattgacctt ttgtttctaa gtctctaagt ttatcctgta aaatgaagat aattgtagta   18120
actacctaat aacatgattg taaggattaa attatttaga acactatttg ttacttggaa   18180
aatatgcaat cataagctat tttgttgtta ttgttatttt actaccaaag cttattgttt   18240
cagagcccct aggtgaccag gcaaaatggc agttccttcc agctggtcct cagatgggca   18300
catctattag taagtttcat ttctgtattt ggatctttat tcatccttat tatgaattcc   18360
ccaatactga ggtttctagg aacctacctg ccattggctg aagggttgct tctgaattct   18420
ttcccagagg cagtgacaaa aatcaaacat ccgatgtgtt ctttacccttt cagtaagctc   18480 agcctccctg cttgtgtcac atctctaaac atacgtacat gcgtgattga aactgtctat   18540
tgaaagcaat attcattaa cattatcaat actgaattag agaaaatatc tatcaatgtc   18600
accaattcca cctgtctctt gatgtatgac tttttacctg acaggctaaa taacaataga   18660
aagttctttt taaaaaatag aagagttgct atgcagggac ttttttggaa ttaagtgccc   18720
cagagaacct agaaatgtgc tttaaaactt tttgtttcac ctggcagatc caaaaaaaat   18780
ttggaagctt ttggttgaat tccctcatta cttgaagttg ttttatgaaa attgaatata   18840
tatatctgtt aggttaccaa gacttatggt tagctatctt aatggctagt gatataagac   18900
cttgtaacaa accctaccaa tggaactgac aggatttac cagggaggat attgcagtac   18960
ctgtaagagg aagggataca aattggcact tcatacattt gtgagaacaa ttgcctttaa   19020
tgtgtctatt tggttttcat aatattgcag gcctctgctc ttgtaagaag ttagctgcag   19080
aacccacatg tgaatccttg taggtgagtc caccatttca ctaatactgt gttttaattg   19140
cctcagttac gtccatctga cattcattgg caaagtcctt tggttaaact tcctaataat   19200
tctcagctct atcatatggt aaatgtttaa cacattgctt taatgtttga gttttttcatt   19260 tttgttgaag ttattattcc tctcaggctt attcatgaag gcatttctgg atttatgcct   19320 ccctgaccc attccaggat ttaccccaaa ccttccacac tctcttctaa caggaaagtt   19380
ctgttatgac acaatagtac ttattaagac agatttacct tctaagtctc aggacagcat   19440
ttcacaacca gaaataaccg gtcacatgaa gaaccagagt ctggtagtag tgaaattcat   19500
tttccttctt gaaaagtgg atcaaaggat tcaaacagca agtggtgaat caatgaaaag   19560
tggtaaaatg gtgaggaaaa aatgttacta aaagatgacc tcaagattac tggtgcatat   19620
gaattgcttt tttatatagg aaaatactgg ataatttctt attgtcatag tataattaga   19680
agcaatttca tgtgttcatt ttgccacatg agtttaaatg gaatagattt ggttccctct   19740
ctaacatgag ttcagtgtct gaacttgggc aaatttctaa acaattctga gcttcactac   19800
```

-continued

```
ctctgcttga aagtgagaac aattgtattt atctattatt tgtctattag gttatgagag    19860
caaaaatgtc ataacataaa acacctggca cccagcaagc aattaatgct agtccttccc    19920
accctatttt atggaggtag aaagaaaaaa gataacagac agctctactt ttattttac     19980 atatatcctt cattgattac cttatgagta aacctaaaaa cagcaaaatt ctcatctctt    20040
catccttcat ttctcagtgc tttatcaaat ttctactatg aactaagaac tgagtgctat    20100
gggagacaca aaggagagtc aggtattgtt ctgttctcaa ggacattggc atctagaaag    20160
ggagattttt ttttaatgcc attagagaga caaaataaag cactgtcctg gttttaagca    20220
ggaaaaatca ttttaactgg ggttaccagg aaggtttca tggaataggt agtgtttggg     20280
ctttaaagaa tgggtatagt ttggaaagca agaagagagg aaatacaatg agtcatgact    20340
gaagcacagt tgacccttga acaacacaag tctgaactgt atgggtccac ttatagtgga    20400
ttcttgtcat ccaaaagtgg atcaaaaata tggtatttgc tggatgcaaa acccatgtat    20460
agggaggact gacttttctt ctatgcggat tcagcagggt ccacttgagt ataccaggat    20520
tttggtattc tgtggggtgt cctggaacca atcccctgcg catgccgagg ggagggacaa    20580
ctgtagtata attgagagaa aaaccattgt cccaggattg aaggacagg ttggcattac     20640 cttggatgaa ccacttctcc cctgtagcct tcaacttctt cacttgtgag agatgtagaa    20700
taatccctgc cctgttggtc tttcaggact ctggagaaga tcaaatggga gcttagatgt    20760
ggaagctctt tggaaaccaa gaaacactct gaaaatgaaa agggtatctt tttttccttt    20820
tctcccttta ccataaattt catgatggca cttaacagag ccagtcgttt tggtatttaa    20880
aaaatgtttg gtgaaataat tagttattgg ttgaatgaat gaatttataa gtgaatacat    20940
gaattaaaca aaggtatgga gtaggaaagc acataatatg agcagagaat aagggattct    21000
atttggaagc atgcactaga actggatgtt agggatgtga atgtggctag ctggaatggg    21060
tctgtggttc tcacaatgtg atctgttgac cagcagtgtc aataccacct gttaacttgt    21120
tagaaatgca aaaagaatta tgaatttgaa actcagggtg ggacccagca atctgtttct    21180
ctctaagtca ttctgatgca tagcaaagtt ttgagaacca tgactttgta ttaaggtggg    21240
gagtttggaa attattttc tgtaagttcg gtgctaatga agattttcaa ctgtgggtgg     21300
acataatcac agccgtattt ctaggatgat gaggcagaag gttgtaccta caatatctat    21360
gacttcagca ttaaaaggac aattagaagt actgaaaaac acaccgtatt tgccaagctc    21420
cagaaatgaa gattttgttt ttacctatttt ccgaataata tccccatact tacctaagag    21480
gcaaagcaga gcaagcattg ctcccaggca ctggggaaac ccacttggtc tgcagagccc    21540
aggcaggatg agaatgttta tgtgaaaaaa gtaaatgaga gcggactgtc aaatacggcc    21600
ccaacctttc tgcagagaga ggagtaagta agcctttagt cctgaccaac tgtggggaaa    21660
cattaaatgg aaccttccaa attggtttaa agtgggcagc taagcctatg ccaaggacta    21720
agccaactgc actggctaca aacacacctg tgtctttagg gctggtggat acaaatttgc    21780
caaaggagag cacactacat ggaggaaaaa tgaagagccg cagggaaaca tttatcctaa    21840 agggaaaga gtcaagacag agatatcatg ggtcagttgg gaaggagatg gaggggagag     21900
gcaggaggtg agctgttcag attgctagaa tgaccaatcc agatggctag gatgaccagt    21960
catcctggtt tgcccaagag tgagggatag cccacatcat aggatttcca ggacaatcct    22020
tgtcaaagcg ggacaattag tcaccttaag actctgccct ttcacctgtg ttcaagacct    22080
ggggagaagg cataataaaa atagaaaaaa tcactgctgt caacctccgc ttctcaaaat    22140
```

```
attgtccaga aactagcagc ataggcttca cctgggagct tgttagaaat gcagatactc   22200
aggcatccta gacctactga atcagaatct gcatattaac aagagctctg agtgatttgt   22260
atgcacatta gagtttgtct caaaagatct tgtggcatcc cacagtaaat aatggagcac   22320
aagtggcaga ataatttcc tctgggctgt aatatggcta atatccaggt tgatcagata    22380
ctaagctaaa accagatcaa ccttgcctgg gaaggacgca acctagggat ggagagcaac   22440
ccaggcagag agggagaaag aggctgacac aaattagcca agaggggacc ccctgaacta   22500
ttaatagtag tagtatttgt agggaaagtg agaaaagcca gcaagccagc aattgtatgg   22560
taagaataaa gctagagaaa ttaatgttgc cagtactgtg accctatttt taccacttct   22620
aggctgatgt gggctgggaa atgggttatg cttagaaatg tggagcctgc caagtgtggt   22680
ggctcacacc tgtaatccta gtactttggg aggccgagga gggcagataa cctgaggtca   22740
ggagttcaag accagcctga ccaacaggga gaaaccctgt ctctactaaa aatacaaaat   22800
tagtctggtg gtggatgcct gtaatcccag ctgctcggga ggctgaggca ggagaatcgc   22860
ttgaacccag gaggcggagg ttgtggtgag ccgagatcac accattgcac tccagcttgg   22920
gcaacaagag tgaaactcca tctcaaaaaa aaaaaaaaa aaaaaggaaa gaaagaaatg    22980
tggagccaca agtggtaagc ttgtagcggt aagcttgtag agaaaaatcc aaaatgatca   23040
tccactaaaa gtgttcaact ccagatcttg gcctcatcca cttgcatatc attcaaatac   23100
agtgtgcaaa gaatagtttt cttctttttt tctacctggt ctgatcttca tgggcttcag   23160
ctctgcagtc tagcagggat aattgacact taattaatag tgtttcattc tcctctagct   23220
tgaacatatt tctttctctt tcaacattga agccagtagt tctaaaaatc aaacatgcaa   23280
acatgcatca gtcacctgga gggcttgtta aaacacaggt tactgggtct gccctcaagg   23340
tttctgattc agcacatctg aggtggagcc ctagaatttg catttctgag ttcccaggtg   23400
atgccgacat tttggtccac aggccacact ttaagaacct ctgattcaaa ctattcagag   23460
tttatttcat atccaaaagt gattatttaa aaagtatctt agattaatgc tcctcaaact   23520
gattgatttt tccaatcatg taccaaatac atagtcctat ttcacatgac cagtattcag   23580
cttttgctgc aagcaactca ccatgccagt tccacacacc tgaacaggtt atatcctgtt   23640
taacaagatc agcccactga tcacatacta ggatgtcatg gcaatgtcaa tttatgatag   23700
aagtttctaa acatgaactt tcatctgtat ttatctcacc cccgaacagg aacagtttgt   23760
ggacttgcgc tggcccttgg accacacttc gagtgacatt gttatagatg acacggtctc   23820
ttataggaaa atgcacagtc tttcttagat tctctacctc cctcttccat ctcattccca   23880
acatagatct gggtacatga gtgggtctt attataatct tgtgacaccc ttggatcatg    23940
cactaccctc taaataatca atagtttcta ctatagagag gctcaattta tcttctccct   24000
ggaattggga ccactgaaat ataactagaa cccaactgat cttttgagat gttgtgtgct   24060
tgcccttact gctactgccg tagttctgaa catttcccca agcatcaaaa aggcccatg    24120
gcctcttttc ccctagacct ctgccagtcc accaacactc tcagtgggga agtaagaagc   24180
ctggtggatc ctgcttccca cacaaaggcc atgatgagac agatgctttc taagtccgat   24240
atatctaccc actttctgct gtcacctctg tacctcctga gtcacatgga atgtggtgct   24300
gagccaaatg gtcagtcttc tagaagcagt ggaatgttgg aggcagctta taccttagct   24360
gattcttaaa ttttcaggaa ttttgtgagc cagttttaa acacagccat tgttgaaaat    24420
taaacaatat aaacttataa tcaaatatat taaaaataaa gataatgccc tcaactcatc   24480
acttcctatt tattgtttta cactttagta ctatctatgc ttattgtatg tgtatggtgg   24540
```

```
aaatactaca taatgatatt taatggtgta ctgccacaca gctcttcaca actctgcatt   24600
cagtgacatc actttggtag cttgaaatca gccatgatag gagtatttat atcttggaaa   24660
ttggcaaata ttacaaatca gcattccacc ctcccttacc tccccacccc ccagccagtt   24720
gttaaacatt taccagcatg caaccaccca gagcctgcat ctgggaaagt gagccactaa   24780
cccaatgacc tgtgataacc ctatacatat ctagctgtta ctaagctgcc cttcccataa   24840
cggtctgccc caaaaggtg tgtgtgcaga ggagaataaa aactaaaacc ctaagatcat   24900
cttatttact tgccctattt ctgcctcttt tctctccctg ccatctctgg ggtccagaag   24960
tagaagcttt ttattgcctc cggagtttat tcttatacat caaggataaa cattcatgac   25020
ctaacatcat ctctcttgtt ttctcccgcc aaagctataa ggatagtcta atcatgaaaa   25080
aacattaaac aaactcaaaa tggggacagt ctataaaata cctaaccagt tctcttcaga   25140
acagttaagg tcctgaaagg cgaggagaga agaagaaaca atcacaactt ggaggacatt   25200
aatgcactaa atttaatatg gtttcataag ttgggctgaa aagaaaagga cagtagaaaa   25260
gctgggatat gagaatacag tctaagtgta gtactaatgt taagttttta atctctaact   25320
tgatggcatg gttatagaaa atagaaacat taggcaaagc tgggtgaaag gtatacagga   25380
actctactat ctatacaact tttctgtaaa cataaaatta tttcaaaata aaactaatat   25440
aagaaaaaaa catggccgac ataacagata gaatggatat cttctctagt ctatgaaaaa   25500
ccctgtgtcc tacattcact tgctttgtga tataataaaa gggggaaagg aagggatgat   25560
agaaacatta ttcctcttaa taaacttgga ttttaaaatc ttttatcttt tcacagcata   25620
aaacattcca cttaggatgc tatatgttga gcattaactt tctctttttc tttatagtct   25680
ttctgtaata gttcaaatcc tgcccaccct gagggtggat gtttctagat gatgaaggag   25740
gtcataaaca gagagtagat taatataatt atctttattt catgtctatt tgcaaatggg   25800
ccattgttca catagttgtc tctctttcta aatggaagaa tagttggagt tggggtggg   25860 gaaataccag aactgagagg agtaaaggtg cttcaagaca atgcttctta aactttggtt   25920
ttgtgtttgc atctcttggg gatcttgttt aaagtaggtt gagattcagt atgtttgggg   25980
aggggcccgt taatctgatt ttataaaaag ttcctagatg atgccatgct gctggtctct   26040
gagaagcaag agtctggggt cctttctaaa gtgtttcctc tctcctctat acagtcagaa   26100
aaggaaagtg cttactggtc agagatttaa aagacatagg agatatacca cacttctata   26160
agaccagaaa caaaaacaaa gaaagaagaa acataataac caaaatatga cattattgca   26220
cacaatgaga tgcagtaaaa gatggactac ttaggcattc actggacata agtgaagctg   26280
cctttggagt ttaattttaa gttctcagta actcactgta tttagtcata tcgtttcaca   26340
tacagacaaa attccttctc tactaagaag gaactaaagc tctcagaatt actgagttgc   26400
acagtaccaa tttacatgaa tattttctt cctctaaaag tttgtaatga ctatggttcc   26460
tggaaaataa tatttcattt tttcaattca tactcttaat ctaccaaaaa aacactcttc   26520 caaaatata agctagaaaa acaggtaatt tgctcatatc atagagacaa ctcataccaa   26580
taaaaaaata cattttaaaa tttgaaaat tacaatgaga gaataaagca ttttgcatgc   26640
agatgtgtta tgttttact ccacaatatt gggagcttcc aaagtgtaac atgcatttac   26700
agagccactc tcttagcatt taaactggga ggcattttc gagaagcatg agtcttgctc   26760
agcggtcctg tagccactct agcaatctca cacagtacat gacttataaa tattgtatgt   26820
gcttgatgga agtagacctg gctttgctaa tcacttacca gttcttttgc ccagtatttc   26880
```

```
tttgttttag aagtaacttt gtttagctta ccaaatgtat attgtccaat tgtaggaaa   26940 tataagtaat attgcaaaca gcaaatggg attgtatgtg cagatctctg catcctggtg   27000
ggccctgtca tgttagtaat agcttttcct tgtgctgttg ccactgccaa acagactgct   27060
tatgcgatct ttggctttct taactcctct ttggggatca ataaagtgtt tctttttttt   27120
cttagatacc aacttcatct ctctttaaga atacaatatt agtttaaaag attgttcaac   27180
ttaaagcaat cttgtagaga ttgtcaccca tgattgatgc tgggtgagta gaaaggaaaa   27240
tgttgatttt atcctctgcc tttcagatct ttgaagggga aagtgggcta gttttttaaa   27300
ctgcagcctg atcaaatgtt tcaaaagttg ttcaaaagta atcttagtcc aacactgctc   27360
ctctgacttt tatctagaga aatagaaaag tttatatatt aacgatttgt ttcttttaag   27420
tacttgtgta cattttctc ttgcaataag tattaataat tgaaaattat taaattgtca   27480
ttttaatgtt ttttattaag taagtttgat atgtttctta gcaacgaaga cctgtggctc   27540
aaataggagc agacaattca tggaatcaaa ttttaaattc aagcagagct atcatactga   27600
catatttgta tttcccttg tcttggaatt attggtttgt ttaaaataat aagtttagcc   27660
aattattttg ttattctgtt atttaaaata taaatttgca gtctaaaatt ttttgtgtaa   27720
aggtgagtgt ataatgaat ataaatataa ataaataact aatgatcaca tttctactgg   27780
gaaacatcat tatttcttac tttaaatgtg tcaattatct ttccatgatg tgtttgtgca   27840
catgcaagtg ttggctaagc ctgattctct tttataaaaa aaatggtaaa tctcaaataa   27900
aagtgcaaaa tattatcttt catgcaaata cactaataat accaaagaaa gcagaaaaac   27960
ttacttaaaa ataattttc ttgacaagag atttataaat agcagcttga ctaatcaatt   28020
tcattactgt tccttagctg cagccatgtt ctcttggact atattgctca atgatcttgt   28080
gctttctttg ctactcatac taaataattt gtgttgtttt gcatttttta tatcaggaag   28140
caaaatactt aaaaatttat aaaagttgaa gggaaaaagg gcactcccat agtagataaa   28200
agaaaatgta gcattacttc atcatcttta tggagactct tcagaaagat gcatggtttt   28260 tttagaaaata tgaaatgata tagtatctga aagttgcttt aactactaat gattgggatg   28320
gtaaattggc acaaccttc tgatgggcag gtgggcactg gtcattaaaa aacaaaacaa   28380 gaaaacccttt aagctgtata aagctattca tacagagaga tttacttttta taaatttacg   28440 ctaatgaaat aattatggtt gtgttcccaa tttagcataa gaatgtttat cacagcatgg   28500
catatattgg aagtttagta aatgaagata catccaatct gacattctat tcacaaccac   28560
aaagagataa tgtagaaaca tatttagtaa tgtgagaaaa tactaaatat taagtgaaaa   28620
aggtaagtta caaataatt tgcataaaat catctcatac accaccccc catatatata   28680 cttatagtat gttatataat gaatgttaa cagtctctgg tttggggtgt tggattatga   28740
aatacatttt tttctcatat gtatattctt gacccttcaa ctaacaagca ttatgttttt   28800
aataaggaaa ataatcattc acctttaaaa aatgaattcc attaatatgc ttccatttgt   28860
cctttgaaaa tttaataact ttatatatta gttattccat aataagtagt tgattttgaa   28920
aatagaaaat taggtagttg ttctaaaaca aggcaagaaa gggttgtgta aaataccata   28980
atgacttatt ttattaatag ataagccata aatatcctga tgaattattt tctgatgaga   29040
aataagaatt gctgtggctc agagttacat tttcttgtaa tgtgaccaag gccaaaagga   29100
atttgatagc tattccaact ttgtatcgta aggagtagtt tttaacattc ctgaatagat   29160
aagatagctc ctggaatctt cccaattttc aactatttct ttgatgacta tctatagtga   29220
ttgatttgtt gatataaatg ttaagctgac atatatttac taaacgtcta ttattagtta   29280
```

```
gatattacta actgctatgc ataccagaga gcatgaagta taggctctca cctaaaggaa   29340
ctacagtatt gttgggtaat aaattgtatg aaacagaaca tttttagaga atataatgca   29400
agtactaaaa tgactgaaga gataagaacc atgatattta taaagcagtg gataaatgta   29460
ggctgagagt ttgggaaaaa cttcaagaaa agttgtgact tgcctggctt tggaaagata   29520
agtgatactt ggttatgaga gaggagggaa aagcatttca gcttgtgaga tgaaggtcta   29580
aagtccttag ggctgaattt gctggttgtg gctatgttta ctgcagttcc agcagagtta   29640
gagatgtggt taggccagga cagtaaggat atctgcctgg aagattcctg ttttcccttt   29700
agagggaata gattaaggtg gcagggatca ggtaggaaat gatgggggac cctgaagtta   29760
gagctgagaa tgtcttctca gcttctctga taccatgctc taagtttgct cccatttctt   29820
tcgtggttcc ttctcttttc atttgttggc tcccaacctc ttctctactc agtctctgaa   29880
tgttggactc aactgaagtt ccttagctgc tcttctgcct ctgttctcat tccctgaatg   29940
aaaggagagg gttcaaacta tccaccacta tggtttaata caattacaga gctccttgga   30000
aaagtgattt gtctagggct ggggagggat aaaagaagat gagcctggag gatgtcatgg   30060
taccaaaaag taagtactca agaaaagcgg ggggcacat tgagagaaca caggagccaa   30120
cctaaaagag ctaccaatgg ccaaagctag accaatttca gacaaaataa aatattgaat   30180
tatgaagcag aataaaataa acacaattta gtccatactg atataaataa atgattgaat   30240
aaaagtaaat ggtagagaaa ggacaacttc ttacagaata attccaaata atagatgcaa   30300
aaggaaagga ggaaatagaa atcgttgtg agaacactag aacactggtg aaacgttgct   30360
gcagggagga tctgcctatg catgcataaa ttaatggaca atgttttgag agaaaatggc   30420
tatttggggc caggtgcggt ggcttacacc tgtaatccta gcactttggg aggctgaggc   30480
gggcggatca ccaggtcagg agttcaagac cagcttggcc aacatggtga acccccgtct   30540
ctactccaaa tacaaaaaat tagctgggcg tggtggcagg tgcctgtaat cccagctact   30600
caggaggctg aggtgggaga attgcttgaa cccaggaggc agaggctgca gtgagccaag   30660
attgtgccac tgcactccag cctgggcaac ggagcaagac tctgtctcaa aaacaacaa   30720 caacaacagc aacaaaaaac acaaaaacaa acaaaaaacc tttacaataa ttaaaaagca   30780
tggtaaacac cacattagcc aaatgatcaa ggtcaacatc accagtaata agacatactg   30840
acaacaggta ctgtgaatat gatgcactga gaagagcacc tcacctctgt ggtatctttc   30900
ctgtgaatac atagcctcaa tttgatcatg agaaagcatt aggagatata tctaatgtta   30960
aatggcgagt taatgggtgc agcacaccaa catggcacat gtacacatat gtaactaacc   31020
tgcacattgt gcacatgtac cctaaaactt aaaagtatag aaaaaaaag aattactcag   31080 actaggagac ccaatatttg aaatacaaag taaacctcta aaaataaata aataaataaa   31140
tagctattac tgcaaaaaaa aaaaatgca aattgaggag tattttacaa aatacctgac   31200
agatatttct caagagtgtc atgaaagaca atgataaacg aggaattgtc tcagattgga   31260
ggagactaag gtgatgaaga attaaataca atgtggaatt ctggattgga cccaggaaca   31320
gaaaaaaggc attagtggaa aactggcaaa atctgaataa agtctgtaat tcaggtaatg   31380
atattgtacc aatgttaatt tcttactttt gatcattgta ccccggtcat gtaagatgct   31440
aacattagaa gaacctgagt gatgggtata tgggagctca gtgctatctt tacaaatctg   31500
taaatgtaca attatttcaa aataaaaagt taaacataca aaacatctac ctacagagac   31560
ctctcagtcc tctgtttctc tgataggatc ttattttct gccttttaa aatctttgcc   31620
```

```
ttcttcctgt ccacatttaa aatcttcacc ccctttgtcc tcacatgtgt ttatcttgtc    31680
accttgaaaa caaaagccac tgggtcttct ggataaattc tcagatggaa gtgaatggca    31740
agtctccttt tgccctccaa gtacagaaat cctagataaa atattgtttt taaaatgtat    31800
aggtaaactc aaacagggaa aattcccagg tgccagcaca gaaagcgatg gtctgtagac    31860
attagaaacc ctggacctga gggcaggact gaagttgtaa tgccattgct gggacaggaa    31920
agaaagcttc aggcatggat aaggtaagga gctagaactg gaccctgcat cctcaaaaac    31980
acagggtgta ggaaagaccg atcattggcc ggggaggtgt caaagatgtg cgccttatgc    32040
taggggccac aattgggaaa ataatcactc ataaattatc aaactcaaac ctgcactctt    32100
tgtagttgtg ggatccaaat tcatactatc tatatggcac agaagctaat aaatgaacgt    32160
agaaatggtt atgaaatggg taacacttct atgggcttgg cagggacaaa tgcaaaacca    32220
ctttgcaggg atgttttcat aagcctgagc aagagagtct ctcaggtaaa aagctactga    32280
atgtcagttt actatcaaaa attataaagc aaagaaacaa atcctcatca gcaatgaacc    32340
cagaaaatta acactctaaa aactaaagat aatttaaaaa atctaaaata tagttttgaaa   32400 taagtatgtt taatttgttt aagaaaaaaa tgactatgaa actagaaaat gaagattttg    32460
gaaaacatgg aattttagaa ataatccgtg taagccgttg atattaaaac ctcaatggaa    32520
gtgttacaca cgagattaga cacaatgaag agcaagaatt agatactaga aaacagatct    32580
gaggaaatca tccagaataa agatcaaaga agtacagaga agaaaatttt ggaagaaaat    32640
ttgattcatg aagggtagaa ggtgaaggtt caatattttt ctaaaagcaa ttctacaaga    32700
atagaagaga gatggagaag caatatttac atttttatcta ctttatggtc acacacatat    32760
atgtatgtgt gtgtgtatat acgcacacta tatttgtgtg tgtatatata tatacatata    32820
tatacaccta tatatacagg tatatatata cacatatata tacctattta tatataccta    32880
tatataccta tatatacacc tatatatacc tatatataca cctatatata cctatatata    32940
tctatatata cacctatata tacctatata tgcctata tacacaccta tatatataccta   33000 tatatacacc tatatataca cctatatata cctatataca cacatataca cacatataca    33060
tatatatacc tatatatata catataccta tatatacata tacctatata tatacatata    33120
cctatatata tacctatata tatatatata tatataggtt tcaccacatc ccctttagta    33180
aatttccata tggtctagca aatcctttat cacatggcat cactcttatg tggtaactca    33240
actgaaacta acaacttaat atttcgatag gactattaca aaaaaattgt gctggaaata    33300
aaatgaaata gacttggcta acatggacct tttataattg gagctcaaca atgaaaaaaa    33360
tagataatta gtaggaaaag taaaagttta gttttagggt tctgtaatat atagggtcgt    33420
gtgtgtgtgt atatatatat atatacacac acacacacac acaaatatag tgtgcgtata    33480
tacacacaca gatacccaat agctggtgga taataaggac tgtctgctgt actcagcata    33540
atctcactat ttattaaata ccacactcaa ctcatcatgc tattgctgac tggaaacatc    33600 ccttttcct ttcatccaaa ttattttact atcttccaga tccaatctaa gttttgactt     33660
ttctatgaag ggatctcaat gatgcatctc ttttccttac acttctgtta ttgttgcatc    33720
tgaaccactc agtactaaat tgtgttctat ctacaccaag cttgtccaac cgacggccct    33780
gtggctgcat gttgcccagg acagctttaa atgcagctca atacaaattt ggaaagtttc    33840
ttaaaacatt atgagttttt tttagcgatt tttttaagc tcatcagctg tcggtagtgt     33900
tagtgtattt tatgtgtggc ccaaggcaat tcttttccca gtgtggccca gggaagccaa    33960
aagattggac gcccctattc tacaccaaga gttaggaaac tatgaaagcc aagcaaatcc    34020
```

```
tgtccactga ctgttttttgt atggtccaga agctaagaat gatgtttaca ttttttaagtg    34080 gttgaaaaaa aaaagagaag aagaatgttt catggcatat tagaaattat atgaaattca    34140
aattttggtg tcctctcagt gtccaataaa gtttattgaa acacagtcat gtccacttac    34200
gtatgtattg tctatagctg cttccacgct gtaacagagt tcagtagctc aatagaaaa    34260 tctgtggtgc acaatggcta aaatatgcac tttctggcca tttccagttg aagtttacca    34320
gtctttgttc tacactgcaa ttttgtcatg tcaagtacag gattttaaga aatgaatctc    34380
acttcatagt gcaggaggta gcagtgtccc ctctccctgt tgggaactgg actcaagagc    34440
agttcttttc aaagtggtcc tcctcagaaa ttcctctttc atctctcaaa cctgacactt    34500
ttatatcctt gaggtgggtg agggcttcca ggaaatttgt aactaggttt cagcacatcc    34560
cctttagtaa atttccatat ggtctagcac ctcctttatc acatggcatc acgcttatgt    34620
ggtaactcaa ctgagaataa caacttaata ttttgatagg gctattacaa aaaaattgtg    34680
ctggaaataa aatgaaatag acgtggctaa catggacctt ttacaattgg agctcaacaa    34740
tgaaaaaaat agataattag gaaaagtaaa agtttagttg tagggttctg taataatttt    34800
ttaaataaga taagcaggtc tttacacatt tgaaaagatc ctgggtgaaa ctacggagca    34860
aaaatagcgt tttactgtgg tatcattttt cttttcttgg cttcagctgt gtgtttttag    34920
tgaaataaat aagtattgaa tgtcttggga gatttgtgat tttctttgat aactgctaag    34980
acaccagagg tttcaattgt ttttgatcct ctttgatctt cctcagctac tctttttttca    35040 gcattgtagt atttttgaaa ttttttacatg agaatgaaca ataaaagtta acactgtcat    35100
aattaatttg aagagtatgg ctgtgtttac acaataaaac catttgcaac catcatcttc    35160 atcttttttct cagtagatta atttttcatt tgcatatata cagcataact gcagcaatag    35220
caagcaaata tctttttgtc tttccaaaag aatacttttt taaaaattag accatttcat    35280
agtcttgaag tttagtgcta aagcatttca aacagcattc gtatctgaaa acctaccact    35340 gtctttttaca ggaataacag aatgtttaat aaccaaactt tagccatacc aaactttgaa    35400
tttccccaga tgcctaagat ggcaatattt catgggtcct ttctagtagc tctgtttaga    35460
aaacaaaaca gctaggcttt gtttagatgg ataattcaac aaggatttcc actaataatc    35520
atgtccagtt cgttcagggg gagcacactc aagtttgatg ctgcatcaac cgagtataaa    35580
ccaggactgt tttctgcaat tttagctttc agtctgtatt agctgtgttt taaaagaac    35640 aagaagaaaa gaaaaaggaa aaatgtaatg ttaataggct tcctttttgtg atctcttagg    35700 gagaggtctt tttaaataag gggcttgaac ttgaccttct tcaatggcac aaaggtccaa    35760
tgcgcagttt ttaaagctat atttaaattt taataattat actcattgga ggctagaatg    35820
agactttcag aacttaatcc tcaatctttt agtgaaactg cttggcaaag aacagaagct    35880
caggaaaacg tctgcagtag gtacacaaat atttccctga tttcttcatc ccacagaatc    35940
aaactgactg ctttgaggtc atcagtatag tatttgagtt tgcaaatgta atttaatata    36000
gagttataat ttaaaaaatg cttatcttca agataaatct agttttagcg acctgatact    36060
gaaactagat tttcaacatt ttaaagaaat cacactctca gtgttggcaa aatggcatgg    36120
aaagagccac tgttgtatgc tgttgttgaa agcataattt tttaaaatct ttctggaagg    36180
cagtttggcc atatctgttg aatgcctcca aattttgcat aaaacctttta aaccagcatt    36240 tttactttag gagattcatg ctaagaaaat agtcgtagat gtttgcaaaa ttatagctac    36300 aagatttttta tgtaagtgtt tttggtagaa acaagaactg gataaagcat aaatatttaa    36360
```

```
caaccaggct ctattcagcc attaaaaatg atactagaga aatatttaat gccatggaaa    36420
tggttaaaaa agctgattaa aaacagtatg cacaatgtga ttcccttttg taagaaaaaa    36480
aatttgcatc aaaaatactg gataaaaaca aatagaatgt taacagtaga atctgtatat    36540
aaaggaattg tgaataccat ttttccaaca tgaaaatagc ttcttaaaat attcttaaaa    36600
ttaaaatgca tagtaggtgt aaaaatctca aactatagga aagtaaaaat tgtaagccct    36660 tttccttta attgcataat ttggtagggg acacacacac acgcacac acacacacac    36720 acacacacat acacatgcta ccttctgttt tggtttttta ttcaacagtt tatcttggag    36780
aattttacgt gttagtgcat gtagatctac ttcattcttt aaatttctat gtggtattcc    36840
ataatatgat tgtgtaatac cctttcttat caactactct gattattctt atcaactact    36900
taccacactt atcagctact ctcaccattc tgttccaaca gcaggattta tagatttgac    36960
ctttttcttc atttcctctc tgcttttcac ttctctcctt ttccagctta tatagttatt    37020
atttcatttg acgctctctt tttttgcccc atctgcaaaa ccacaactct caattccctg    37080
tgtaaccaag cagacaagca ctgttgaaga aaatcctgcc atagggcagt tatgtcccac    37140
cttttaagac actcaatact acccggcaat cctgctagtt tctctggtga ggtcaccctc    37200
tcactgtctg ccactattat ttcaaacggt ctccattccc ctcaaaagtc agatttccct    37260
ggatctcctc caactttccc tctcagagac tgatgatgtc tcataatata gaaaaattg    37320 aagccttgac ttccatgtac caattatata accttctcaa ttgtgtatct tttctctctc    37380
ttccttcttt ttacatggaa gaaatgtatt tgctttgctg ttgtttcatt taggaatttt    37440
gtacatattt ttatgtaata ttatttaac agttttccta tgtagactgc ttttcttagt    37500
tttgatatca gggtttattc tgcttgactt gtagaatgac ttgggaaact ttcttttgtt    37560 tctttgctt ttcctttac tcggtgctct aagaaatttg ttccttgaaa gtttggtagc    37620
agcattttgg tacaagtctt tgagtagtgg taagggtgat attagtgtat gtgtgtgtgt    37680
gcctgtgtgt atgccaatct ttgattaacc ttttctttag tttctcctat aattattggt    37740
ctatctcaat tttcttctac ttcctaagtt cattttggta attttatct tcagaaaaca    37800 tctactttgt ccttcatcta gattagggat ttgtttcttc cctgtggaac tctttggcag    37860
ttgatcaagt tgatgaagtt gataaagacc tcttcttaga atcatttaaa aaaatcctac    37920
ttgggagtgg agtcacatga cttctctgtgc cttcctacaa aaatgtgtgt gtgtgtgtgt    37980
gttttctgtt tacatacatg gttttctcac aatgctatct taatatgctc agtaatttta    38040
tggaataaaa ttgtataaac cctgcttgaa taatatattc tgtgtgcttg cctcctttac    38100
ctcataacac agtgtacaaa agggaattg aagaggaagt caaataaaga aagaaaata    38160 ctacccgtgc aacttgcaac atgtacggcc tgtgtcacca cacaatctgt gaataataag    38220
aagttacttt aaataatact tcagcagtta tctcaatcat gtgatttgtt tgaacttcca    38280
aggctaatac tttcagctca acagttatct atattataac ataccgtaat gccttatgga    38340
gagttaaaaa ttctcatttc aactgtcctc ttctgcaaag ctttaataag taatgcaaaa    38400
aactcacccc ctttcatgta ttgatgaata taggtagata aaaattttag agggaaaaat    38460
aggggctggg tcaccaatat gagaacatag ataagtaggc acatttgcct ggtgggtggt    38520
cagctcattt gcagggcat ctgtagacag aaacttggag attatgtgca gtctataggc    38580
tgatctaatg actgccatga atgatagttt cacatagatg taccaactga aaatgacat    38640 acagatggtc cccgatttat gatggctcaa cttaagattt tttgactta caatggtgtg    38700 aaacaatat acattcagta gaaactgtac ttagagtacc cataaaatca ttccgttttt    38760
```

```
cactttcatt acagtattca ataaactcca tgatatattc aacattttgt tataaaataa   38820
gccttatatt agaggatttt gatcaaccgt aggctaatgt aagtgttcag agcacattta   38880
agacagttta gactaagcta tgatgttcaa tcgcttgggt ttattaagtg cattttcgac   38940
tttaagatat ttttaactta tgatgggttt atcaggatgt aaccccaaca taagtcgagg   39000
agcctctgtc aacatttctg tgacttttat tgatgaagtt cgcaaatatt gctaatacct   39060
ctgtgtttgt tacctaaatt cataattgaa ggccacgcta cacttgagtt agagatgagt   39120
ggaaataaag acataattta ttttaacatc taagattatg gacccattga aacctagaat   39180
ccaggattct ggagtcttga tttctagatt tactagtgta ttggtataaa ggagtatgta   39240
atataatatt ctcctttttt atgggtatat atttgctatg ttaaaaaatt atttctagag   39300
aataagaatt atacaattgc cttaaatgtc ttacttaata atgataattt aaattgaata   39360
aagattttaa tggctttctt ttttctactt ttttaatctt atgcttttt ctttattgca    39420 tgtgtacgta tatgtatata tatatatata tatatgtata tatattgctt catttgagta   39480
ctgaattgag taattcttgc ataaaaagtt tgtggatttt aagctgtcag agtcttttta   39540
tgcccatgag tgttttcctt tactcttaca catgattgat aattttgctg gacatagaat   39600
tcttggttca aaataatgta atctcagaac ccaagaagac attttttcat tgtcttctag   39660
gatccagatt gcagttgata cttttgtatt ctcattctaa tttcatgctt ttgaagctga   39720
aaataactct tttcataatt ttgtgaaggt tttgtgattt tttctttatt tttgaagttc   39780 tacatttca ccaggttatg aacatttctg cttgggagtt gatgttcctg tcagattaaa    39840
ggtttgcatc tgttttttcc agctcaggga attttttatt attattcttt cattattcca   39900
aacttattcc ttattaattc tgtctttatt gaatctctgt taaatagaaa ttgaaacttt   39960
taaatctata ctttattttt tctgtttctt cacactttct acacctttac ccttctcaat   40020
gcattctgac agaatggttt gcttgatctt tgaggttgct aatctgttca ttattgtgtt   40080
catgcaaaaa aaaaaacaaa cagattttc ttaaaaactg aaaatcagca aaatttacaa     40140
gagcgttctc ttgagtatat attgggtcac agattcctaa gtgttgctgt gaacatattt   40200
ttaccttcat ttttttttcc tgtgatttgg aagggacagt actggttaaa tgttttaacc   40260
aaccatcttg aatctggaat ctgctgattg ctatctagta tgtgtcaggt tccatgttaa   40320
tcactggata aacaatgcag gcgtagagac ctcaatcaaa tagaacatca tgaacattgc   40380
aaacactaaa gcattttctt ctgaggcaca cagaaaaagg tgagagaaag tggagagaga   40440
ggtgatctga acagcaaatt ggggtctctc attctgtata ctttcttaag gtgtttggat   40500
tttattatgt acacagtagg tagctgaaaa ggggttaaat tttgtgttta tctgttttag   40560
atagagatgg catcttgcta tgttaaccgg gctggtcttg aattccaggc gtcaagcaat   40620
ccttctgact cagcctccca agtagctgag actacaagtg catcccacca caccccactg   40680
gtttattatt tttcatttta ttttttgtaga tatgggtct tgctatgttt ctcaggctga    40740
tctcaaactc ctggcctcaa gtaatcctcc catcttggcc tcccagagta ctgggattaa   40800
gggtgtgagc taccctgtct ggccatgatg aaaagttttt aggaaatttt ttttaaaaa    40860 aaataccatg aaggatgaaa agaagaagg caggactgga aagggaaaat cttttaggag    40920
gtaattcctg tagtctagaa ggatcattgt catctaacct tttgcaatgg cactggagac   40980
tggaaaagga gcataaaata cttgacccaa taccttccct aaatgcgctt ttattagaaa   41040
ctggcattac aactcatgta aagagctaca tcattaacca acaaccacaa tggtcacctt   41100
```

```
tttgtaatttt attttgcttg ttacttttc cttatccaca ctatagtcag gaggagtagt      41160
gtcagtaaag ttttataatt ttagtactgt tatatgttgt gcaaatttta catcatgtat      41220
tttatgcata aagggtagat catgggctgc ttcaaaatga aattgtatta gaattgtgtg      41280
ggtacttgag tattgatagt ggggaatcac atgtaattct aaattgtgag cccaagtagc      41340
cagatgtgat attgagagga tgaggcaatt catccctaaa ctccaaggca gatactaaat      41400
tttctttcca aatgtcattg catggttgaa gattacaatg ctccctggaa gagcagaggc      41460
attcttaggt caaggataac tctcttacta gtagaattta caataaggtc acatttctct      41520
gactagaaaa gtgggcgttg ggaaaattta atagaagtgt agtaataaaa gttttttta      41580 aaaagtactt gttttacgca tagtcctatg tataacaaag cattgaggtt attccagcaa      41640
gacagatgtg gagcaggtgt tgaaatttaa tggataagta agtaatacag aggcagtaga      41700
tcagtaatgg agatggatta gatcatcaag gaaatgggta taaaacaatg tattatgaaa      41760
atgcctttcg attgttttct ttcaaaagtt tcttatgtc agatttaagg cagagtttca      41820
ggttcaaaat tttgggtata aagtgaagcc gtgtcttcag ttttttcaga attctgtgtt      41880
ttgtgaagct actcttgaaa gagtcatttc cccatagagg catatcttta agtctataca      41940
ttggcaaata aaatagtttt atagtctaat gtaccgaagt tcaggcata tttattatat       42000 taacaaacgt atatgaaa ataattgat tatgtaaat ttaaaattg cttgaaattt         42060 gtaccatgaa ttgatgtcaa ataatccca aatacaattt ctatatattg ataaagtggc      42120
ttttactaaa acccatatat ttttgatttt atgaaacagt ataaaattc actgaaagtc      42180 acctaattta ctgtgtgtcc ctcaagcacc agccgctact ctagatactt ggatacacca      42240
ctgaacaaat cgagtggaac atcccttct tgaggaactt attttcttgt gtggggagaa      42300
agactgagca ataaacatat tataaaagtt aaatacttag taaaaagtat aatgaaaaaa      42360
gtaaagcaga aaaagaaaaa gaaccaagg taagggat cagaaatgtg ggtgagatat       42420
tttaatttta aattttaaat agggtcttca aggtgggact cgttgagcaa gaaacatttc      42480
tgtgaagaca tgaaggaggt gaaacagtag aaaagcatta tgaagtgctg ccttaagcac      42540
tcttaaaaaa agaaatttgt tttcataggg aaatttgcat ttatctttta cttaaattgc      42600
tgaattattt tgattagtca aaattccaaa ttcacattac cccagcattg ttccctaaaa      42660
tatactgaag ttatttaca tcaatgtcta cttcttttgg aataatttat atcaatatat       42720
ttgttcatgc ctatctcaga atccaaaatg taggtgcccc tcttttaaaa agaaattata      42780
tatatatata tatatatata tatatatata tatatatg tatgtatgta tgtatataaa       42840
caaaccaggt atcatacttc taaaaagata aatgcatctt cactcacatc tcaacctgca      42900
ctgtatttga atcataaag cttttgatt tctaagatga tacaaagtga tatagggatt       42960
tttgagtgaa tgtagggcaa aactatttga ggtatttatt cttttgagt tcaataaata       43020 gttttccatt tgaaatattc atgttttgcc cttccatatg tgttcatttt cctacctgaa      43080
caataattgt ttgctgagga tataaatgcc tgtgcaatgt tataggaga cagtaggttc       43140 aatctgattg cactgaataa agtgcagtga tttgcactca ctctttcata agatattaat      43200
tttggagatt attggagtaa acccatataca ttatatagat ttgtcactt tatctatta       43260 aaaatgtctg ttttttattac cttctgacga ttgtctcact gtgctaaata ttaaactacc     43320 tctttttat ttagtcattc ttttaaggaa ctatgagttt catgtgccaa cttttaatt        43380 taattgatta aaagcaaaac taattttctt aatcacagtt tccttggcat tgcacagctc     43440
aacttgcagt tagagaaaag aatacaaaac aaataagcaa tctgtactta aaaaagttt     43500
```

```
tggacagtaa aaacaaatgt aaaattgtac tcaagtaagc aatgctaatt aagtggtaga    43560
gttgtatttt aaatgattaa atcaatgaaa gaaaatatct tatgcctttt ctttgaaaat    43620
taagcacttt tttgtgttct tattttggt taggataatt tggtgaggat aactcaaaga    43680
atagttctgg attattccta ttataagacc aaagaaaata gcaagatcag tatttgcaga    43740
gcttggtggt atatgtggag caaacaaaaa gggtcagaaa actttattgc ttttgagtgt    43800
gtgtgtatgt gtgtgtattt ttcagtgtga tgaggaaaac acctactaat tatgctaact    43860
ttgcagcagt taaacataac atatgatgct actttcttag ttatgcgata aggtatgtgt    43920
ttgctgctgt ggttgtgtga tataatgttt gcttttcttg atgttgttac atatcttaca    43980
actaatgacc tgttttttaa aatgtacaca tatgacacta atgctgaaac actaatgtta    44040
tgctttatta ggatttaatg tatggcaaat aatgttcaat ttttagcctc cacttattat    44100
gcagatttaa aaaaaactcg tactatttgc tcagcccag aaatgcacag aaacaaatag    44160
gggaaggctt ttgacctcag tgaattccca ggttattggc aaagtcaaag gggctacaga    44220
agtcagtatc atagtgcact gagggaagct atagccacta tgaggccatg taaaaagaaa    44280
tgtctaattc aggggtgaa gcagttggga gaggggcatt tcagacaaag gcccctggag    44340
gagatggatt ctgagctgag tgtctaggga aagcaggatt tagttaggtg aagaaggtat    44400
agggaagacc tttcagtcag ggaaaacaca gtctacaaag cagggatgca agagagaaca    44460
tttgaaacac ttgtcgttgt taaatgcaat gacatttcag atatgccatt ttcactcaga    44520
ggaaaataag caaaattgag atgccaagtt tggaaaattg atatcccatt tcacatctga    44580
attattgaga aatccttaaa cacaaaatat tcgttcctct gctgtttttg aaaactgaat    44640
gtttgaacat tacctcttct gctgaaagta aacactttat agtgacccaa agttttcctt    44700
gattttccta aatatactct attagaaaga aaatatagat tttcattgca tcaggaaatt    44760
catatgatcg atttgttgca tttttttggaa tgagcaatac acaatgaaag aagattttgc    44820
ttttgtctgg agccaccttc ctgggcctgc tagcaaactt gagaccctca cgctttcaca    44880
cctgaggcac agctgcaacc acatcaaggt catcagtaca ggatgttgat gcacacactc    44940
acacacgcac aaataataaa cttacatgca ttttccttgg ggcaaaagca aatggtatgg    45000
ttgagttttc ttttcttcgt cttcagcaaa gtggcatggt ggacattatg ttttatttta    45060 aaactttta atgacattta tgtattttca tacataagtg gaattcaatt ctgttgggcc    45120
cggataactg ggtgtgacct tggactgtct aggtcagaat aacctagaac attttgagaa    45180
ggtacaaatt ccctggttct gctcaagatc tattgaatca gaatctctgg ctataagtac    45240
atatgtttta tttttagcaa gtccccaggt gatttcttgt cactctagtt agagaaccac    45300
tggtatacat tttgcaactg ctttggccct gggttaagta tttagggccc caaataagtg    45360
aaaaccaata gcatatgttt gacacgatcc atcaaactta aaaatattta tatatacatt    45420
tcagaattat agtcttgtag cctttttat aatttcaaaa ctccttctag ccactatgga    45480
aaacaccaca aacataactt ttttgtgcat ctaatacttt cagaagtcca aagctcaatt    45540
gtatgaagca tggactgcct agcatttatt tcttcctgac acatttgatt ttgtcttaca    45600 gaaaatttt tctttactaa tttataccte tcaaggttac atttgcctac agactcttct    45660
ttcagtattt tcgtatttat gatgggcact gaaacctatt taaattattt ctgacataca    45720
ttttccttca aatgccataa acatttcttt gtctcactaa aatgtctagt gttagttttc    45780
tgtatttctg gttttaaaat atgtccacaa ttactattcc tcaatacaat ttttgcatag    45840
```

```
gagatcttta tcttttcaga tagtatcata atcccctatg ctattctgta aaaatacctt    45900
ctgagtcctc ttggatgtat aactggagca agtgaagggc aggaatgatt ttaatgtttt    45960
ttcttacctt ctgtttctcc atgccaggtg aagaatgagt gagctgtgtg tcccttataa    46020
tgtaaggaca ttttccagca tcactcatgc tagaaaagca aactaatacg ggatcctcaa    46080
aataaaactg tgaacacata gaatgccaga gcaaaatctc atccttagca tctcatttct    46140
gaacagttgt gttactctgt cagagttcaa ttggggaaca aaactattat gatatacaga    46200
atccataata gaaagacctt atacaaatgt gagggtaaag ttgaagaaat gtccaaaagg    46260
aggaggtaaa gattcaaata aaaggaccat tcagtggtcc ttttgacaca ctggtatgag    46320
agaaccagta gcttacagga aaatctggga agcaaagcat gtccagatgc tgaagttgta    46380
ctgtgaaggg gtgagagtag agaagtatat ggaaagctgt tgcctctgtg tcaggtggtg    46440
tgtctggggt agcatttgat cagcagtgcc acagatgaga agcagaactg gacatggaag    46500
agaagtgaag taaggacaag ctggaatcta taggcatctc tgcatctatc tttcactgca    46560
tctagccatg acaaacttca gagtataatg actacagctt tatctccaac tttttttttt    46620
tttttgagat ggagttttcc tggctggagt gcagtggcgt gatcttggct cactgcaacc    46680
tctgcctcgc gggttcaagt gactctcctg cctcagcttc ctgagtagct gggattacag    46740
gcatgtgcca ccatacctgg ctaactttt tttttttaa gtagagactg ggtttcacca    46800
tgttggccag gctggtctcg aactcctgac ctcaggtgat ccaccttct cggcctccca    46860 aagtgctggg attacaggta tgagccaccg cacctggcct acctccaact caaaaacctc    46920
atgtgaattt cgattttgat caactgtaat ctggaactgt aagtgaaagg aaactttggg    46980
aaaattcttc cagcatagcc aatttgataa attatcaata ggaaaccttt agagtcttta    47040
tgagtttaat gcatatactt ctatatttt ctagagcagc atgttttatt tcttttcag     47100 ttatagccaa gattttgttt taaactgctt taaaacaggc agaaaactat agcctccccc    47160
tccttctttt atacacttcc tacattattg atatcctatt tgataaatgt attttttcct    47220
tattgacaaa tatgctattg agaagttgta tgaaatctct gaagacatta ggacctgtgt    47280
cttcatgact tgagccataa gtcattcagc tctctggatc tgatccacca cattacatag    47340
cacatataag tcttttgata gccgcatact ttgagcccaa gctaaggaat catttgtcct    47400
tgctgtatag caaaccaccc taaaacttag aggcttaaaa caacaacaac tccttattta    47460
tcctgattct gtgggttggc tgagtgcttc ctctgctggt ttcatccagg ttcactcatg    47520
agggtgagtt ggctggagga taggctaatc tgcaaagtcc aagatggcct cattcatatg    47580
tctggcagtt ggtgcttgct gttcacaggg gcatcttgtt ttgcttttgt gtgctctctc    47640
atcttctagg aggctagact ggcttccttt tatactggtc tcaggacagc accccaatac    47700
aacaaactgg aagcttggag accttttaag gcctagcttc aggtgtcaca caatgttact    47760
tctgcacatt cttttgtca agttcttca caaggcaagg ccaaatttga ggagagggg     47820 aaatacattt cacatcttat gagaggagat gccaaatgct gtggccatgt ctttcaatgt    47880
acagttgcat cttaaacgag aaattatctt ttagttaggt ttctttagta agaaattcca    47940
ccttctgcct ccctcatctt ccctcccaaa atacacagac actactagta attttgtata    48000
tgagtggttc tcagttgagt gcagttttgt ccctgtcttc ctcaagggac atttggcaat    48060
gactggaggc attttttgatt ctcagcgaga cttgggagtt actactggcg tctagtggct    48120
agagaccagg aatagtgcta cacatcctac aatttataga acagctccct gttacaatca    48180
gttatctggt ccaaattgtg ctgaggttga gtaaccctgc cttatatgga atataatgct    48240
```

```
agcaagttgc ctgagtaaaa cttttggtcaa gagtaatacc taaaggtatt cttttttacac   48300 agtctgaaat gatttaaaat tttgaaggaa tcataaattt cttttttgggt ggaaaggggc   48360 tagttatgga agctgccttt ctgtcattca ttatttatga gcaaaccatt ttagatagaa   48420
tatgaccact caaacccttc tttaagattc aaactgaaca cagtacttag actttcgaga   48480
ctctgcgtgt ttaattttca cctctcattc tggcttttac ctttgtgtgt gcacacatgc   48540
acattgtttt agctactttt gtcagaaatc ttttaaggac ttttccacat tgttttaaag   48600
gttgaaaagt atgtattaat tggtcaaagc cattgtctct cattaaatca ggaataacaa   48660
tttacataga accctgtgat ttttgtactt gtatctttag atatgggctg ataaaagtta   48720
aacattctct accatattgt tgttatgaga ggctgaaatt ttcaagattt cccctccaga   48780
ataaaacatg gtgcaattta aaacaaaatg ggacaaattg gtgataacgc aaaacaagaa   48840
ttgtgtacaa taaattagat ttccttgggg cagagaaaaa taaaaatgct gaaagggat   48900 actgggtaca gttttttcat tgttttaaa ataagaattt taaaaataga aatgggcaga   48960
aactagttat gcattgtagc ccttttccat attccaatta caattcttgg gttactcctg   49020
gcttgcatgg tcaccaagtt tggttattca tgtttctcac cctaacacac cccatctgct   49080
ccctcctgaa ggtgtgtgat cacaggtatc ataccttatc aagcaatatg tagtgacatc   49140
ccctctcaac tgacagaggc tgtttgttgt tgtgcccgtt ccaaagcagt gttgactgat   49200
aatggtagag tggtacataa tttgaattcc tcagtagaag tttattacat tagctcaggc   49260
ctgaggattc ttgcacaatt ttgagagaaa gagagcacaa gaaagaaaga cagagaaaga   49320
taattcttga aaattcaaga attcattgag atcaataaaa cagttattct aatctgtgga   49380
tgagaccaaa cccatagctg taattaagat cactttggtt gtctcaacaa cagattaatt   49440
cctcttttca gttaaaaggt tgatgtcatg aaagcaatat tttactggag agaaattgct   49500
aaaatctgtt tgcttaacaa agcaattatt gataacctgc aattgcttat tgcttcccct   49560
gtcatcgact tgttggcaaa aacagtctca cgtctcgata gtgatgccta cttttacttc   49620
agggaagact gataaataat atagtttttca cagaaacatg taagacaaca ataatcctta   49680
aactatgagg catcatatcc acaaaaattg aggaagcgtt gctgaagtac taaacatatt   49740
gtttgagttc tctgcttcag gagtattgac ctttgacttt caattgatat ctctcttcag   49800
aataatagtg atgaataatg gaaataaacg tctttaactt gtggtgtcag caacaagatc   49860
ttttccttag ggaacttaac atatgggtat cttccaggga gcggataaat gaactgattt   49920
tgaagtgctc tcctaatgca aacatttct ttgtaactgc ctcagaaaaa tgcaggcatc   49980
caaggtaggc cttcatcagc cttgaagtag ttgttttgtt tgcttttta tttttgttt   50040 tttatcaaga ctcttccttc tctcactcag aaataaatag caacagcttc ttgtgacatt   50100
ggcctatatc ttgagttctt aaaagtgtaa aacactggtt ttgaagtatt actgcaccca   50160
attcccaagg tataactaca ctcacttaaa tggctcacaa ggatagctgt accattctta   50220
ccactttagg gtatcacttc ctttagatgg tagcaataag aatagtgcaa gattaagact   50280
cttttctagt agccatggta agagtaccac ctgacatttg tagagattgt tatacatttt   50340
caaagtatac ttaaatgcat tagagaaaga ggcagtgtag tgtaaaggtc aaaaacttag   50400
actttggagt taaggcaaca ctttttttagc aatgtaaagg cttagtttct ttatctgtaa   50460
aaatatagat aatagtacct aagttgtagc attattataa agattagatg tatgcgaata   50520
gcttagtctt ataactgtgc cctagttagc acagcataaa cggtagctat cattgttact   50580
```

```
accctaataa tgcaggtatc cttttcactt gttttatata tttagatctt aagatagtta    50640
ttataaattt attgctacag tacagaattt tttttttaaaa atctacatcg gaactgagat    50700
ccctggaaaa tttgcaccac attccagcaa agaggcacaa gagaacaaga taggcagttg    50760
aattctccgt gaccaaataa accacattct catacaaagc gcctccaaga tcacagattc    50820
cagctgacat cttctaaata gtatcttcaa atactgtaaa catggctaaa aacatcttct    50880
aggttatcaa ttttaaacca gagactaaaa tttggatagt gctgacggag caccaaatag    50940
tgctgaaaca gattgcatca gcctcctatt tttgcactcc atgccattag gaacaccttc    51000
ttttacgatc ttttttctgag gtgctaattc actaaacaaa cagtacatgt tacccccaggc   51060 accaaatcct tcaggatgct cccaagttgc ccattttcct tggaatggtt tgggggccac    51120
agaaagctca agaactgttt cagagcctgc tgcctggggt gccaaagaat tatgcacgaa    51180
taaaaccctg cggggaaaat gtaagatgct aacttagaat ggatagaaag aaaaaagaat    51240
ggatagaaag aaaaaagctt taaccatca gcaaaattca aattagaaag ggataggtag     51300
tcacaaaaat gatctgaatt gtgatgtaaa acaaatacaa aaataacat gctgaagtct     51360 gatgttctgg tgtagcaaac ccattcacta attctgaaat ggaatactat tcttatatga    51420
tgcacattat agtcccaaat gccaaaatta gaacttagac atatataatt ttggggagac    51480
ctttaaatat gagaccctct ttgagcattt aaaaaatatt aaacatctga aaaatgatgt    51540
acatacatct tttttaggat gtatatatat tctatatcag atttttttatt ggaaaatcta   51600 agccatcatt accctgagag agggcagtca aggagagcag aagagcccca agcatgtatt    51660
ctcagagtcc gtttactata aattggaaaa gacaaagaaa atgataactg taatcaattt    51720
gcctttacct tgatgtcatt ctagaatttt gaaccattta attttgtttt ctcccaatcc    51780
tggccacagc acttttttct ccttttagct attcattgag aaaacatgag aaataaggga    51840
ggcttcaaga atggtttgag gtagtatgtc catcccccag gttgaagagt actctgccat    51900
ttggttttgg tggcttctcc ttgccttatg tttatctagg tctctggctt cagatctggc    51960
atacacacaa catctgtgtg tatgttgtat gtgtatttta gatggttgtc ttcaattaga    52020
gaataatact tctgaggtgg catctcaggc atagtcattt tttaaaggag ttcttacttt    52080
ctgggtatgt tttgcttaga gataaatatg tttatcctcc gttttaacac caaagagatg    52140
gctgtaaaaa cagttggatc caaatgttaa aagtaaaatg ggaaattctc tttgagcaga    52200
gtgtgcaagg aaagcaatat ttttgtacag tttgctattg ttttatgaat ctttagtata    52260
ataacaccct gatgttttac tcagctcatt tatgtgtctg catattcact ccgaaatcca    52320
aaatgtcatt tcaaacattc ccagacatgt taattccttt aagttggtgt caactatttc    52380
atatttccca actttatcaa ggtataatgg aatgaattac aatttctagt tcttagaaac    52440
agctagaaaa tttgttcagc ttggtgttta aaaaagcaa atggccagtc cttagtttct    52500
gcttcctcaa cagtttatga ctttgcagga gttattcaa tgacttctct tggtaactgc     52560
caagccatct cctgcatttg atttagtttc taggagacat tttctagaaa aagaagagaa    52620
tgcttgcaac aaagatggca aatagaatta ctgaatgtaa ccctttccct gtaggaatct    52680
tgatgggagt aagcaaatgt ttgattggtt tcaccaacct gggtcaagtt gctatgtggg    52740
tgactctcac ctggagatct ggtgtgagag actgaatact gaagtcttga gagcatggtg    52800
ggaatgaagg gctgagacaa gggcaccaaa ctcagaagaa cttaaagcaa tgtcaggagc    52860
tgagatgtgg aacctggaag ctaaggagag catgacagtt tgggctgaag tccaggtggt    52920
cagacagaaa ttcagtgtgc atgtagttat gggcattcta aggttaggtt ggattcattt    52980
```

| | | | | | |
|---|---|---|---|---|---|
| ataggacttt | tgggtgagcc | taagacacaa | gattcacatt | ggctaaaccc | acttactata | 53040 |
| tcttaggata | acaaattta | tcctttacat | aaagatagta | tctttaattt | gtttcaaaac | 53100 |
| tatgtcttga | gcttcataat | gcattgaaga | aggggatgag | attaagttta | gaatatgctc | 53160 |
| tatttcctgt | tgcaggattt | aaattatgaa | tgaatgagtg | tgtgaattag | atctatttat | 53220 |
| aagttaactg | tctccatctc | ctttgtttat | aaaatagctt | tatgtgttga | tttcatgaca | 53280 |
| gaaaaactca | gccttgaagg | ttttcccaac | aaaactataa | ctttcactta | agtttttcat | 53340 |
| tttctgactc | ccatacaccc | ccaacccacc | ctcacaaaca | cacacacaca | cacacacaag | 53400 |
| cacacatatt | ttacagttaa | gtaaagata | tccctctgga | atttcatttt | ttagggttct | 53460 |
| ctaaatttt | tcaagcttct | ctcttttttt | aaacttctgt | ttttggttct | attcccagaa | 53520 |
| cccatataca | cctcacccag | agtttacctc | gaatccacta | atttactgcc | ctagtcatga | 53580 |
| aatgtaactt | attcaatagg | tgaggttttt | tttcctcctg | agaatcccaa | aaagaaaaat | 53640 |
| catgaaaatt | gcatttattg | gtcagaattt | ccacgtttca | aagttctgat | attttagtat | 53700 |
| ctgatcagga | gagaaaaaag | tctttcacat | ggaaattaaa | tgatttatac | aaattagttt | 53760 |
| gaaatttgag | atagaaataa | gatcattgaa | atatattcag | agatttagcc | tgaaaataac | 53820 |
| tgagtcttga | ggtcatcatc | tgaaacaatg | tgccttatta | ttttgaaata | attataaaga | 53880 |
| tggttcgagt | aagcctatag | ttctagaaaa | ttccttatag | agttactata | aatactgaac | 53940 |
| agtagtcttt | gaatcatggg | gatgaatggg | tttcatataa | gtcattcaca | aatggctcag | 54000 |
| tggacaaatt | ttatctcaga | aagagaatgc | cccataggag | ttaaaattat | catggctgag | 54060 |
| aattcctaga | tgatgtcacc | agaatctgaa | aacactactg | tggatgcaat | aatgatgcta | 54120 |
| tctgcatttt | ctgggtctaa | cttctgacaa | ggaatctgag | ttttctggca | agcagaatgc | 54180 |
| acatcagagt | acacaagggg | catgtcttgg | caacttccac | ctgagcacac | atgcacggct | 54240 |
| tcctgttttg | gtctgatagc | ttcccctggg | cttttgttaa | tgcaaaatta | cccacacaga | 54300 |
| gatgggttgc | ccatgcaaaa | gagtaggtgt | cttattttgg | gaaagtttgc | ttcacattat | 54360 |
| ctttgttgtt | ttattctact | aaccctattt | cctctttat | tttacactag | cgttttaaat | 54420 |
| tcacttcatt | tgtctgtgag | aaatacttcc | ccccgccccc | tcacttctta | ggcttatttc | 54480 |
| tcttgttatc | tgtttctttt | ttcttctcta | ggcactgcct | tattactgct | tcatttgttt | 54540 |
| gcaatattaa | tgtctgctaa | aatgtcttaa | gatatacaat | gttaattcat | ttgctcaatg | 54600 |
| atttaaaaat | atttgtgagt | ctctcactcc | tccacatgta | catataccttt | ggaggtagga | 54660 |
| caaaggtgcc | ttaaatattc | attgtacttt | caggtttata | cagtttgggt | tgggagttat | 54720 |
| actttcacaa | actgtggtac | aaaaataaaa | agtgatggct | tctataaaag | gtaatgatga | 54780 |
| aatgctatga | ggcattttct | catgtgcttt | ttggtcattt | tgtgtgtgcg | tatatatata | 54840 |
| ttcctttgtg | aagtgcctgt | tcaaatctct | tgcccataat | tttccactgg | attaaaaaa | 54900 |
| ttgcattata | gaaattgtta | catagtctag | gtacaagtcc | tttgcatgta | tatattat | 54960 |
| gtacatacat | gtggctttta | aacctatttt | cttacgattt | taatttctgt | gaagtctact | 55020 |
| atatctttat | gcttttcctt | taatagtgag | tgctttctgt | gtcttgtaaa | aggaattttt | 55080 |
| tgttattctt | aagtcactaa | gatatatgcc | tgtgttttct | ttgatgtcta | ggtctacata | 55140 |
| ataaatcatt | agagaaatgt | gaattaaaac | caatgagtta | ttactacaga | gtcactagaa | 55200 |
| tggctacaac | taaagactg | acaatactaa | gtgttgttga | ggatgtgaaa | caagtggaat | 55260 |
| caccatacac | tgataatgag | agtataaaat | gacaaaacga | cctaggaatt | agtctggcaa | 55320 |

```
tttctcatgt aaacatacac ctgtcctacg actcaccatt tatgctttta ggttttacta    55380
aaaagaagtg aagacatgtg tcaacaaaaa gatttgtaca agaatgttta aagcatcctt    55440
attcataata gccagtcact ccaatgtcca tcaataaaac agtagataaa caaactttgg    55500
tttattcata taatagaata ttacttggca ataaatatat acaaattact gatatacata    55560
aataatataa attattctca aaatgctgag ctaaagaagt tttccacaaa agagtatatg    55620
ctatatgatt tcatttatat gaagggccag aataggtaaa actcacctgt gatgaaataa    55680
agcagtggtt ctgtggtctg aatgtttgtg tctctctcaa attcatatgt tgaatctact    55740
taccagtgtg atgacattag gaggtgggga ctttgggagg tgattaggtc agcaggacag    55800
agccctcata attgggattt actgcccttta atcccaatta aaagtttcca gaaatctctc    55860
ttgctccttc caccaagtga aaaaacagc aagaaggcac tatctataaa tcagaaaaca    55920
ggccctcacc agacattgaa tgtgctagtg ccttgatctt ggactttcca ccctccaaag    55980
ctgtgagaaa taaatgttgt ttataagtca ttcaatttgt aatattttgt tagggcagtg    56040
ttatgctgac tgtaacaagc ggggattgac tggaacaaac aaggaggaaa tgtgcttgag    56100
caatggaaat gttatatata tagataggag tgtgagttat acaacagttt atcttcatca    56160
acactggggg aatgcacatt taagatttga gcatttcatt gtatgcaaat aatacctcct    56220
taaaacaatg aaaagttct agagggcaga ttttgcaatt aattgattag aaatatggca    56280
tattggttta catattgggt tatactcaga gtctcaaacc atagttctga aacttattag    56340
ctggcaaagt ctggtaagta acataacctc cctgaacttg ttttcccttt gcacagctag    56400
aataatacct tctttaagag atgttatagg aatgtatgta aaaggcttat cacaagggct    56460
gacataagaa attactttat tgactaattc tcctcctttt tgtccttctt cttgtttatt    56520
acttagtaaa gtgtcaaata tggctgtcag gttttggttg ctgctgtttg tgaagatgat    56580
aaattgttaa cagaaataca gagcacacta gtaagatcat acctgggaga gaataatgag    56640
tcatctaatg aatttgagac aaataggat gtcctgaatg tagtgtcaat aatgggtctt    56700
gaatttggga gagaaatcag aaaaggagct ttggatctga ggtgtgctga acagatacac    56760
cagatctctg gggatgggaa gggtctggaa aggtgtgact tgtagtattt gctggtttcc    56820
atgctgtaaa tactgtgtca tgaccaattt aaagttacca aaccagattg caaaattcct    56880
gaatgtttat cagtcagctc ttttcagctg gtgactgcca cctccagcaa actgctagat    56940
ctgagtcatc tgctgagaca gagaatgaga agatacaat tattttctca ccttacacca    57000
ggtcttcttg cttgcaggat acattgagtt taattaaatt attttgctat gaatccccat    57060
ttctgaatgt ctctctacag ctcacgctat tttcagttat gtatgaaaaa cactttatct    57120
tcttgtgccc actaccttca aagagggcct ccttttttata atacagaggc cacccagggg    57180
ccactaggcc tcagtctggg agagattcaa gcacagcctc acactgtgaa aaagagcaac    57240
tcttcccttc ttttcctcag tgctaggctt ctgcctcact taagaaaata tttcattctc    57300
tccttgctgg gaaagacagg gacactttca aatctagttc attatctcct acctcccatt    57360 cctcccctg tccagttcat aagtctgtct gcatgaaccg caagtgtaga cagagttgtt    57420
ttcatgagct ggaggaatac tgacaaacca tggaatgggg tttaaaactt tatgtaatgt    57480
catagagctg tctatagcaa taagagtact tttgttaaga gtacaagaag actcttctta    57540
acttacaggc aaactaaaca ctctgttaaa attacatttc cagaagttct ttgtcctaaa    57600
aataacagga atgtaaagaa ttttttgccc agggatgttt cttttcaata ttactttta    57660 tagcaaaata aaatgaaaaa caaacaatca acagaactat acgcccatgt ttccatggta    57720
```

```
aaatgtgaca tactcattaa aaataacatt atgtagtcct taagatgatt atgattgtta   57780
ttattatttt taagacagaa tctcactccg ttgcccaggc tggagtgcag tggcatgatc   57840
ttggctctct gcagcctctg cctcccatgt tcaagtaatt ctcctgcctc agcctcctga   57900
gtggctggga ctacaggcac gtgccaccac gcccggctaa ttttttctat ttttagtaga   57960
gacggggttt caccgtgtta gccaggttgg cctcgatctc ctgacctcgt gatccgcctg   58020
cctcggcctc cgaaagtgct gaaattacag gcatgagcca ctgcgcctgg ccttccttaa   58080
gattatcaat gaaaaagtt ttattctcat gaaacatgtt tatactatac tttagtatgg   58140
catttaccat tttaactgtt aaaaatatga aagaggaat gattggaaat gagttttca    58200 gactgttaag tcactattat taccgtgaat ttttcttttg gtagtgggat tttgggtggt   58260
ttcttcctcc ttctctgtgc acttaagtgc ttttccaaat tttctataca acaagcaaaa   58320
aatatctttc aataaattcc cgatgccccc agagaccaca tttatattcc accatctttt   58380
gtttatctat tccggttttt ttttaaattc aaaacccatt tgaagtctat agtcaaatta   58440
tttttataac acatatagga caaatgtcta gtagcataaa aatgggctcc tttagctatg   58500
atgtacagtg gtgtcacctc tctggttatt ttctcttgtg cttcaataaa gaaggctagt   58560
ttaaaaaata agaacctaag ctttcctcac tgcaaagtac ctttaacttg ttggcaattc   58620
aatcttcaaa cccctttaaa tatgtatgta tatctatatc tgagttatac gtttcaaca   58680 ttttattatg aaaaatttca aacacacaga aaagctaaaa aatggtacag tttatactac   58740
taatagacct atcagctaga ttctataatt aacattttag tatctttgct ttctcacata   58800
tctatttacc cttccatcaa tccatcttat tttttgatac atttcaaagt aagtagcaga   58860
cacgagtatg ctttgctcct aaatactctt ccacgcatgt ctttaactga aagagttcga   58920
tgtttttcgc ttttttttct tgctttgggg gtaaaattta tgtgcaatgg aatgttgaaa   58980
tctttagtta ccagtcagtg agttttgaca aatgtgtgtg tctgtgtcac ctaaactctt   59040
gtcaaaatat agaacatcac cataatacgg gataatttct tcatgtttct tctaagtccc   59100
tgaactgccc atcccagagc caaccattgt cctgatttga ttctacaatg taatgttttt   59160
ccaaggctag aactgcatat caatggaatc atacagcatg cagtcttttg tgctattttc   59220
attcagcata atgtctctgc tgttcatccg tgttgttttg tttttagtc attttctttt    59280 tgttgccgag ttatctccca ctgtataaga gattgtttag gtatccattt tcctgttgat   59340
ggatacctag attattccac cttttagtac tatgaacaac cttgtacgac tcttttttgta  59400 ggcatctgtt tcattgctc ttgggaaaaa acctaggagt agaattgctg gatcagaagg    59460
tagatgtgta tctgggtgtt tttttaaaag aaacttctca aacttttttcc agagaggctt  59520 atcatcttac actccaatcc acaattcata ggagtcctat ttttctctat attctcggca   59580
atacttggca ttgtcaatcc tttttttttt taatttagct ttattatgtg tgtgtagtac   59640
ctgaattgta tctttactg tatatattta aagtatatga attgtatttt taaaatgttg    59700
aaatgtttgg tcaatttctt tgctgtctaa aggaggaaaa ggcaagagag acaagttttg   59760
ctctaacaaa cctagacttc ctgagtccac agcacattga aattggcaca atcctagtat   59820
tttgtaagaa tccattttc tcccatgaag aactttgttt tcccaagatt taaatggtaa    59880
ttactatagg ctcacttcac cattatcata atcatgattg ctggtccctc ctcctaagtc   59940
cttctctttt gtttcttcac ttctcaattc attaagacta cttgtaagga ttatggagtt   60000
gcttcataca ttcctggcat ctttgtcagg taatttcctc tgtctcatgt gttcttaggc   60060
```

```
tgtaggcatt tgtgtccatg tctgattctt ttcttaatct ataaaaattt tgaagaaagg    60120
aaacatctaa tttaccttag cacagccact tgcacctagt aggtgctgac taaacattta    60180
ttgaagagat gatggagtag tgaagaacac aaaccctagg gctagactct tccacctacc    60240
agctgtgtga tatcaagcat gttacttacc ctctctaagc ctcagtttcc atctgaataa    60300
tgaagataat aagagtacct accttactga agttttgtgg ggattaatga gctaattttt    60360
aaaaagcctt tagaagaatg cctaacatac tatgaatata tacaaataaa atgaaaccaa    60420
atcatctttg gatcatatat caatttata gaaaactctg gctttctaaa tcaatgtcta    60480
ccctatttgg aaattttct taaaaacaac aacaagcaaa aagcaataat tcaatctaaa    60540
gctatttctt tcaagtattc tagttctgtt attccagaat ttggtgaatg aatctattta    60600
tccattatga ttttgtagcc tttgatcata tgcctctcat tctccagatt ttcagaggaa    60660
gcatgtctgt aataccttt ctttttttct tatttagggt ctttattat gtcttccttg     60720 aagtgctctg atcagatctg caatactgga gatgtaaatt caactctact tttttttct    60780 tttaaaaga agagcaacat aatccttagt gatcctaaat attattcaac ttatcttaac    60840
attcaatttc tttatatagc aaaggaatgc attttagca atgaaataaa cagcaaacat     60900
tgacattgct tattaacagt atttacggtc gaagtgcccc acatattctg aaaggttatg    60960
ttgtacattc ttttaagaag acttcagggt tttctactga agaatttga aaatcaagac     61020 ttggaagggt cctgagagca acattctata gaggaaaagg ctaaaagta ccccaggatc     61080 ttcagtagca gtgatagtat ggctttgttt tccttcactg gactaggctc cataactaag    61140
cgtcttatat ttggaagtca aaatgcattt gtttgtcttc ttacaacata gagaacacat    61200
gcttacaaaa tcaaggaga gcattgacta ttgtgacctg tttaacatat ttctccgctt     61260
tgcttcggat gagagatttc aaatctcatc attaatgtgg tgaaaatat tgaattggaa     61320 aacactaaca ttgtcttccc atattgagtc attgtctgtt tgtaacttcc aaacaagaaa    61380
aagatattaa tggtcacctt ggctgttcc ttgtgacctc caacatggct cgcatttaaa     61440
attgaatctg gactggggtg tctggggta gggagtggaa atctacaggg tgcagaataa    61500
aggctagatg tgtccacttg gtattaagga aatgcttctg caagcacaaa aagaaacaat    61560
atttggtaaa aatgaatgtt gtttccct gctccggcat ctgcttgcgt ttacaatggc      61620
cgcagtgttt ttcttacct ggtaggtggc ctctccatgt atcgatgagg cactgcgtga     61680
aaatgtgcct ccttatgtcg gagggaaatt tgctttcact tcttttccct gctctcctgt    61740
gcctcccttt gttctaatca tacatgtgag gagaaaagcc agtgatatca gcaatcattt    61800
tcttctccag ccacttttg gagttaataa ttcaaacaga tcttttacaa actcattta     61860 ttcttagaaa tggccttatt gctaacagtc tgctctccag ttgtactta tcaagcagca     61920 gatctgttgt aaaatgtgat gactggattt catctgtttt gccacccct aagaattcat     61980 tgcccacagt gcttcaactg ctgttataag agacagttta atttttgtgg tacattgatt    62040
gataactggg ctccctggta acatggtctt ccttgaatag gactgctgtt ttctaggtct    62100
cagatcccct gaagatgcta cataactccc tgtatgaaac aaatcttcca caccctaata    62160
gtaatatacc aaatccccaa atgaacgaaa atacacaca aatgcctata ggtatcttca     62220
tgcctgtagg tgatataata tgggaaggga agttcccctc ggccttaggt gtgatgaaat    62280
cagcgaagca gaaaaacag agaaacaacc aagcaaccaa ccaaacagaa ctggaagact    62340
tgtcacaatt ctgaaaagtt gtctaaactg gtctatactg agtaataaag ttgcaggtac    62400
ttctttactc cttgactaat tttctgtagc tctcaggtga accatgtagg atacctgcta    62460
```

```
tgtatcttca aattaaaaaa taatagtaat aataacaaca aaagagaggg caaaaatagt   62520
tggcaaaaag gagaattgta aaagatcata aaaacaaggg gtagaaggat tgggtaaaga   62580
gatttgaatc tccaagttat gggagcaatc ttatcatcag tatatgaaaa aacaatttt    62640 aaacaaaact ctcattattc ttttcactat atcgaggcca aaaacttcat gtttacacac   62700
acttcaaaga agaggacaat gatgtaggtc ctaataaaac cattactact ggttagtaaa   62760
tttgctaagc ctactgcatg gaagaaagtt gagggcttgg ttaaaacctt agcagataat   62820
ttagcacaaa ataagttctt aggagcctaa catgcctgat gattttggtg aaatctgttt   62880
cttcccaacc atgtacatcc aatgactgat gcatttggtg gcaatgttaa gttggatggt   62940
cacaagttct aatctgatat cccatgttgc ttcattaatg attggtccgg tcccctggtg   63000
accactcctg tatccatttc cagagcaact cttactctgc ctactttctt tttgcttgag   63060
ttaaatgcga tggttagata aaactatctc tgtattgaat gttattcatt caacaaatat   63120
ttattgagat actataatgc ttcaggcact aggagctgga attcagtaat gaacaagaca   63180
gaaaaaaatt tctgccttcc tggaccttgg actctagtga gtgagaggaa taataaacaa   63240
aatacgtaaa caaagtaaat gaaattagat gaaatgaatt agtggctcac gcttgtaacc   63300
ccagcacttt gggaggctga ggtgggtgaa tcgcttgagt gcaggagttc cagactagcc   63360
tgggtaacat agtgaaacac tatctctatg aaaataaaa aaattagccg ggcacggtgg   63420
cgcatgcctg tagacccagc aacttgggcg actgaggtgg gagaattgct tgctgctggg   63480
aggcagaagt tgcagtgagc taagatcctg ccactgcact tcagcctggg tgacagagcc   63540
agatcccgtc tcaaaaaaaa aaaaaaaaa aagataaggg ctaatagtcc agaaggagg    63600 gtaggaagga aagttttaga cagagtagcc aagggtggtc tcattgataa ggtgattttg   63660
atgaaagacc taaagagagt tggggaagtg gccatgcaga tatctggtgg attagcaatc   63720
cagacagaat agcaagtgca aaggctgtgg ggctgggaca tgcccgacat ttttgtgggg   63780
aaagctaaag aggctgggat tactgaagta gagtaaatga gggagagagt tataaatgat   63840
gtcacggagg taatgaagac caggccacgt aggatcttac aagccatgaa aggaacattg   63900
gcttttgctc tgagtcccat aggaagccat tggagctttt tgtgcacaaa acactggagg   63960
gttttgtgca gaataatgaa tgttatgttg actgagaata gatgaaaaga gtgcaagggt   64020
gaatggtggg agatcagtta gaaggctaca gaagttattc agagaggata ggatcagggt   64080
gacggtagca ggggtggtag gtagtcatgt tctggataca tctttgtggt agaaacgata   64140
gcatttgatg atgcctgtta gagtaagagt agagttatgg ctacaaccaa aatatgaatc   64200
taagtaactg gtagaattga gattcaatga attgaggtgg ggaagactgg aggaggtttt   64260
tttgtggcat gtgtatgtaa agacactgat tttggacatg ctaagagtaa gatgtctatt   64320
agatattcaa gtggaggtag caagtaagca cttgaatata taagtctgta gttgaggaaa   64380
gaggcaaagt tggagataga aatttgagta tcatcagcat atagatggta tttaaagcca   64440
tgagattaga tgagatccct tagaacacct ctgagagaag gcatctatga actgaacctt   64500
ggagttcagg gagatgagga gaaactagcc aatgaagctg agaaggagtg gccaaaaaga   64560
gtactggctg ggcatggtgg ctcacatctg taatcctagc actttgggag gccgaggcag   64620
gcggatcacg aggtcaggag tttgagacca gcctggccaa tatggtgaca ccttgtctct   64680
attaaaaata caaaaattag ccgggagtgg tggcgtgtgc ctgtagtgcc agctactctg   64740
gaggcgaagg cagaagaatc gcttgaaccc aggaggcaga ggttgcaagt gagccgagat   64800
```

```
tgcaccactg cactccagcc tgggcgacaa tgcgagactc tatctcaaaa ataaataaat    64860
aaataaaaag agtaccatgt cctagaagaa aagtgaaaaa catgtttcaa ggcagataca    64920
gtgattgatt gctgaaaggt cacatgtcgc tgaaaggaca aataagatgg gaatcattga   64980
atggaattta gtgaccacat ttaacaatat agagttgatc agtgaccttc agaataactt    65040
cagaatatct gttgagcaca agtctgaagt aacccaaaac agcttatcaa cctctatgga    65100
ttaaataaaa caatgtgctc ctgtgtaagt aacttgtttg aaagcaagct ggagtgaggg    65160
agctagatat tgagagttct aagttcctta ccatcacctt cttgcacact aaagtattga    65220
aagaatgtaa tattcaaaac aggcaagcaa acaaacaaat agaacatcat ctgaatagat    65280
tatatgtaac agtcttcaat ggaaaccatg acaacaggga aaagaggcct tgtaaaaaaa    65340
ttgtgtgtgt gcttctgctc tgcttttctca atgtatttat catgtcatgg ccttggcaag    65400
aacaagaggt agagataaat aaataactga tttctcatct tttggaaaaa aacaaaactg    65460
gcctaatgta aatggataaa agtcctctct gtagttgtca atttaaacgt aaagccccaa    65520
tttaaaaaaa aagtgaatgg tgttgcagtt gtgtgggtgg atttggtagg gagtttaatt    65580
ttgctacaga gtggagttta atctttgcta aagaaaagta tatcccttg atttttttag     65640 aatgcccccaa ggtccgtctg atttaaacta gtattggaaa aagggaagag agatggaagg   65700
gagtgatcaa agttggaaaa cgatagaact tcccccatg aaacacaaga aaggtgaata    65760
caggtgaaaa ataagatag tgctgctcca catgtttgga attgcatttt tggtagtctc     65820
aactaaccga aatgcagcca cttagagaag gctgtcacga agcttatgta gtataggata    65880
ggtgtgggac tgcccctcag ggcagagggg aacattaaac atactgattc ctgttggtta   65940
tttgatttcc tctttgaggt tagtgacaga aaacttactt tttaatttgt gacctatcta    66000
ggagtggggt acaaaggaga gaatagaaac aaagagataa tccatgagaa gaacaatata    66060
cttaagtccc ttaatgaccc cattgggagt gatgtggttg gcttgatact gatgttcaat    66120
agacacctcc ccctcccatc ttcagtcgtc tttagctcta aaatctctgt ggtcgaactt    66180
ttgagatagg ctgatgtgcc accacatatg ccatgaccca agggactggc tggcaattac    66240
tctggatgct tcttgaaggt tcttcattgt tcttgcccct aacctgcctc tgtaggatct    66300
caacttttct cttcccgctc cagctgcact atgtatccgt gcttggctct cagttgttgg    66360
attctcatgt ctccttttc acagtggctc aggtaagggg acttgttgca acatctcgag    66420
atgctgtctt tagtcctagc tctcttggaa gagaggaaag gagatgagac atactgaaac    66480
cacattttct tgatgttgag cagaatccag ttcacagact agaaaatgtt ttattccttg    66540
taggctcagc agtacagaaa caaggtgggg aaaggaaaac aatttctaaa gagtgaatta    66600
ttatgaatta tcttataaat gcccatgcca cctgctttac ttctcataat tcactaaacc    66660
tcctttactt ctcataattc actaaattca ctatgctctg catttcatct gtggtgtgat    66720
gagttaaaat tgccttgttg ggaattttt cagaacattt gtccacttga acaaaaatca     66780
atattctgtc tcttaaacag aagcatttga acaagttgca ctatgcggag gtgagaacaa    66840
taattatatt ggtacatgtc ttaaaaatta cccagaagca gatgagaatt tgtgaataaa    66900
tgactcatta agaaagtgtc cccagaagaa gtcagtaagt gagtggggc atgaggagag     66960 gaaaagggaa gtcaagcaaa gtgtgctatt tttggccaag tcttatagta gggagctttg    67020
gcctaaatct acaagggaaa cttagagcat aaattgagtt gtctgccata aatcaactgg    67080
gaggaactta ggttttcata cacttgcatt atcagtcata gctaagaaca cccaagggcc    67140
atgtaaactc ccaattactt ctctcacagc cataggtaa tcctctaaaa acagacaaat      67200
```

```
ggacaggcca ttggaaataa gagtcctgga cctaggaaga aattcaggaa acagtaaagg   67260
aattcaggga aacctaggtg ggtcactgca gtgactacta catcatttta agcatttatt   67320
gagcgtttgg tggtgcctag aaagctgtgt gtgtgtgagt gtgtgtagaa agctatttag   67380
ttctcacaat acccttagaa ttatctctgt tttacatact aaggaactaa agtgttcagt   67440
aatttggaag agtgtttaaa aaaggtctg caatagagcc aagattcaaa tcctggtctg    67500
tctgaaggcc atgtccacag tcacgttatt ctctccttat tatactacct cctggtcagc   67560 ctcctaaccca aagtaagagg tgaagtgcag aaaggatagg agaacttggg atagggtaaa  67620
cagaagaaaa aaaaaagcag agatgataaa atagtttgta actaagaaat gttatagcaa   67680
atgagtgggg attattctat ggccaagaga agggaagact gaggaaactt actaatgatc   67740
ttcaagttca tgaaagggtt taacacagaa tagattggcc agctgtgctc aaatttctac   67800
atagtgaatt taaaagaaa actatttgct gttatagcac gaggatttta ggctggattg     67860
aagaaagtgt tctctgggca aagggctat tgagcactag agtgaaatcc tataaactca    67920
aattagaaag aaaagaaaac agaaagaaaa agagaaaaat aaaagaaaag aaaagaaaag   67980
atgtgagcac agtctgtcat gctgtgcaaa tgtatgagat gttaccttga acacagctgc   68040
ttcacacctg caaccttcca cagagggaga gccgtgaatt aaaaaaataa agcagcgaac   68100
ttcattgtag ctgaggatgc caggaaacct gatggccttc tagaaactat catattaatt   68160
gttgtattag ggcagaaaca tgtactggtc tggtttagta gtttgcttct taatgcgaac   68220 tctcttttc acttttgtcc tttctccccc aaagacaaac atttccaaga cattatgtat    68280
atgtaaaaga gcatttatg tagaagtaca agaaataaca tttggtgatg caacaatgtg     68340
gcacagagtc aatgactgtt tagatagcaa acggaatgga ctttgacggt accttgtgaa   68400
gtggcacata tcattgaata atctattgtt ttgatgtcct ctatgcaccc atagaccctg   68460
cccctgaaaa ttttctgcat aaccaattta gatttatgta tatatatata cacacacaca   68520
tatatacaca catatctcta tatatataca cacatacata tagatatata tacataaaca   68580
ctctcaatga tgtgttgaga tggtatgtac tgcagccaga ctttaaacta gctcattatt   68640
ttataatggg gtgtatacta aaaatttatt ttgaagtcac ttacaaatgt gtttccca     68700 tcaacattct gctgtagatg tcattatttg ggggcagaat atcactgtaa tcacaccaaa   68760
tttacctgtg aagttactat ttttccagcta cactgtagac taaattaata gttctgagtt  68820
actggagaaa ctcgatcacc agatcactat ttctctggaa aaaatgaat tccattttga     68880 atttggaact ccagaaatat ttccatccta atgtgcctct cagtagaggt ttgtcagagg   68940
gttttccaca cattgggtaa agccaattgt caaaagtcaa atgttccctg aaattgcttt   69000
tcctttaacc agagtggtga cttgtgctct gtgaaagaga attttccttc cttccatttt   69060
aatagcaggc tttcatagga ttgaagaatt tgtacaagag caacaattat tattagcacc   69120
tactatgtat tggacactat attattcatt gtatatatat tatcttatgt agcctccata   69180
acaaccttgg gatgttatat tattatcacc attctacaga agaggaaata gatgtaaaga   69240
agtcagcttg ctggaagtcc tataaataat aaatgataga attgggttgt gctgtggttt   69300
gaatgtctcc tcccaaatta atgttaaaat ttaattgcca ttgtaacagt attaagaggt   69360
aggactggta agaggtagat taggccatga gagcttcacc ctcatgaatg gattaatcca   69420
gctttcacag gagtgagatc attataaaag gccaaatttg gtcctctttg tcgcttgccc   69480
tctcttgccc ttctgccttc caccatggga taatgccaca agaaggccct aatcagatgc   69540
```

-continued

```
cagctcctca atcttggact tagcctatgg aactgtgata atatttttt ctctttagaa    69600
attactcaga tactggtatt ttgttatagc agcacaaaac aatctaagac aggttgtgaa    69660
ctctggactg actgacccta aattcaagag ccttttcatg gatgttgtgg tggacgtttg    69720
ttggttgtgt gcctgacatc cattctccct taccattatt ttcctttgga aaattttacc    69780
ttcactacct gtcccccata ccacaccaca tcacagacat ttagtttgta tggaattgac    69840
cccactgcct gtcttaggag tgagcccaga ttgacttagg ccaaccacta tattatattc    69900
ctctccctca tttccccctc ccatactgcc tggctcagag ataagtaggt agctcaatca    69960
gagccaatga gatagaagga gatatttcct tgtcaccttg gaaggagaag ctcccttctt    70020
taactgtgtt gcaaaagaat gtgagttctg aagtggtgga acatttttt tacctatagg    70080
agacagcctg tttctggtgt ggcaaccact gtgtagagcc ttagtttgaa gccactgggg    70140
cagaagacag agggaatcca gggtcaaaac aacaactttt ggactcctgg gtcaacccct    70200
atctgaagta agagcggctt ctgggctcaa ttgtaaacat atttgctcaa acaacaactt    70260
gtagtttgag ccacgttatg ggggttcgtgt caatttcaac ataaagagtt gtaagtaaca    70320
caggcactcc ccaggactat tccttcatta aaaacattta catcttccaa atctctggta    70380
tgatgagact tgacttccac aatcacactc ctgaaacaat tcagcaacct aattaatcaa    70440
ataagattac attcaggcta ttctccttgc taagtgaaaa aacttgccca cttaaaattt    70500
acgaagattc tgagcaatac agaataaaaa caaagaatgt tttggttaat gattttaagg    70560
taggcagaaa aaaactaatt aaacgatgcc tttttctgat aattctagtt aattggagtt    70620
ttaattccag taggaataat aaaaactggg gtctaagttt ggtaagtaaa gttttcaaat    70680
tattatatt tgcttaattt agaaaaatgt atgtacacat tcatttccct gtgagacatt    70740
aaaatatatg aacatagatt aagcaaaata tattttcctt tattgtgata attccttgtt    70800
atctccagtc tttccccccaa atgtgataag aatacatagc tacagaggga ggagccaaga    70860
tggccgaata ggaacagctc cagtctacag ctcccagcct gagggacgca gaagatgggt    70920
gatttctgca tttccatctg aggtaccggg ttcatctcac tagggagtga cagacagtgg    70980
gcgcaggtca gtgggtgcgc acactgtgct cgagccgaag cagggtgagg cattgcctca    71040
ctcgagaagc gcaaggggtc agggagttcc cttttcctaat caaagaaagg ggtgacggat    71100
ggcacctgga aaatcgggtc actcccaccg gaatactgcg cttttccgat gggcttaaaa    71160
aacggcgcat cacaagatta tatccctcac ctggcttgga gggtcctacc ccacggagtc    71220
tcgctgattg ctagcacagc agtctgagat caaactgcaa ggtggcagcg aggctggggg    71280
aggggcgcct gccattgccc aggcttgctt aggtaaacaa agcagcgggg aagctcgaac    71340
tgggtggagc ccaccacagc tcaaggaggc ctgcctgcct ctgtaggctc cacctctggg    71400
ggcagggcac agacaaacaa aaagacagca gtaacctctg cagacttaaa tgtccctgtc    71460
tgacagcttt caaaagagca ggggttctcc cagtaggcag ctggagatct gagaatgggc    71520
agactgcctc ctcaagtggg tccctgaccc ctgaccccg agcagcctaa ctgggaggca    71580
ccctccagca ggggcacact gacatctcac actgcagggt actccaacag acctgcagct    71640
gagggtcctg tctgttagaa ggaaaactaa caaacagaaa ggacatccac accaaaaacc    71700
catctgtaca tcaccatcat caaagaccaa agtagataa aaccacaaag atggggaaaa    71760
aacagaacag aaaaactgga aactctaaaa agcagagcac ctctcctcct ccaaaggaac    71820
acagctcctc accagcaaca gaacaaagct ggacagagaa tgactttgac gagctgagag    71880
aagaaggctt cagacgatca aattactctg agctacagga ggacattcaa accaaaggca    71940
```

```
aagaagttga aaactttgaa aaaaatttag aagaatgtat aactagaata accaatacag    72000
agaagtgctt aaaggagctg atggagctga aaaccaaggc tcgagaacta cgtgaagaat    72060
gcagaagcct caggagccga tgcgatcaac tggaagaaaa ggtatcagcg atggaagatg    72120
aaatgaatga aatgaaacga gaaggaaagt ttagagaaaa aagaataaaa agaaacgagc    72180
aaagcctcca agaaatatgg gactatgtga aaagaccaaa tctacgtctg attggtgtac    72240
ctgaaagtga tggggagaat ggaaccaagt tggaaaacac tctgcaggat attatccagg    72300
agaatttccc caatctagca aggcaggcca acgttcagat tcaggaaata cagagaacgc    72360
cacaaagata ctcctcgaga agagcaactc caagacacat aatcgtcaga ttcaccaaag    72420
ttgaaatgaa ggaaaaaatg ttaagggcag ccagagagaa aggtcgggtt accctcaaag    72480
ggaagcccat cagactaaca gcggatctct cggcagaaac cctacaagcc agaagagagt    72540
ggggaccaat attcaacatt cttaaagaaa agaattttca acccagaatt tcatatccag    72600
ccaaactaag cttcataagt gaaggagaaa taaaatactt tacagacaag caaatgctga    72660
gagattttgt caccaccagg cctgccctag aagagctcct gaaggaagcg ctaaacatgg    72720
aaaggaacaa ccggtacgag ccgctgcaaa atcatgccaa aatgtaaaga ccatcgagac    72780
taggaagaaa ctgcatcaac taacgagcaa aatcaccagc taacatcata atgacaggat    72840
caaattcaca cataacacta ttaactttaa atgtaaatgg actaaatgct ccaattaaaa    72900
gacacagact ggcaaattgg ataaagagtc aagacccatc agtgtgctgt attcaggaaa    72960
cccatctcac gtgcagagac acacataggc tcaaaataaa gggatggagg aaggtctacc    73020
aagcaaatgg aaaacaaaaa aaggcagggg ttgcaatcct agtctctgat aaaacagact    73080
ttaaaccaac aaagatcaaa agagacaaag aaggccatta cataatggta aagggatcaa    73140
ttcaacaaga agagctaact atcctaaata tatatgcacc caatacagga gcacccagat    73200
tcataaagca agtcctgagt gacctacaaa gagacttaga ctcccacaca ttaataatgg    73260
gagactttaa caccccactg tcaacattag acagatcaac gagacagaaa gtcaacaagg    73320
atacccagga attgaactca gctctgcacc aagcggacct aatagacatc tacagaactc    73380 tccacccaa atcaacagaa tatcatttt tttcagcacc acaccacacc tattccaaaa    73440
ttgaccacat acttggaagt aaagctctcc tcagcaaatg taaaagaaca gaaattataa    73500 aaactatct ctcagaccac agtgcagtca aactagaact caggattaag aatctcactc    73560
aaaaccgctc aactacatgg aaactgaaaa acctgctcct gaatgactac tgggtacata    73620
acgaaatgaa ggcagaaatg aagatgttct ttgaaaccaa cgagaacaaa gacacaacat    73680
accagaatct ctgggacgca ttcaaagcag tgtgtagagg gaaatttata gcactaaatg    73740
cccacaagag aaagcaggaa agatccaaaa ttgacaccct aacatcacaa ttaaaagaac    73800
tagagaagca agagcaaaca cattcaaaag ctagcagaag gcaagaaata actaaaatca    73860
gagcagaact gaaggaaata gagacacaga aaacccttca aaaattaat gaatccagga    73920 gctggttttt ttgaaaggat caacaaaatt gatagaccgc cagcaagact aataaagaaa    73980
aaaagagaga agaatcaaat agactcaata aaaaatgata aaggggatat caccaccgat    74040
cccacagaaa tacaaactac catcagagaa tactacaaac acctctacgc aaataaacta    74100
gaaaatgtag aagaaatgga taaattcctt gacacataca ctctcccaag actaaaccag    74160
gaagaagttg aatctctgaa tagaccaata acaggatctg aaactgtggc aataatcaat    74220
agcttaccaa ccaaaaagag tccaggacca gatggattca cagccgaatt ctaccagagg    74280
```

```
tacaaggagg agctggtacc attccttctg aaactattcc aatcaataga aaagaggga    74340 atcctcccta actcatttta tgaggccagc atcattctga taccaaagcc gggcagagac    74400
acaaccaaaa aagagaattt tagaccaata tccttgatga acattgatgc aaaaatcctc    74460
aataaaatac tggcaaaccg aatccagcac catatcaaaa agcttatcca ccatgatcaa    74520
gtgggcttca tccctgggat gcaaggctgg ttcaatatac acaaatcaat aaacgtaatc    74580
cagcatataa acagagccaa agacaaaaac catatgatta tctcaataga cgcagaaaag    74640
gcctttgaca aaattcaaca actcttcatg ctaaaaactc tcaataaatt aggtattgat    74700
gggacatatt tcaaaataat aagagctatc tatgacaaac ccacagccag tatcatactg    74760
aatgggcaaa aactggaagc attccctttg aaaacgggca gaaggcaggg atgccctctc    74820
tcaccactcc tattcaacat agtgttggaa gttctggcca gggcaattag ggaggagaag    74880
gaaataaagg gtattcaatt aggaaaagag gaagtcaaat tgtccctgtt tttagatgac    74940
atgattgtat atctagaaaa ccccattgtc tcagcccaaa atctccttaa gctgataagc    75000
aacttcaggg gtgatcagcc agccacctgg tggcaggttg attatattgg acttcttcca    75060
ttatggaaag tgcagaagtt tgtccttact ggaatataca cttactccag atataagttt    75120
gcctatcctg catgcagtgc ttctgccaag actaccatct gtggactcac gtaatgcctt    75180
atcaagtgtc atggtattcc acacagcgtt gcctctgacc aaggcactca ctttacggct    75240
aaagaagtgt gtcagtaggc tcatgctcat ggaattcgct ggtcttccca tgttccacat    75300
catcctgaag aagacggatt gatagaatgt tagaatagct ttttgaagtc acagttacaa    75360
tgccaactag cgacgatac tttgcaggc tggcgcaaag ttctccagaa ggctgtatat    75420
gctctgaatc agcgtccagt gtatggtact cttctctccca tagccaggat tcgcaagtcc    75480
aggaatcgag gggtggaagt ggaagtggca cctcttgatc atcaccattc actgtcaccc    75540
ctagggatcc actagcaaca gttttgcttc ctgtccccac aacattgcat tctgctggcc    75600
tagaggtctt agttccagag ggaggaacac tgccaccagg agacacaaca gttccattaa    75660
actggaagtt agtattgcca cctggagact ttgggttcct cctacctta agtcaacagg    75720 ctaagaaagg agttacagtg ttggctgggg tgatttacct ggactatcaa gatgaaatca    75780
ttctactatt ccacaatgga ggcaaggaag agtatgcatg gaacacagga gacccattag    75840
ggcgtctctt agtattacca tgcctgtgat taaagtcaat gggaaactac aacagcccaa    75900
tccaggcagg actacagatg gcccagactc ttcaggaatg aagatttggg tcacaccacc    75960
aggaaaaaaa ccatgaacta ttgaggtgct tgctgaaggc aaagagaata cagaatgggt    76020
agtagaagaa ggtagtcatc aacaccagct acgactacgt gaccagttgc agaaatgagg    76080
agtgtaattg tcatgaatat ttcctcttga ttttgttaaa atgatgttta tgcatgtaca    76140
cacttgtact aagaaaaatc ttcattttct ttttccttta ttatgtgaca taagatttat    76200
tgacttccta tcagcattta agtattgtta actttaggta atagtatctg ggttgaggat    76260
tggtgcattt ctggttttat gaaggatagt tctatgaagg atagttgtat tatcttaagc    76320
ataattatga cctattaatg tgtttatttg aagagtatgt atgatctcag gagatgtgtg    76380
tgggtacaag ctgacaaaag gtggacttgt gatggttaat actgagtgtc aacttgattg    76440
gattgaagga tgcaaagtat tgatcctggg tgtctgtgag ggtgttgtca aggagatta    76500 acatttgagt cagtgaactg ggaaaggcag acccactctt aacctgggtg gcaccatct    76560 aatcagcttc cagcgaatat aaagcaggca gaaaacgtg aaaaggctag atggcccagc    76620
ctcccagcct ttctcctgtg ctggatgctt cctgacctcg aacgtcggac tccaggttct    76680
```

```
tcagttttgg aactcagact ggcttttctt gttcctcagc ctgcaaatgg cctattgtgg    76740
taccctgtga ttgtgtgagt taatacctaa taaactcccc tttatatgta tccaatgagt    76800
tctgtccctc tagagaaccc tgggtaacac aggatgttac agataaattt gctatgaata    76860
tttgtgtaca aatctttata ttgacagata ctttaatttt cttggggggaa atacttggaa   76920 gtaggttgca tggattatat gcatgtgtgt gttttgcttt ttaagaaact atcaaatggt    76980
tttccaaagt agttgaatca ttttacattt ctatcatcag tgtatgagag tttcagttgc    77040
tcaaaattct tgctaaaacc agatgcggtg tattttttt taaattagcc attctaatag     77100
gtctataatg ttatctcatt gtgattttaa cttaatggtg ttgagaatct tttcaggttt    77160
atttgccatc tatatgtttt ctttggtgaa gtgtctgttc aaatcttttg tccattgttt    77220
tcttattatt gaattttaag aattttaaat atatatatat aaatatattt tggatataag    77280
tcttaaatca gatatgtggt ttgcaaatat tttctcccaa gtatctggtt tgtcttttca    77340
ttttgctagc agtgtgtttc aaaaaataga agttttaaaa ttatgataat gtccaattta    77400
tctatatttt attttacaga ttgtgatttt ggtatcatat ctaaggaatc tttacctaat    77460
caaagttgca gaagttttct cctaaaagtt ttataggttt aagttttaca tttaggtcta    77520
tgattcatgt tgagttaatt ttatggtgca agatatagat caaagtttat tttttttct     77580 tgcatatata tatatatcca attattccag caccatttgt tgaaaagact aatctttctc    77640
tactgaattg cctttgaaac tttgtcaaaa tcatttgtct gtatatgtgt gggtctattt    77700
ctggactctc ttctgttcca tttgtctatt tgtctatctt tacaccagta ccaaactgtc    77760
ttgattattg tagcttcata ataagtgtta gttctctaaa tttgttcatc tttttttttc    77820
agagttgttt tggctattct gggtcctttg aattttata tcaatttag aatcagttaa      77880 tttctacaaa aaaccctgct agaattttaa ctgggattgg tttaaatgta tggattggtt    77940
tgggaagagt ggcttttctta gcattattga gtcttttgac taatgaacac aatataggta   78000
gaacatcact aatctgaaaa tctgaaattt gaaatgctct aaaatctgaa acttttttcgg   78060 taatgacatg atgccacaag tggaaaatta cacatctgac acctttgctt tcttatagtt    78120
caatatatac aaactttgtt ttctgaacaa aagtataaaa aattttgtgt aaaattacct    78180
ttaggctgtg tacataaggt gtatataaaa caaatgcatt ttgtctttag acttgggtcc    78240
cattcccaag atatctcatt atgcatatgc aaatattcca aatccaaaaa aatttacaat    78300
ccaaaacact tcttgtccca agcattttgg atgaggaata cacaacctgt atatctcacc    78360
atttatttcg gtgatcttta attactttca gcaatgtttt atagttattc agtgcacagg    78420
tcttttacat cttttgacac ttttattttt aattatttca tattttttgag gccattttta   78480 atggcattgt tttcaaaata ttaacttctg atggttcatt gctaatatat aaaataaaat    78540
ggatttttat atattgatct tttatcctgc aacattgctt caactcattt aataattcta    78600
gtagcttatt tcaaaaatat agattccagt ggatttttcta catgaataat tatgtcattt   78660
gtgaataaag agttttgttt atttcttttc aatctggata ccttttattt ctttttcttg    78720
ctttattgca ttgacaagaa attccaatat aatgtgaaag agaagtggtg agagtggata    78780
tcttgctttg ttcctgatct tagctattcc ttatttttt taagctatat tttcatagaa     78840
gcccttcatc aagttgagaa agttcctttt ttaaggcagt aaaattcctt tttaaagca     78900 aataaagaat gtatattgat atttgtcaaa tactttcttc tacatctatt gagatgatca    78960
tatagttaat acatttcttt tgtttcttta ttattatgga gtacattaat tgattttttg    79020
```

```
ttgttaaacc aaccttgcac acttggtcat gatgtattat cctttaacct ggtgttggat    79080
ttaatttgct caaatttcag taacaacttt ttcaacaatg atcgtgaggg atgttggcct    79140
gcagttttct tttcttgtaa tatctctatc tgttttggac atttaattct gggcttatag    79200
aatgagttga agaatgtcct ctccttttca atttttgtgca ataatttgtg tagaatggac    79260
actgtttctt ccttgaatct tggtaggat tatcaagtga agccacctgg acctccgcat    79320
ttctttgtgg gaaattgtat aactattgat ttaatttctt taatagtgga gggctattta    79380
tattacctaa tttttttctt gagttagctt tggtagtttg tatctttcaa agaatttgtc    79440
cattgtatct aagttgtaga gtttattcaa ataaggttgt atataatatt cccttagtgt    79500
cattttgata tttgtaaaat ttgccctggt ttcacttctt tcatgcctac tactgacaat    79560
ttgtatcttc cttcttttc tctgaccagt ctggctaggg atttattaat ttcatcaatt    79620
ttctcaattt tctcaagact gacatattat tttgcttttg tatgtctcaa aagtctttat    79680
tttgctatca ttttgaaat actttttttt cagtgggtat agaattctag aatagttttt    79740
ccctcccaat actttaaaga tattgcccta ctgttttta cttttgcatt gtttgtaaca    79800
gaaatttact gttacccctta tttctgtttc tgtatacata tcttttcctt ctactgctta    79860
taagatttcc tatttatcac ccatttgat acatttatt attctgtgcc ttagtattct    79920
ttcttttatg tttcttttgc ttagggtttg ctaagcttct tatatatgtg ggtttgtcat    79980
ttttatcaag tttggaaaat tttcatccat aatatcttca aatatttccc ctccattatg    80040
acttcaatta ctcatgtatt aggctgtttg agttgtccca cacctaacac tctgtccagt    80100
ttttaacagt tatgttttct atgtttcatt ttgggttgct tctatttcca tgccttcaag    80160
ttcactaatc ttttcttcct caatgtctaa tctgctgtta attctagaaa gtatatttt    80220 catcttatac attttagttt taatcattaa aagtttggtt tggatctttt tatgcttttc    80280
atgtttttac ttaactttt gaacatatgg aatacaatta taataaccat tttaatatcc    80340
ttctctgcta actctaacat ctgtggtag ttcttaatca gattcaattg attgatttat    80400
ctcctcatta tatatcatat tttcctgttt cttttgtatg tctggaaatt tttgtttgaa    80460
tgccagacat tgtaaattat gccttgtggg atgctatata tttttgtgtt cctataaata    80520
ttcttgagct ttattatagg acacagttaa gttacttgga aacagtttga tcttttctac    80580
ccttgttttt aggcattgct aggtagacca gagtagtgtt agtcatgggt taattattca    80640
ttactactga atcaagaccc ttcagaatac catactcaat gccacataaa tcttgaggtt    80700
ttccagtctt cctggtggat ggcaggcact attctcccca gtgagtgctc actaggtaca    80760
ttttgggtgg tcctttctct ggtcgtaggt agtatcttta catgaatgca tttacccata    80820
ctcagaatga gggacatttt gtagaaatct gaagttctct ctctgcacag ctctttcttt    80880
tctggtaatc tgttctgtga actcaagctg ttttggtctc ctcagaccct ccatttcatt    80940
tcctcagctc atagagtctt ctacactcca cctgggttcc cctccctgtt ctctggcctg    81000
gaaactccct taaggtagta aggtagagga atcacagagt ccacatcact tgtttcacat    81060
atctgagggc tcagtatcct gcattgcctg gtgactcagt gtcttaaaaa ctattgttca    81120 tatatttgt ttattttttt gttgtttcag gtggaagagt aaactgttcc tgtttctcca    81180
tcttgacagg aagcagaagt tctccttagc tgattttct tcttgcctta tactgggttc    81240
tttaacacca gaacaaaaat aaataaataa aagaatcttc cagaaattca tgaagagact    81300
tcaggtatgc agcataggtg tttgacaact acgtagagca gtgggccagt cttaatttgt    81360
ttcattaatc tggtaaaaaa agaaggattt gcatgaaatt cgcaattcag attgccatat    81420
```

```
tagccactaa gtcagaagac ttgagagctg agccttggag aaacaaaatc cttgacagtt   81480
gttgatgttt ttgtaatagg agacttctat tattttagca aacagaaaga ctacataaaa   81540
atgtcagaaa gaaactactt ttggagaaaa aaataggaac tgactcacta aagggaccta   81600
ttggggataa ttacccagag cctgtggtag atcaggatgg ctgatttaaa gttattgttt   81660
ttgcaaattc tgcaaaaaac aaaaaaacaa acaaagattt tttttcttg gctttagcaa     81720 tagtggaaaa atttcttcca cagctgtaat ctcatgtaaa ctgccaaagt ggatttatt     81780 ctctgagttt ctcaagcctc cttttctcta atacagagta atattggcta atgataaaac   81840
agtacaaact ataatttgaa atagtgtttc aatttcaat ttgcagtctg ggaatagatc     81900
acaagaattt tagtttgttg gtttcctgct gccgtaggtc aggaaagcct gaactttctc   81960
atccaacacc cgttcaagtc ggaggatgct gattaattca tgatggaaag gtatcaattt   82020
cacagcccag acctctacat tcttgaaatg ctcttctcat gggagacatt aaataagctt   82080
tgaattaact gtaagtaaat aaatattcaa ttatttgaat agcactatat tctgtttcat    82140
taaaaatatt tcttacttga ttttttctcac caataaaagt attcaaaaat gtttaattca   82200
atcatcatca catcaagaat tacgatatta tctccgaatt atataagtga ttttctggtc    82260
atgcacatac cagttgttct tactctatat aaatgtactt ttttgttaaa atataatcat   82320
ttagtttaaa attgagatat ccttgttact ggagaatttc aaatatattt aacaacaaca   82380
ataaaaagct taaatataaa tagcaaatgt gagtaagcat gggataattg aatggctttt   82440 tatattttg gaagtcaatt ccatcttcat agattaattc ttccaggttt taattcacat    82500
tgagttctaa tggctgacac cattttcct cctctgtatc ttcttcagaa tatggacatc     82560
ttgggttgtt gtgagaatgg agttaccaaa gttataatca gttaaacact aagcaaagtg   82620
ttatggcaaa gtgtagtcaa gtgcatttcc tgtcagatgg tcaacacctt aagtgcttga   82680
ggttgaagag aattgttttc atctctgttg ataggaagaa ccaatgatgt gatccctgga   82740
tactggcaat tgttgcccaa gaaaacctct cccctttgctg tgggactgct gggcacccaa   82800
ataatgcacc caaataattt gatagctctt gttacacagc tcttcttgga ctaaaaggcc   82860
ctcagcattc ctgtcaattt ctacactcct gaagcttcat ctggtaattc cctgacttat    82920
gcagtaccac cccactccta gagtgtcttt agaggtgttt gctttcttct taaagctatt   82980
atcctcttgt tcttcgaggg cttattctta ggggacttgg agggcttatt aagccctaag   83040
actcaatcat tagcaaccaa aaaattaact tctactctcc caaggtcagg gacagcataa   83100
tcttaaaata cagtggttag ggaaaatatt tgcataacgt attttaaaga atgcacagga    83160
agggaaggca aatatagagg aggaagatga tttaagagag tagagcagaa aatatacagc   83220
tgccacaaaa atttagaatt gcagaaccag ctaaggtag gtgtttgttc tgcttactaa     83280
taaagcatac accaaataca attatttgga agcctataat ttttttagggt aaaatttttt   83340 aggtgttctt ctagtcttac cccattattt taaagatgta aaaactggat cccaaagagg   83400
agaaatgact tggttaagct cacacagaaa ctagaatcct acatcctttg tattgtatca    83460
aatgctttta tgattaccat atgctgcctt tttaaggcct gtgatctcca gagagagatt   83520
tcagcttttt gatatgccaa actaaggaat tcttagttgg cctttttttt cttcttgagt    83580
ttgtgcttgc ttaacctaat gagtaggtaa taaccctgtg tttccgaatt tcttaaatca   83640 gacttttttgg gggatgaaat tttgttaatg attctgttaa gaataatgt cttttacact    83700 ttctcagctg aaaggcaagg ggatgcagga tggaggttag aaatacacag ctgccatagt   83760
```

```
ctaattctta tatagatatt attgagtgat taaatgatca agaaaactgc ctactgcttc    83820
tctttacttt tctgtattta gcaggaacat gaccttttct ttttgatcca taatgagaga    83880
gatgaagaga atatgagaga atatatgaga aatgaaagtg tgctaagaat ccacataatt    83940
aaacacccaa acacttagtt tatcattcaa gatccttcat gatcttgcca atctattttc    84000
ccaactatat cccatattat ctcccttttgc atacagttta atccatacac taaataactt    84060
gctattcttt aaatgctttg ttttttctacc tctgcctcta ttttcatact gctttctcta    84120
cctgacattc tctgtcccca aactgttgct attcaaattt gacttagctt gggttacctg    84180
agatatagac actgagacaa gcttttaagg ttgagtaatt tgttagagag taaaggtagg    84240
agaatgatta agtgaaagaa tgaaagaaag tttattttgg aagagcatgt tatcaagaca    84300
gctttcagtt ccaggaagca actgaagcat aatcccacag ggaaagctct tgaagcccag    84360
acaagctatt ctgccttaaa gttatcctac ccaaggggta agggagctaa gtatttatac    84420
accaacactc ttcagatatt gcttgagagc tgctcctaga gacattaatt ccagaagctt    84480
ccaacctgtt gaacaggtgg cagagtgagt ttcagcagtg agaggacacc cttaacaaag    84540
aactactggt gctaggagtt ggaagttggg ccaaagggaa acagatgcta acagggaggt    84600
aatatgagag gcactgacag catctgctac aaaactgtcc ccaaaagaaa agatgggata    84660
cagctggtta tgctgcagtt aaaaagcaac caagtattaa tggcttaata ccacaaaagt    84720 ttattttttca cttcttgtta tcaggagacc tctgtggatt ctataactca aagacccagg    84780
ctgacggctg gtggaatagc taccatctca acatggcgt gatgctgcat cagagagaaa    84840
aataagctct tgcattgaca atgaaatgtc taccctgt                            84878
```

```
<210> SEQ ID NO 5
<211> LENGTH: 573
<212> TYPE: DNA
<213> ORGANISM: Homo sapiens
<220> FEATURE:
<221> NAME/KEY: misc_feature
<222> LOCATION: (216)..(234)
<223> OTHER INFORMATION: primer target for exon 1
<220> FEATURE:
<221> NAME/KEY: misc_feature
<222> LOCATION: (302)..(304)
<223> OTHER INFORMATION: exon 2 translation start site
<220> FEATURE:
<221> NAME/KEY: misc_feature
<222> LOCATION: (349)..(369)
<223> OTHER INFORMATION: primer target for exon 2

<400> SEQUENCE: 5
```

```
ctccttctct tccttccctt ggccccgcgc gctcgctcgc tcgctcctcg cctcgctctc     60 cccttttaaac gcccacttcg tatggggaaa gaggacaact tgaagtcaag ttgcaattaa    120
cttccgcggc agccgcagct ccggcggcgg cggcggcggc aggagaggca gaagccgccg    180
cctcggaagt ccgacgccgg cgcgcccgcc cggggagccg ttcttggttt caggcccgca    240
ctcgacagcc accgccgccc ccaacgtcca tgcctgagtg atctttagac agtgactgag    300
tatggatcat ttgaacgagg caactcaggg gaaagaacat tcagaaatgt ctaacaatgt    360
gagtgatccg aagggtccac cagccaagat tgcccgcctg gagcagaacg ggagcccgct    420
aggaagagga aggcttggga gtacaggtgc aaaaatgcag ggagtgcctt taaaacactc    480
gggccatctg atgaaaacca accttaggaa aggaaccatg ctgccagttt tctgtgtggt    540
ggaacattat gaaaacgcca ttgaatatga ttg                                 573
```

```
<210> SEQ ID NO 6
<211> LENGTH: 21
<212> TYPE: DNA
<213> ORGANISM: Artificial Sequence
<220> FEATURE:
<223> OTHER INFORMATION: synthetic primer

<400> SEQUENCE: 6
gagacttcag gtcaggaaag c                                              21

<210> SEQ ID NO 7
<211> LENGTH: 21
<212> TYPE: DNA
<213> ORGANISM: Artificial Sequence
<220> FEATURE:
<223> OTHER INFORMATION: synthetic primer

<400> SEQUENCE: 7
ctgggctgtg aaattgatac c                                              21

<210> SEQ ID NO 8
<211> LENGTH: 19
<212> TYPE: DNA
<213> ORGANISM: Artificial Sequence
<220> FEATURE:
<223> OTHER INFORMATION: synthetic primer

<400> SEQUENCE: 8
ggagccgttc ttggtttca                                                 19

<210> SEQ ID NO 9
<211> LENGTH: 20
<212> TYPE: DNA
<213> ORGANISM: Artificial Sequence
<220> FEATURE:
<223> OTHER INFORMATION: synthetic primer

<400> SEQUENCE: 9
ttagacattt ctgaatgttc                                                20

<210> SEQ ID NO 10
<211> LENGTH: 21
<212> TYPE: DNA
<213> ORGANISM: Artificial Sequence
<220> FEATURE:
<223> OTHER INFORMATION: synthetic primer

<400> SEQUENCE: 10
gagacttcag gtcaggaaag c                                              21

<210> SEQ ID NO 11
<211> LENGTH: 21
<212> TYPE: DNA
<213> ORGANISM: Artificial Sequence
<220> FEATURE:
<223> OTHER INFORMATION: synthetic primer

<400> SEQUENCE: 11
ctgggctgtg aaattgatac c                                              21

<210> SEQ ID NO 12
<211> LENGTH: 20
<212> TYPE: DNA
<213> ORGANISM: Artificial Sequence
<220> FEATURE:
<223> OTHER INFORMATION: synthetic primer
```

```
<400> SEQUENCE: 12
gaagccgcac tttcttgaat                                          20

<210> SEQ ID NO 13
<211> LENGTH: 20
<212> TYPE: DNA
<213> ORGANISM: Artificial Sequence
<220> FEATURE:
<223> OTHER INFORMATION: synthetic primer

<400> SEQUENCE: 13
aatctccctc ctgcttccat                                          20

<210> SEQ ID NO 14
<211> LENGTH: 46
<212> TYPE: DNA
<213> ORGANISM: Artificial Sequence
<220> FEATURE:
<223> OTHER INFORMATION: synthetic shRNA

<400> SEQUENCE: 14
ggtggaagag taaactgttc ccgaaggaac agtttactct tccacc             46

<210> SEQ ID NO 15
<211> LENGTH: 21
<212> TYPE: DNA
<213> ORGANISM: Artificial Sequence
<220> FEATURE:
<223> OTHER INFORMATION: synthetic SAILOR exon 4 target sequence

<400> SEQUENCE: 15
ggtggaagag taaactgttc c                                        21
```

LONG NON-CODING RNA EXPRESSED IN AGGRESSIVE CANCER

CROSS-REFERENCES TO RELATED APPLICATIONS

This application is a continuation of PCT application PCT/US2015/031431, which claims priority benefit of U.S. Provisional Application No. 61/994,732, filed May 16, 2014 and U.S. Provisional Application No. 62/002,125, filed May 22, 2014. Each application is incorporated by reference for all purposes.

STATEMENT AS TO RIGHTS TO INVENTIONS MADE UNDER FEDERALLY SPONSORED RESEARCH AND DEVELOPMENT

This invention was made during work supported under Grant No. CA39681 awarded by the National Cancer Institute of the National Institutes of Health and under Contract No. DE-AC02-05CH11231 awarded by the U.S. Department of Energy. The government has certain rights in this invention.

REFERENCE TO SUBMISSION OF A SEQUENCE LISTING AS AN ASCII TEXT FILE

This application includes a Sequence Listing as a text file named 077429-1029648_SEQ_ST25.TXT" created on Nov. 16, 2016 and containing 119,057 bytes. The material contained in this text file is hereby incorporated by reference in its entirety for all purposes.

BACKGROUND OF THE INVENTION

For decades, only protein encoding RNAs were thought to be involved in mediating cell functions. However, researchers have recently discovered that RNAs that do not encode proteins, such as micro ribonucleic acids (microRNAs) and long noncoding RNAs (lncRNAs), are also involved in the regulation of cellular processes. It is particularly striking to note that, although approximately 70% of genomic DNA is transcribed, only ~1.2% of genomic transcripts have been found to encode proteins (Gutschner et al., *RNA Biol*, 9: 703-19, 2012).

To date, thousands of lncRNA have been discovered in cells, but the function of only a very small percentage (around 1%) of these lncRNAs has been characterized (Amaral et al., *Nucleic Acids Res*, 39:D146-51, 2011; Wilusz et al., *Genes Develop.* 23:1494-1504, 2009). Interestingly, of those lncRNA that have been studied, many have been shown to play important roles in the regulation of gene expression, and roles for lncRNA as mediators of oncogenic and tumour suppressive functions have been identified in pervasive cancer types, including breast and prostate cancers.

The mechanisms by which lncRNA are thought to modulate the expression of genes are multiple and diverse. One way in which nuclear-localized lncRNAs have been shown to act is in the control of gene expression. To do this, these lnRNAs guide epigenetic factors to gene regulatory sites in the genome. The lncRNA HOTAIR has been shown to work in cooperation with and recruit epigenetic factors to regulate programs of gene expression, and HOTAIR is involved processes that promote malignancy in cancers, including colorectal and breast cancers.

SATB1 (Dickinson et al., *Cell*, 70(4):631-45, 1992) is a nuclear protein that acts to regulate programs of gene expression through remodeling of the three-dimensional organization of the genome and epigenetic status of chromatin at a large number of target genomic loci. SATB1 is further described in U.S. Pat. No. 5,652,340 and antibodies made thereto are described in U.S. Pat. No. 5,869,621, which are hereby incorporated by reference.

SATB1 exhibits unique patterns of activity in the nuclei of aggressive breast cancer cells, and high levels of SATB1 expression directly correlate with a poor prognosis among breast cancer patients (Han et al., *Nature*, 452:187-193, 2008; Kohwi-Shigematsu et al., *Seminars in Cancer Biology*, 23:72-79, 2013; WO 2007/075206). In aggressive breast cancer cells, SATB1 reprograms the gene expression profile in order to promote cancer metastasis, and the knockdown of SATB1 expression in these cells blocks their tumorigenic and metastatic potential. Conversely, the ectopic expression of SATB1 in non-aggressive breast cancer cells increases their tumorigenic and metastatic potential. However, the mechanisms that operate in aggressive breast cancer to drive SATB1 expression or to guide SATB1 to its target gene loci are not yet known. Also, as a protein with other functions in multiple cell and tissue types, it is important to understand the mechanisms that are involved in directing the activities of SATB1 that increase the tumorigenic and, most importantly, the metastatic potential of breast cancers.

Cancers, including breast tumors, can be highly metastatic; when patients are diagnosed, there is often no way to tell if their tumor has the capacity to metastasize. This invention addresses the need to identify patients with potentially metastatic tumors vs. non-metastatic tumors.

BRIEF SUMMARY OF SOME EMBODIMENTS OF THE INVENTION

The present invention pertains to methods of screening for and determining the aggressiveness of cancer cells, e.g., breast cancer cells, based on the detection of a long noncoding RNA described herein, which is termed SAILOR. The invention further relates to methods and assay systems for rapid screening of therapeutics that target SAILOR; and use of SAILOR-targeted therapeutics for the treatment of breast cancer.

Thus, in some aspects, the invention is based on the discovery that a long intergenic noncoding (lncRNA; chr3: 18486850-18572715; Assembly hg19) is co-expressed with a SATB1 exon 1d variant from a common CpG island region specifically in human aggressive cancer cells, but not non-aggressive cancer cells. SATB1 has multiple splice variants that contain unique exon 1 sequences (a through d), but all encode the same SATB1 protein. The exon 1d variant, which is transcribed from the distal CpG island region, is specifically expressed in aggressive cancer cells. The lncRNA, which is referred to herein as SATB1 Adjacent intergenic lncRNA (SAILOR), is transcribed in the opposite direction from SATB1 from the same CpG island region in aggressive cancer cells. SAILOR is a nuclear lncRNA, strongly suggesting that it has a role in gene regulation. Reduction in SAILOR can reduce the growth rate of aggressive cells and SAILOR loss alters gene expression programs that typically promote tumor aggressiveness.

In some embodiments, the invention provides a method of determining the aggressiveness of a cancer, the method comprising: detecting the level of SAILOR transcripts in a sample from primary tumor tissue of a subject that has the cancer, and correlating the levels of expression with the aggressiveness of the cancer when a high level of expression is detected. The SAILOR transcript can have the sequence of SEQ ID NO:2 or 3; or the sequence of SEQ ID NO:4. In some embodiments, the detecting step comprises performing a quantitative PCR reaction or an in situ hybridization. In some embodiments, the method further comprises detecting the level of a SATB1 exon 1d transcript, e.g., SEQ ID NO:5, in the primary tumor sample. In some embodiments, detecting the level of the SATB1 exon 1d transcript comprises performing a quantitative PCR reaction or an in situ hybridization. In some embodiments, the cancer is breast cancer, pancreatic cancer, colon cancer, or prostate cancer.

In some embodiments, the invention provides a method of determining the aggressiveness of a cancer, the method comprising: detecting the level of SAILOR transcripts in an exosome sample a subject that has the cancer, and correlating the presence of the SAILOR transcript with the aggressiveness of the cancer. The SAILOR transcript can have the sequence of SEQ ID NO:2 or 3; or the sequence of SEQ ID NO:4. The method can further comprise detecting the presence of a SATB1 transcript in the exosome sample. In some embodiments, the cancer is breast cancer, pancreatic cancer, colon cancer, or prostate cancer. In some embodiments, the method further comprises recommending that the patient receive aggressive treatment for cancer.

In a further aspect, the invention provides a method of detecting the level of expression of SAILOR in a tissue sample, the method comprising contacting a nucleic acid obtained from the tissue sample with a probe that selectively hybridizes to SEQ ID NO:2 or SEQ ID NO:3; and detecting the amount of probe hybridized to the nucleic acid, thereby determining the level of expression. In some embodiments, the probe selectively hybridizes to SEQ ID NO:4.

In a further aspect, the invention provides an isolated nucleic comprising the sequence of SEQ ID NO:2, SEQ ID NO:3, or SEQ ID NO:4, or a fragment of SEQ ID NO:2, SEQ ID NO:3, or SEQ ID NO:4 that comprises at least 20, 25, 30, 35, 40, 45, 50, or 75 contiguous nucleotides of SEQ ID NO:2, SEQ ID NO:3, or SEQ ID NO:4, or a complement thereof. In some embodiments, the fragment comprises at least 100, 200, 300, 400, 500, 600, or 700 contiguous nucleotides of SEQ ID NO:2 or SEQ ID NO:3, or a complement thereof; or at least 100, 200, 300, 400, 500, 600, 700, 800, 900, 1000, 2000, 3000, or more contiguous nucleotides of SEQ ID NO:4, or the complement thereof. In some embodiments, the nucleic acid is attached to a fluorescent label.

The invention further provides a vector comprising a nucleic acid as set forth in the preceding paragraph.

In a further aspect, the invention provides a method of inhibiting proliferation of cancer cells, the method comprising contacting the cancer cells with an inhibitor of SAILOR that decreases the level of SAILOR. In some embodiments, the inhibitor is a nucleic acid inhibitor of SAILOR. In some embodiments, the cancer cells are breast cancer, pancreatic cancer, colon cancer, or prostate cancer cells.

Other objects, features, and advantages of the present invention will be apparent to one of skill in the art from the following detailed description and figures.

BRIEF DESCRIPTION OF THE DRAWINGS

FIG. 8, panels A and B, shows that cancer cells that attain resistance to drug treatments have an increased expression level of SATB1. (A) qRT-PCR analysis of MCF10A-1 cells treated individually with various drugs for 48 hrs that survived the treatment. (B) Vector control MCF10A-1 and SATB1-overexpressing MCF10A-1 cells were treated with a series of drug concentrations for 72 hrs and cell viability was assessed by MTT assay to determine LD50 of each drug.

DETAILED DESCRIPTION OF ASPECTS OF THE INVENTION

I. Introduction

Figure 1:
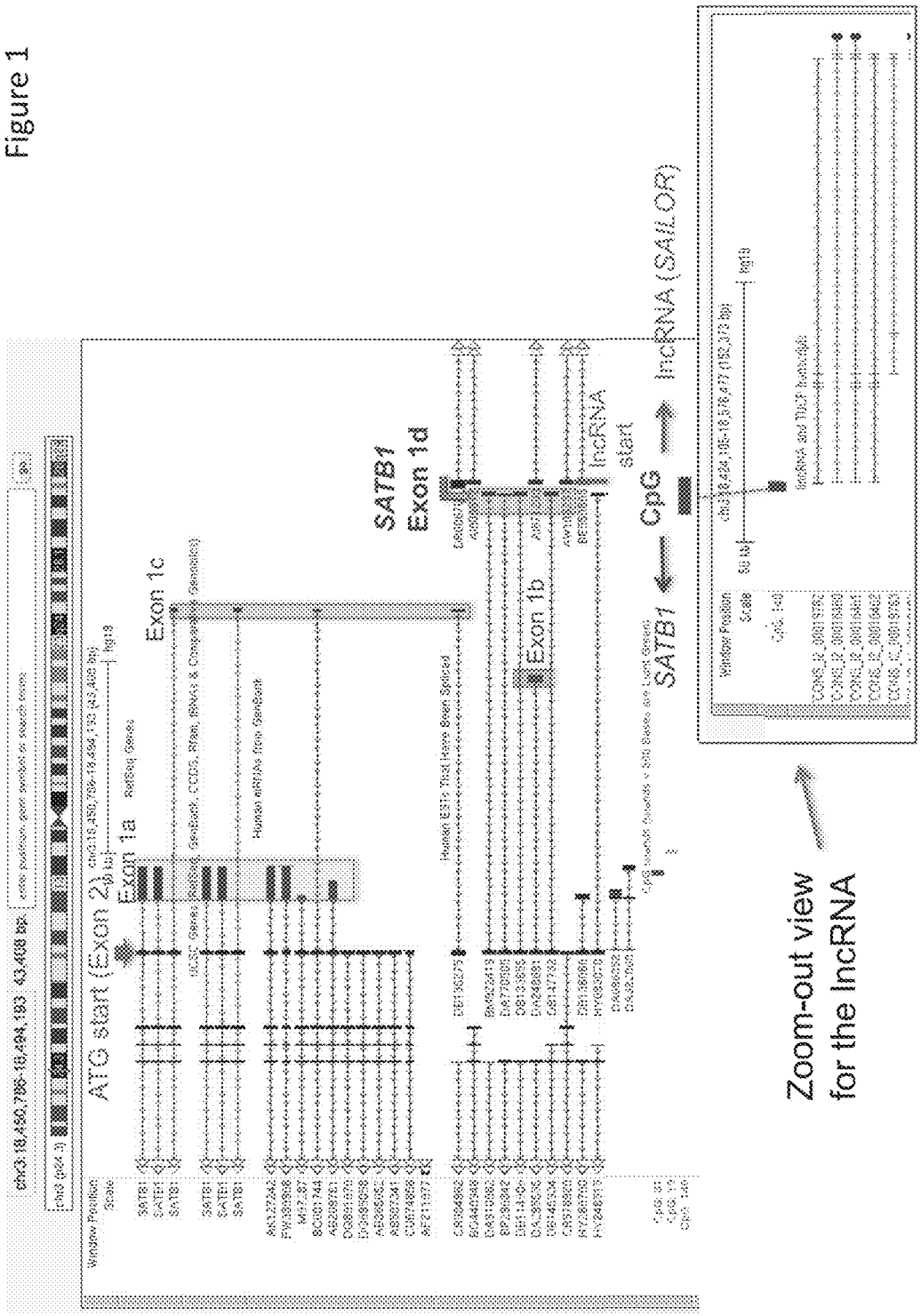
FIG. 1 is a map of the SATB1 gene locus, which is transcribed from multiple promoters to generate exon 1 variants (Exon 1a, 1b, 1c and 1d). SATB1 exon 1 is not translated and exon 2 has the ATG start site. Therefore, the SATB1 protein translated from each of these variants is identical. The far distal CpG island (>20 kb from exon 2) contains a promoter for SATB1 (exon 1d variant) and the nearby lncRNA. We refer to the lncRNA as SATB1 Adjacent Intergenic Long ncRNA, or SAILOR. The SAILOR gene spans 85.8 kb and encodes a 1.8 kb lncRNA (see zoom-out view). The distance between the transcriptional start sites of SATB1 exon 1d and SAILOR is 203 bp.

Described herein are methods for predicting the risk of disease recurrence, disease relapse, disease progression, and/or metastatic potential of a cancer in a subject. In one aspect, the invention thus provides methods of determining the expression level, such as the RNA expression level of SAILOR a tumor sample from a patient, and determining whether the subject has a likelihood of a poor prognosis based on the level of expression of SAILOR compared to a reference value of expression.

Evaluation of levels of SAILOR in tumor tissue will aid in selecting the treatment strategy for the patient. Importantly, an assay to detect SAILOR is easier to perform than the currently used immunohistochemical assays, which require analysis by trained pathologists. Furthermore, assays for coding mRNAs can be misleading because levels of mRNA do not always correlate with those of the proteins they encode. SAILOR therefore provides a superior marker for prognosis because it is the final, active product.

II. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "cancer" refers to any disease involving an abnormal growth of cells and includes all stages and all forms of the disease that affects any tissue, organ or cell in the body. The term includes all known cancers and neoplastic conditions, whether characterized as malignant, benign, soft tissue, or solid, and cancers of all stages and grades including pre- and post-metastic cancers. Examples of different types of cancer include, but are not limited to, breast cancer, lung cancer (e.g., non-small cell lung cancer); pancreatic cancer, digestive and gastrointestinal cancers such as colorectal cancer, gastrointestinal stromal tumors, gastrointestinal carcinoid tumors, colon cancer, rectal cancer, anal cancer, bile duct cancer, small intestine cancer, and stomach (gastric) cancer; esophageal cancer; gallbladder cancer; liver cancer; appendix cancer; ovarian cancer; renal cancer (e.g., renal cell carcinoma); cancer of the central nervous system; skin cancer; lymphomas; choriocarcinomas; head and neck cancers; osteogenic sarcomas; and blood cancers. As used herein, a "tumor" comprises one or more cancerous cells. The term "solid tumor" is used herein to refer to a mass of cancerous cells.

The terms "determining," "assessing," "assaying," "measuring" and "detecting" can be used interchangeably and refer to both quantitative and semi-quantitative determinations.

The term "amount" or "level" refers to the quantity of a polynucleotide of interest, e.g., in the present invention, typically a SAILOR RNA in a sample. Such quantity may be expressed in the absolute terms, i.e., the total quantity of the polynucleotide in the sample, or in the relative terms, i.e., the concentration of the polynucleotide in the sample.

The term "nucleic acid" or "polynucleotide" or "oligonucleotide" as used herein refers to a deoxyribonucleotide or ribonucleotide. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. The term encompasses nucleic acids containing known analogues of natural nucleotides which have similar or improved binding properties, for the purposes desired, as the reference nucleic acid. The term also includes nucleic acids which are metabolized in a manner similar to naturally occurring nucleotides or at rates that are improved for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) Toxicol. Appl. Pharmacol. 144:189-197. Other synthetic backbones encompassed by the term include methyl-phosphonate linkages or alternating methylphosphonate and phosphodiester linkages (Strauss-Soukup (1997) Biochemistry 36: 8692-8698), and benzylphosphonate linkages (Samstag (1996) Antisense Nucleic Acid Drug Dev 6: 153-156). The terms all encompass double- and single-stranded DNA, as well as double- and single-stranded RNA, microRNA, DNA:RNA hybrids, lncRNA, and hybrids between PNAs and DNA or RNA. As used herein, reference to a sequence by sequence identifier also explicitly encompasses reference to the complement of the sequence.

The term "hybridizing" refers to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences in a mixed population (e.g., a cell lysate or DNA preparation from a tissue biopsy). A "stringent hybridization" and "stringent hybridization wash conditions" in the context of nucleic acid hybridization (e.g., as in array, Southern or northern hybridizations) are sequence dependent, and are different under different environmental parameters. An extensive guide to the hybridization of nucleic acids is found in, e.g., Tijssen (1993) Laboratory Techniques in Biochemistry and Molecular Biology—Hybridization with Nucleic Acid Probes part I, Ch. 2, "Overview of principles of hybridization and the strategy of nucleic acid probe assays," Elsevier, N.Y. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook and Russell (2001) Molecular Cloning: A Laboratory Manual (3rd ed.) Vol. 1-3, Cold Spring Harbor Laboratory, Cold Spring Harbor Press, NY). An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4×SSC to 6×SSC at 40° C. for 15 minutes.

The term "complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Typically, the total number of mismatched nucleotides over a hybridizing region is not more than 3 nucleotides for sequences about 15 nucleotides in length. Conditions under which only exactly complementary nucleic acid strands will hybridize are referred to as "stringent" or "sequence-specific" hybridization conditions. Stable duplexes of substantially complementary nucleic acids can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs. For example, computer software for calculating duplex stability is commercially available from National Biosciences, Inc. (Plymouth, Minn.); e.g., OLIGO version 5, or from DNA Software (Ann Arbor, Mich.), e.g., Visual OMP 6. Stringent conditions are sequence-dependent and will be different in different circumstances. Generally, stringent conditions are selected to be about 5° C. lower to 5° C. higher than the thermal melting point (Tm) for the specific sequence at a defined ionic strength and pH. The Tm is the temperature (under defined ionic strength and pH) at which 50% of the duplex strands have dissociated. Relaxing the stringency of the hybridizing conditions will allow sequence mismatches to be tolerated; the degree of mismatch tolerated can be controlled by suitable adjustment of the hybridization conditions.

The term "probe" refers to an oligonucleotide that selectively hybridizes to a target nucleic acid under suitable conditions. A probe for detection of the biomarker sequences described herein can be any length, e.g., from 15-500 bp in length. Typically, in probe-based assays, hybridization probes that are less than 50 bp are preferred.

The term "target sequence" or "target region" refers to a region of a nucleic acid that is to be analyzed and comprises the sequence of interest.

The term "standard control" as used herein in the context of determining the level of a SAILOR polynucleotide, refers to an amount or concentration of a polynucleotide sequence that is present in an established tissue sample, e.g., a healthy, non-cancer tissue sample; or The standard control value is suitable for the use of a method of the present invention, to serve as a basis for comparing the amount of a specific mRNA or protein that is present in a test sample. An established sample serving as a standard control provides an average amount of a specific mRNA or protein that is typical in a normal tissue sample. A standard control value may vary depending on the nature of the sample as well as other factors such as the gender, age, ethnicity of the subjects based on whom such a control value is established.

The term "treatment," "treat," or "treating" refer to a method of reducing the effects of a disease or condition (e.g., cancer) or symptom of the disease or condition. Thus, in the disclosed method, treatment can refer to a 10%, 20%, 30%, 40%, 50%, 60%, 70%, 80%, 90%, or 100% reduction in the severity of an established disease or condition or symptom of the disease or condition. For example, a method of treating a disease is considered to be a treatment if there is a 10% reduction in one or more symptoms of the disease in a subject as compared to a control. Thus, the reduction can be a 10%, 20%, 30%, 40%, 50%, 60%, 70%, 80%, 90%, 100% or any percent reduction between 10 and 100% as compared to native or control levels. It is understood that treatment does not necessarily refer to a cure or complete ablation of the disease, condition, or symptoms of the disease or condition.

The term "sample" includes a biological sample or a sample from a biological source. Biological samples include samples from body fluids, e.g., blood, plasma, serum, or urine, or samples derived, e.g., by biopsy, from cells, tissues or organs, preferably tumor tissue suspected to include or essentially consist of cancer cells.

The term "recommending" or "suggesting," as used herein in the context of a treatment of cancer, refers to making a suggestion or a recommendation for therapeutic intervention (e.g., drug therapy, adjunctive therapy, etc.) and/or disease management which are specifically applicable to the patient.

The terms "responsive," "clinical response," "positive clinical response," and the like, as used in the context of a patient's response to an anticancer therapy, are used interchangeably and refer to a favorable patient response to a drug as opposed to unfavorable responses, i.e. adverse events. In a patient, beneficial response can be expressed in terms of a number of clinical parameters, including loss of detectable tumor (complete response, CR), decrease in tumor size and/or cancer cell number (partial response, PR), tumor growth arrest (stable disease, SD), enhancement of anti-tumor immune response, possibly resulting in regression or rejection of the tumor; relief, to some extent, of one or more symptoms associated with the tumor; increase in the length of survival following treatment; and/or decreased mortality at a given point of time following treatment. Continued increase in tumor size and/or cancer cell number and/or tumor metastasis is indicative of lack of beneficial response to treatment. In a population the clinical benefit of a drug, i.e., its efficacy can be evaluated on the basis of one or more endpoints. For example, analysis of overall response rate (ORR) classifies as responders those patients who experience CR or PR after treatment with drug. Analysis of disease control (DC) classifies as responders those patients who experience CR, PR or SD after treatment with drug.

A positive clinical response can be assessed using any endpoint indicating a benefit to the patient, including, without limitation, (1) inhibition, to some extent, of tumor growth, including slowing down and complete growth arrest; (2) reduction in the number of tumor cells; (3) reduction in tumor size; (4) inhibition (i.e., reduction, slowing down or complete stopping) of tumor cell infiltration into adjacent peripheral organs and/or tissues; (5) inhibition of metastasis; (6) enhancement of anti-tumor immune response, possibly resulting in regression or rejection of the tumor; (7) relief, to some extent, of one or more symptoms associated with the tumor; (8) increase in the length of survival following treatment; and/or (9) decreased mortality at a given point of time following treatment. Positive clinical response may also be expressed in terms of various measures of clinical outcome. Positive clinical outcome can also be considered in the context of an individual's outcome relative to an outcome of a population of patients having a comparable clinical diagnosis, and can be assessed using various endpoints such as an increase in the duration of recurrence-free interval (RFI), an increase in the time of survival as compared to overall survival (OS) in a population, an increase in the time of disease-free survival (DFS), an increase in the duration of distant recurrence-free interval (DRFI), and the like. Additional endpoints include a likelihood of any event (AE)-free survival, a likelihood of metastatic relapse (MR)-free survival (MRFS), a likelihood of disease-free survival (DFS), and a likelihood of distant metastatis-free survival (DMFS). An increase in the likelihood of positive clinical response corresponds to a decrease in the likelihood of cancer recurrence or relapse.

The term "good prognosis" refers to the prediction of the likelihood of disease-specific survival, overall survival or disease free survival, including partial remission, complete remission, and suppression of cancer cell proliferation and/or metastasis. A good prognosis for a patient with a solid tumor cancer includes a positive response rate in terms of disease remission or tumor shrinkage, or any other form of evaluating reduced tumor burden or growth. A good prognosis can be measured as the length (time) of survival.

The term "poor prognosis" refers to the prediction of the likelihood of cancer-attributable death or progression, including recurrence, relapse and/or metastatic spread.

The term "overall survival" refers to the time interval from either the time of diagnosis or the start of treatment that the patient is still alive.

The term "progression-free survival" refers to the time interval from treatment of the patient until the progression of cancer or death of the patient, whichever occurs first.

The term "responder" or "responsive" refers to a patient who has cancer, and who exhibits a beneficial clinical response following treatment with a cancer therapy.

The term "non-responder" or "non-responsive" refers to a patient who has a cancer, and who does not exhibit a beneficial clinical response following treatment with a cancer therapy.

The term "subject" as used herein is intended to cover an animal, preferably a mammal. Examples of subjects include humans, non-human primates, dogs, cows, horses, pigs, sheep, goats, cats, mice, rabbits, rats, and transgenic non-human animals. In some embodiments, the subject is a human, e.g., a human suffering from, at risk of suffering from, or potentially capable of suffering from cancers.

The term "score" refers to a statistically derived value that can provide physicians and caregivers valuable diagnostic and prognostic insight. In some instances, the score provides a projected risk of disease recurrence/relapse or disease progression, a projected rate of disease progression, and/or a projected response to a particular therapy. An individual's score can be compared to a reference score or a reference score scale to determine risk of disease recurrence/relapse or to assist in the selection of therapeutic intervention or disease management approaches.

The term "SAILOR score" or "SAILOR value" refers to an expression score, i.e., based on the level of SAILOR RNA.

III. Detailed Descriptions of Embodiments

The methods described herein are based, in part, on the discovery that SAILOR is expressed at high levels in aggressive cancer cells. The methods described herein can be used to evaluate a primary tumor to determine the likelihood of tumor progression. Non-limiting examples of cancer include breast cancer, pancreatic cancer, lung cancer, colorectal cancer, digestive and gastrointestinal cancers such as colorectal cancer, gastrointestinal stromal tumors, gastrointestinal carcinoid tumors, colon cancer, rectal cancer, anal cancer, bile duct cancer, small intestine cancer, and stomach (gastric) cancer; esophageal cancer; gallbladder cancer; liver cancer; pancreatic cancer; appendix cancer; bladder cancer; prostate cancer; cervical cancer; uterine cancer; ovarian cancer; renal cancer (e.g., renal cell carcinoma); cancer of the central nervous system, e.g., lower grade brain cancer; skin cancer; lymphomas; head and neck cancers; adrenocortical cancer; and thyroid cancer. In some embodiments, primary breast cancer tissue is evaluated for SAILOR transcript levels. In some embodiments, primary pancreatic cancer tissue is evaluated for SAILOR transcript levels.

In some embodiments, a subject may have an early stage cancer, e.g., Stage I or Stage 2 cancer, such as an early stage breast cancer, pancreatic cancer, lung cancer, gastric cancer, or ovarian cancer.

The tumor sample can be any biological sample comprising cancer cells. In some embodiments, the tumor sample is a fresh or archived sample obtained from a primary tumor, e.g., by a tumor biopsy or fine needle aspirate. The sample also can be any biological fluid containing cancer cells. The tumor sample can be isolated or obtained from any number of primary tumors, including, but not limited to, tumors of the breast, pancreas, lung, prostate, brain, liver, kidney, intestines, colon, spleen, thymus, testis, ovary, uterus, and the like. In some embodiments, the tumor sample is from a tumor cell line. The collection of a tumor sample from a subject is performed in accordance with the standard protocol generally followed by hospital or clinics, such as during a biopsy.

In some embodiments SAILOR transcripts are detected in exosomes. Detection of SAILOR in exosome is indicative of cancer this is progressing. Exosomes (reported diameter of between 30 and 100 nm) are vesicles released by all cells and are present in my biological fluids, including blood, urine, cerebrospinal fluid and saliva. Exosomes contain RNA, including mRNA, microRNA, lncRNA and other RNA species, as well as DNA and proteins, from their cell of origin (see, e.g., Raposo & Stoorvogel, J. Cell. Biol 200:373-383, 2013). In some embodiments, SAILOR or SATB1 transcripts are identified in exosomes present in plasma or serum samples from a patient. In some embodiments, exosomes for evaluation are at least partially purified.

The transcript level of SAILOR in a sample can be determined by any suitable method known in the art. Measurement of the level can be direct or indirect. For example, the abundance levels of SAILOR can be directly quantitated. Alternatively, the amount of SAILOR can be determined indirectly by measuring abundance levels of cDNAs, amplified RNAs or DNAs, or by measuring quantities or activities of RNAs, or other molecules that are indicative of the expression level of SAILOR. Although the following section describes detection of SAILOR lncRNA, one of skill understands that similar methodology can be employed to detect other transcripts, such as SATB1 exon 1d transcripts.

The invention employs routine techniques in the field of recombinant genetics. Basic texts disclosing the general methods of use in this invention include Green and Sambrook (2012) Molecular Cloning: A laboratory manual 4th ed. Cold Spring Harbor Laboratory Press; and Current Protocols in Molecular Biology and supplements through supplement 110, 2015) John Wiley and Sons.

The level of SAILOR expression can be detected or measured by a variety of methods including, an amplification assay, a hybridization assay, a sequencing assay, or an array. Non-limiting examples of such methods include reverse-transcription polymerase chain reaction (RT-PCR); quantitative real-time PCR (qRT-PCR); quantitative PCR, such as TagMan®; Northern blotting; in situ hybridization assays; microarray analysis, e.g., microarrays from NanoString Technologies; multiplexed hybridization-based assays, e.g., QuantiGene 2.0 Multiplex Assay from Panomics; serial analysis of gene expression (SAGE); cDNA-mediated annealing, selection, extension, and ligation; nucleic acid immunoassay, direct sequencing or pyrosequencing; massively parallel sequencing; next generation sequencing; high performance liquid chromatography (HPLC) fragment analysis; capillarity electrophoresis; mass spectrometry, including SELDI, MALDI; and other known methods.

Various methods involving amplification reactions and/or reactions in which probes are linked to a solid support and used to quantify RNA may be used. Alternatively, the RNA, or DNA copy of the RNA, may be linked to a solid support and quantified using a probe to the sequence of interest.

In some embodiments, the target RNA is first reverse transcribed and the resulting cDNA is quantified. In some embodiments, RT-PCR or other quantitative amplification techniques are used to quantify the target RNA. Amplification of cDNA using PCR is well known (see U.S. Pat. Nos. 4,683,195 and 4,683,202; PCR PROTOCOLS: A GUIDE TO METHODS AND APPLICATIONS (Innis et al., eds. 1990)). Methods of quantitative amplification are disclosed in, e.g., U.S. Pat. Nos. 6,180,349; 6,033,854; and 5,972,602, as well as in, e.g., Gibson et al., Genome Research 6:995-1001 (1996); DeGraves, et al., Biotechniques 34(1):106-10, 112-5 (2003); Deiman B, et al., Mol Biotechnol. 20(2):163-79 (2002). Alternative methods for determining the level of SAILOR in a sample may involve other nucleic acid amplification methods such as ligase chain reaction (Barany (1991) Proc. Natl. Acad. Sci. USA 88:189-193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (U.S. Pat. No. 5,854,033) or any other nucleic acid amplification method, followed by the detection of the amplified molecules using techniques well known to those of skill in the art.

In some embodiments, RNA (or a copy) is immobilized on a solid surface and contacted with a probe, e.g., in a microarry, dot blot or Northern format. A skilled artisan can readily adapt known RNA detection methods for use in detecting the level SAILOR.

In some embodiments, microarrays are employed. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, U.S. Pat. Nos. 6,040,138, 5,800,992 and 6,020,135, 6,033,860, and 6,344,316. High-density oligonucleotide arrays are particularly useful for determining the gene expression profile for a large number of RNA's in a sample.

Techniques for the synthesis of these arrays using mechanical synthesis methods are described in, e.g., U.S. Pat. No. 5,384,261. Although a planar array surface is often employed the array may be fabricated on a surface of virtually any shape or even a multiplicity of surfaces. Arrays may be peptides or nucleic acids on beads, gels, polymeric surfaces, fibers such as fiber optics, glass or any other appropriate substrate, see U.S. Pat. Nos. 5,770,358, 5,789, 162, 5,708,153, 6,040,193 and 5,800,992. Arrays may be packaged in such a manner as to allow for diagnostics or other manipulation of an all-inclusive device.

In some embodiments, gene-specific probes and/or primers are used in hybridization assays to detect RNA expression. The probes and/or primers may be labeled with any detectable moiety or compound, such as a radioisotope, fluorophore, chemiluminescent agent, and enzyme.

Probes and primers can be selected using know algorithms that takes into account binding energies, base composition, sequence complexity, cross-hybridization binding energies, and secondary structure. See, e.g., PCT Patent Publication WO 01/05935, published Jan. 25, 2001; Hughes et al., Nat. Biotech. 19:342-7 (2001).

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-Van Devanter et al., *Nucleic Acids Res.* 12:6159-6168, 1984.

In some embodiments, probes can be obtained, e.g., by polymerase chain reaction (PCR) amplification of genomic DNA or RNA or cloned sequences. PCR primers are selected based on a known sequence of the genome that will result in amplification of specific fragments of genomic DNA. Computer programs that are well known in the art are useful in the design of primers with the required specificity and optimal amplification properties, such as Oligo version 5.0 (National Biosciences). Typically each probe is between 10 bases and 50,000 bases, usually between 300 bases and 1,000 bases in length. It will be apparent to one skilled in the art that controlled robotic systems are useful for isolating and amplifying nucleic acids.

In some embodiments, in situ hybridization is employed to assess SAILOR transcript levels.

The probe for measuring SAILOR transcript level may be employed that hybridizes anywhere within SAILOR (SEQ ID NO:2, SEQ ID NO:3, or SEQ ID NO:4) that provides for selective measure of SAILOR.

The level of SAILOR can be normalized to a reference level for a control gene. The control value can be predetermined, determined concurrently, or determined after a sample is obtained from the subject. The standard can be run in the same assay or can be a known standard from a previous assay. In some embodiments, a normalized level of SAILOR can be transformed into a score for likelihood of progression.

Determining the Likelihood of Progression

After determining the level of SAILOR transcript one of skill can correlate the level with risk of having an aggressive cancer, where a high level of expression indicates an aggressive cancer. For example, in some embodiments, a high level of expression is determined relative to a reference scale, e.g., SAILOR expression levels obtained from corresponding tissue from a population of normal reference subjects that that do not have cancer or that have a non-aggressive from of the same cancer as the patient. The subjects in the reference population can be within the appropriate parameters, if applicable, for the purpose of screening for and/or monitoring cancer using the methods provided herein. Optionally, the reference subjects are of same gender, similar age, or similar ethnic background. The reference subject may be of the same gender, similar age, or similar ethnic background as the test subject. In some embodiments, the reference subjects may have a benign or non-malignant from of the cancer of interest. Thus, in some embodiments, determination of "high" level of expression is relative to levels in benign tumors that do not progress. In some embodiments, a "high" level of expression is at least 10-fold, at least 20-fold, 25-fold, 30-fold, or 50-fold greater, when normalized, than that observed in the corresponding normal tissue. In some embodiments, "high" expression is at least 40 or 50-fold greater than in normal tissue.

The status of the reference subjects can be confirmed by well established, routinely employed methods including but not limited to general physical examination of the individuals and general review of their medical history. As understood by one of skill in the art, a reference population is of a size sufficient to establish that the samples obtained from the group can be reasonably regarded as representative of the normal or average level among this population of subjects.

In some embodiments, a patient is consider to have a tumor with a high risk of progression when the level of SAILOR exceeds a threshold level. To establish a threshold value, an average value is determined based on the individual values found in each subject of the selected reference group. For example, a risk score over the threshold value can indicate a more than average likelihood of cancer progression whereas a risk score below the threshold value can indicate an average or below-average likelihood of cancer progression. In some embodiments, a standard deviation is also determined during the same process. In some cases, separate threshold values may be established for separately defined groups having distinct characteristics such as age, gender, or ethnic background. The patient's risk score is compared to one or more threshold values. In some embodiments, the risk score is deemed "high" if it is at least 2, 3, 4, 5, 10, 15, 20 or more standard deviations greater than the threshold value. In other embodiments, the risk score is "low" or below the threshold if it is at least 2, 3, 4, 5, 10, 15, 20 or more standard deviations lower than the threshold value.

In some embodiments, e.g., where SAILOR levels are evaluated using quantitative PCR, the test level and the control level may be expressed as a mean comparative quantification (Cq) test value and a mean comparative quantification (Cq) control value (delta Cq method). In such a case, the mean Cq test value and a mean Cq control value are normalized by an internal control. For example, in tumor tissue samples, the difference of threshold cycle (Cq) values obtained for SAILOR and internal control in a cancer specimen is compared to the difference of the Cq values obtained in adjacent normal tissue. The delta-delta Cq method may then be used to calculate the relative expression values between tissue samples.

The level of expression of SAILOR can be evaluated alone or in combination with other markers, such as the level of SATB1 exon 1d or other clinical parameters.

In some embodiments, a computer-based analysis program is used to translate the raw data generated by the detection methods described herein (e.g., the presence, absence, or amount of a given marker or markers) into a risk score of predictive value to a clinician.

High level of expression of SAILOR is indicative of an aggressive cancer. Aggressive cancer can often be associated with a poor prognosis, e.g., cancer relapse, cancer recurrence, cancer progression, and/or local or distant metastasis. In some cases, high levels of SAILOR can predicts that the subject will have poor metastatic relapse-free survival (MRFS), such as a short term MRFS, no MRFS, or a below-average probability of MRFS. In other cases, high levels of SAILOR is indicative that the subject will have poor any event (AE)-free survival, e.g., a short term AE-free survival, no AE-free survival, or a below-average probability of AE-free As explained above, SAILOR transcript level is often used in conjunction with other diagnostic criteria, including both clinical and pathology evaluations. For example, in breast cancer, the estrogen receptor status is also typically determined.

In some embodiments, the presence of an aggressive cancer can be detected by detecting the presence of SAILOR and/or SATB1 transcripts in exosomes from a patient. In this context, detecting the "presence" of the transcripts in exosomes means that the level is at a statistically significant higher level, e.g., 1.5-fold, 1.6-, 1.7, 1.8, 1.9, or preferably 2.0-fold, or greater than that of a control value. The control value may represent the copy number or concentration of the transcript from a corresponding exosome sample from a normal patient, or a patient that has a non-aggressive from of the cancer.

Any of the methods described herein for determining risk of having an aggressive cancer may be totally or partially performed with a computer system including one or more processors, which can be configured to perform the steps.

Thus, embodiments are directed to computer systems configured to perform the steps of any of the methods described herein, potentially with different components performing a respective step or a respective group of steps.

It should be understood that any of the embodiments of the present disclosure can be implemented in the form of control logic using hardware (e.g., an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Selecting Cancer Therapies some embodiments, the methods of the present disclosure also include selecting a therapeutic intervention for a subject with cancer having a high SAILOR transcript level score. For example, a more aggressive therapy may be selected for patients exhibited high levels of SAILOR. For example, multiple therapies, including chemotherapy, may be employed. Various therapies include radiation therapy, chemotherapy, drug therapy, e.g., hormone therapy, immunotherapy, surgery, or any combination thereof can be selected. In some instances, surgery and an adjuvant therapy, such as chemotherapy, drug therapy, e.g., hormone therapy, immunotherapy, or any combination thereof are suggested to the subject.

Non-limiting examples of useful chemotherapy agents include alkylating agents, e.g., cyclophosphamide, mechlorethamine, chlorambucil, ifosfamid, melphalan, streptozocin, carmustine, lomustine, busulfan, dacarbazine, temozolomide, thiotepa, and altretamine, antimetabolites, e.g., 5-fluorouracil (5-FU), 6-mercaptopurine (6-MP), capecitabine, cytarabine, floxuridine, gemcitabine, hydroxyurea, methotrexate, and pemetrexed, anthracyclines, e.g., daunorubicin, doxorubicin, epirubicin, and idarubicin, other antitumor antibiotics, e.g., actinomycin-D, bleomycin, mitomycin-c and mitoxantrone, topoisomerase inhibitors, e.g., topotecan, irinotecan, etoposide, teniposide, and metoxantrone, mitotic inhibitors, e.g., paclitaxel, docetaxel, ixabepilone, vinblastine, vincristine, vinrelbine, and estramustine, corticosteroids, e.g., prednisone, methylprednisone, and dexamethasone, L-aspraginase, and the proteasome inhibitor bortezomib. Without limitations, examples of radiation therapy include external beam radiation therapy, internal radiation therapy, or systemic radiation therapy.

The therapeutic intervention can include one or more DNA damaging compounds or agents, such as cisplatin, carboplatin, oxaliplatin, picoplatin, other platinum-based compounds, doxorubicin, daunorubicin, other anthracyclines, variants thereof and derivatives thereof.

In some instances, administration of one or more anthracyclines; cyclophosphamide; one or more taxanes; methotrexate; 5-fluorouracil; one or more anthracyclines and cyclophosphamide; one or more anthracyclines, cyclophosphamide, and one or more taxanes; cyclophosphamide, methotrexate and 5-fluorouracil, or any combination thereof is recommended.

SAILOR Inhibitors

In a further aspect, the invention provides SAILOR inhibitors to decrease SAILOR LEVELS. Such inhibitors can be used, e.g., therapeutically. SAILOR inhibitors include, but are not limited to, antisense oligonucleotides, inhibitory RNA molecules, such as miRNAs, siRNAs, piRNAs, and snRNAs, ribozymes, and small molecule inhibitors. Various types of inhibitors for inhibiting nucleic acid function are well known in the art.

The terms "microRNA," "miRNA," and MiR" are interchangeable and refer to endogenous or artificial non-coding RNAs that are capable of regulating gene expression. It is believed that miRNAs function via RNA interference.

in the context of this invention, the terms "siRNA" and "short interfering RNA" are interchangeable and refer to single-stranded or double-stranded RNA molecules that are capable of inducing RNA interference. SiRNA molecules typically have a duplex region that is between 18 and 30 base pairs in length.

The terms "snRNA" and "small nuclear RNA" are interchangeable and refer to a class of small RNAs involved in a variety of processes including RNA splicing and regulation of transcription factors. The subclass of small nucleolar RNAs (snoRNAs) is also included. The term is also intended to include artificial snRNAs, such as antisense derivatives of snRNAs comprising antisense sequences directed against SAILOR.

The term "hairpin" and "stem-loop" can be used interchangeably and refer to stem-loop structures. The stem results from two sequences of nucleic acid or modified nucleic acid annealing together to generate a duplex. The loop lies between the two strands comprising the stem.

Inhibitors can be single stranded or double stranded polynucleotides and may contain one or more chemical modifications, such as, but not limited to, locked nucleic acids, peptide nucleic acids, sugar modifications, such as 2'-O-alkyl (e.g., 2'-O-methyl, 2'-O-methoxyethyl), 2'-fluoro, and 4'-thio modifications, and backbone modifications, such as one or more phosphorothioate, morpholino, or phosphonocarboxylate linkages. In addition, inhibitory RNA molecules may have a "tail" covalently attached to their 3'- and/or 5'-end, which may be used to stabilize the RNA inhibitory molecule or enhance cellular uptake. Such tails include, but are not limited to, intercalating groups, various kinds of reporter groups, and lipophilic groups attached to the 3' or 5' ends of the RNA molecules. In certain embodiments, the RNA inhibitory molecule is conjugated to cholesterol or acridine. See, for example, the following for descriptions of syntheses of 3'-cholesterol or 3'-acridine modified oligonucleotides: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993); herein incorporated by reference in their entireties. Additional lipophilic moieties that can be used, include, but are not limited to, oleyl, retinyl, and cholesteryl residues, cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O.sub.3-(oleoyl)lithocholic acid, O.sub.3-(oleoyl)cholenic acid, dimethoxytrityl, or phenoxazine. Additional compounds, and methods of use, are set out in US Patent Publication Nos. 2010/0076056, 2009/0247608 and 2009/0131360; herein incorporated by reference in their entireties.

In one embodiment, a SAILOR inhibitor for use in this invention is an antisense oligonucleotide. An antisense oligonucletoide may comprise ribonucleotides or deoxyribonucleotides. Typically antisense oligonucleotides have at least one chemical modification, e.g., as described in the preceding paragraph. In some embodiments, suitable antisense oligonucleotides are 2'-O-methoxyethyl "gapmers" containing 2'-O-methoxyethyl-modified ribonucleotides on both 5' and 3' ends with at least ten deoxyribonucleotides in the center. Such "gapmers" trigger RNase H-dependent degradation mechanisms of RNA targets.

Other modifications of antisense oligonucleotides to enhance stability and improve efficacy, such as those described in U.S. Pat. No. 6,838,283, are known in the art and are suitable for use in the methods of the invention. Antisense oligonucleotides comprise a sequence that is at least partially complementary to a SAILOR target sequence, e.g., at least about 75%, 80%, 85%, 90%, 91%, 92%, 93%, 94%, 95%, 96%, 97%, 98%, or 99% complementary to the SAILOR target sequence. In some embodiments, an antisense oligonucleotide at least about 90%, 91%, 92%, 93%, 94%, 95%, 96%, 97%, 98%, 99%, or 100% complementary to a target SAILOR polynucleotide sequence present in SEQ ID NO:2 or SEQ ID NO:3 that is selective for SAILOR. In some embodiments, an antisense oligonucleotide at least about 90%, 91%, 92%, 93%, 94%, 95%, 96%, 97%, 98%, 99%, or 100% complementary to a target SAILOR polynucleotide sequence present in SEQ ID NO:4 that is selective for SAILOR.

In some embodiments, a SAILOR inhibitor is an inhibitory RNA molecule such as a miRNA, a siRNA, a piRNA, or a snRNA that has a single-stranded or double-stranded region that is at least partially complementary to the SAILOR target sequence, e.g., about 75%, 80%, 85%, 90%, 91%, 92%, 93%, 94%, 95%, 96%, 97%, 98%, or 99% complementary to the SAILOR target sequence. In some embodiments, the inhibitory RNA comprises a sequence that is at least about 90%, 91%, 92%, 93%, 94%, 95%, 96%, 97%, 98%, 99%, or 100% complementary to a SAILOR target sequence, e.g., any sequence present in SEQ ID NO:2 that is selective for SAILOR. In certain embodiments, the inhibitory RNA molecule may be a double-stranded, small interfering RNA or a short hairpin RNA molecule (shRNA) comprising a stem-loop structure.

In some embodiments, an shRNA or other inhibitory RNA targets the mature SAILOR transcript, e.g., SEQ ID NO:2 or SEQ ID NO:3.

A SAILOR inhibitor that decreases SAILOR transcript levels (e.g., microRNA, siRNA, piRNA, snRNA, antisense oligonucleotide, ribozyme, or small molecule inhibitor) often reduces the amount and/or activity of SAILOR by at least about 10% to about 100%, 20% to about 100%, 30% to about 100%, 40% to about 100%, 50% to about 100%, 60% to about 100%, 70% to about 100%, 10% to about 90%, 20% to about 85%, 40% to about 84%, 60% to about 90%, including any percent within these ranges, such as but not limited to 15%, 20%, 25%, 30%, 35%, 40%, 45%, 50%, 55%, 60%, 65%, 70%, 75%, 80%, 85%, 90%, 95%, 96%, 97%, 98%, and 99%.

In some embodiments, a SAILOR inhibitor is administered to a subject as a nucleic acid construct, for example using a plasmid-based delivery system or a viral delivery system. Numerous vectors are known in the art including, but not limited to linear polynucleotides, polynucleotides associated with ionic or amphiphilic compounds, plasmids, and viruses. Viral delivery systems include adenovirus vectors, adeno-associated viral vectors, herpes simplex viral vectors, retroviral vectors, pox viral vectors, lentiviral vectors, alphavirus vectors, poliovirus vectors, and other positive and negative stranded RNA viruses, viroids, and virusoids, or portions thereof. Methods of constructing and using such vectors are well known in the art.

Any of the conventional vectors used for expression in eukaryotic cells may be used for directly introducing nucleic acids into tissue. Expression vectors containing regulatory elements from eukaryotic viruses are often used in eukaryotic expression vectors. Such regulatory elements include, e.g., human CMV, simian CMV, viral LTRs, and the like. Typical vectors may comprise, e.g., termination sequences and other sequences for providing the desired expression activity of the vector. and other elements and an antibiotic resistance gene for selective growth in bacteria.

In certain embodiments, gene transfer may be performed under ex vivo conditions. Ex vivo gene therapy refers to the isolation of cells from an animal, the delivery of a nucleic acid into the cells in vitro, and then the return of the modified cells back into the subject.

Administering a nucleic acid, such as a microRNA, siRNA, piRNA, snRNA, or antisense nucleic acid inhibitor of SAILOR to cells can be performed using any known technique. For example, in some embodiments, a composition comprising one or more nucleic acid molecules (within or without vectors) can comprise a delivery vehicle, including liposomes, for administration to a subject, carriers and diluents and their salts, and/or can be present in pharmaceutically acceptable formulations. Methods for the delivery of nucleic acid molecules are described, for example, in Gilmore, et al., Curr Drug Delivery (2006) 3:147-5 and Patil, et al., AAPS Journal (2005) 7:E61-E77. Delivery of siRNA molecules is also described in several U.S. Patent Publications, including for example, 2006/0019912; 2006/0014289; 2005/0239687; 2005/0222064; and 2004/0204377, the disclosures of each of which are hereby incorporated herein by reference. Nucleic acid molecules can be administered to cells by a variety of methods known to those of skill in the art, including, but not restricted to, encapsulation in liposomes, by iontophoresis, by electroporation, or by incorporation into other vehicles, including biodegradable polymers, hydrogels, cyclodextrins (see, for example Gonzalez et al., 1999, Bioconjugate Chem., 10, 1068-1074; Wang et al., International PCT publication Nos. WO 03/47518 and WO 03/46185), poly(lactic-co-glycolic) acid (PLGA) and PLCA microspheres (see for example U.S. Pat. No. 6,447,796 and US Patent Application Publication No. 2002/130430), biodegradable nanocapsules, and bioadhesive microspheres, or by proteinaceous vectors (O'Hare and Normand, International PCT Publication No. WO 00/53722). In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

In some embodiments, a SAILOR inhibitor is targeted to cancer cells. Suitable cancer cell-specific targeting approaches include a lentivirus-mediated Tet-On inducible system under the control of the matrix metalloproteinase-2 promoter; a dual promoter system that combines the human telomerase reverse transcriptase promoter (hTERT) and a tissue specific promoter to target expression to cancer cells. Other cancer cell-specific targeting approaches utilizing the hTERT tumor-specific promoter are also suitable for use in the present invention.

Administration may be systemic or via direct or local administration to a tumor site. By way of example, suitable modes of systemic administration include, without limitation orally, topically, transdermally, parenterally, intradermally, intramuscularly, intraperitoneally, intravenously, subcutaneously, or by intranasal instillation, by intracavitary or intravesical instillation, intraocularly, intraarterialy, intralesionally, or by application to mucous membranes. Suitable modes of local administration include, without limitation, catheterization, implantation, direct injection, dermal/transdermal application, or portal vein administration to relevant tissues, or by any other local administration technique, method or procedure generally known in the art.

Screening for SAILOR Inhibitors

In a further aspect, the invention provides method of screening for SAILOR inhibitors. Use of a regulatory element either individually for SATB1 or SAILOR expression, or simultaneously for expression of both genes within the CpG island region (see, SEQ ID NO:1) can be used in a small chemical inhibitor-screening assay to identify compounds that abrogate expression of both molecules.

In one embodiment, an illustrative screening is as follows. the entire SATB1 coding region is replaced with a reporter Green Fluorescent Protein (GFP) gene fused with the human SATB1 nuclear localization signal (NLS, amino acids 20-40) (Nakayama et al, *Cell cycle* 4:109901106, 2005) or any other established NLS, and also replace the entire target SAILOR lncRNA with a red fluorescent protein reporter fused with the coding sequence for a NLS. Based on this design, these gene features are cloned into an expression cassette: the two genes will be transcribed from the promoters of the CpG island in opposite directions. This expression cassette is transduced into a human aggressive breast cancer cell line for which we know the expression level of SATB1 and SAILOR lncRNA; both will be high. Dual expression in nuclei of both fluorescent-labeled reporter genes coming from the expression cassette will make it possible to directly visualize and compare the expression levels of each different transcript under various experimental conditions. For example, one assay that could be done will screen anti-cancer compounds to determine to what extent a small chemical can ablate or vastly diminish one or both colors in transduced cells.

In another embodiment, an expression construct contains the regulatory elements (i.e. promoters) within the CpG island that directs both the transcription of SATB1 and adjacent lncRNA. In some embodiments, the expression construct comprises a vector, reporter gene, and a gene, cDNA or nucleotide sequences that expresses SATB1.

The expression vector usable for screening includes pUC vectors (for example pUC118, pUC119), pBR vectors (for example pBR322), pBI vectors (for example pBI112, pBI221), pGA vectors (pGA492, pGAH), pNC (manufactured by Nissan Chemical Industries, Ltd.). In addition, virus vectors including but not limited to lentiviral, adenoviral, retroviral or sendai viral vectors can also be used.

The expression system usable in the screening methods described herein includes any system utilizing RNA or DNA sequences. It can be used to transform transiently or stably in the selected host. It includes any plasmid vectors, such as pUC, pBR, pBI, pGA, pNC derived vectors (for example pUC118, pBR322, pBI221 and pGAH). It also includes any viral DNA or RNA fragments derived from virus such as phage and retro-virus derived (TRBO, pEYK, LSNLsrc). Genes or nucleic acid sequences presented in the invention can be expressed by direct translation in case of RNA viral expression system, transcribed after in vivo recombination, downstream of promoter recognized by the host expression system (such as pLac, pVGB, pBAD, pPMA1, pGa14, pHXT7, pMet26, pCaMV-35S, pCMV, pSV40, pEM-7, pNos, pUBQ10, pDET3, or pRBCS.) or downstream of a promoter present in the expression system (vector or linear DNA). Promoters can be from synthetic, viral, prokaryote and eukaryote origin.

The expression cassette may include 5' and 3' regulatory sequences operably linked, for examples, to the reporter gene, the lncRNA or SATB1 gene. "Operably linked" is intended to mean a functional linkage between two or more elements. For example, an operable linkage between a gene and a regulatory sequence (i.e. a promoter) is functionally linked that allows for expression of the gene. Operably linked elements may be contiguous or non-contiguous. When used to refer to the joining of two protein coding regions, by operably linked is intended that the coding regions are in the same reading frame. The cassette may additionally contain at least one additional gene to be co-transfected into the organism. Alternatively, the additional gene(s) can be provided on multiple expression cassettes. Such an expression cassette is provided with a plurality of restriction sites and/or recombination sites for insertion of the gene sequence. The expression cassette may additionally contain selectable marker genes or a reporter gene to be under the transcriptional regulation of the regulatory regions.

The expression cassette may include in either the direction of transcription, a transcriptional initiation region (i.e. a promoter), translational initiation region, a polynucleotide of the invention, a translational termination region, and optionally, a transcriptional termination region functional in the host organism. The regulatory regions (e.g. promoters, transcriptional regulatory regions, and translational termination regions) and/or the polynucleotide of the invention may be native/analogous to the host cell or to each other. Alternatively, the regulatory regions and/or the gene may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or if from the same/analogous species, one or both are substantially modified from their original form and/or genomic locus, or the promoter is not the native promoter for the operably linked polynucleotide.

Where appropriate, polynucleotides may be optimized for increased expression in the transformed organism. For example, polynucleotides can be synthesized using preferred codons for improved expression.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassette can also comprise a selectable marker gene for the selection of transformed or modulated cells. Selectable marker genes are utilized for the selection of transformed or differentiated cells or tissues. Marker genes include genes encoding antibiotic resistance, such as those encoding neomycin phosphotransferase II (NEO) and hygromycin phosphotransferase (HPT). Additional selectable markers include phenotypic markers such as ?-galactosidase and fluorescent proteins such as green fluorescent protein (GFP) (Su et al. (2004) Biotechnol Bioeng 85:610-9 and Fetter et al. (2004) Plant Cell 16:215-28), cyan florescent protein (CYP) (Bolte et al. (2004) J. Cell Science 117:943-54 and Kato et al. (2002) Plant Physiol 129:913-42), and yellow florescent protein (PhiYFP from Evrogen, see, Bolte et al. (2004) J. Cell Science 117:943-54), and m-Cherry (Shaner et al., Nature Biotechnology 22: 1567-72). The above list of selectable marker genes is not meant to be limiting. Any selectable marker gene can be used in the present embodiments.

In one embodiment, an expression cassette comprising the nucleotide sequence operably linked to a promoter that drives expression of a selective agent, signal peptide or label in the host organism, and the expression cassette further comprising an operably linked polynucleotide encoding a selective agent, signal peptide or reporter. In other embodiments, the construct used herein includes an inducible reporter gene, such as mCherry, GFP, YFP, and the like.

Kits

For use in diagnostic applications, prognostic applications, and therapy selection applications described above, kits are also disclosed herein. The kits of the invention may comprise any or all of the reagents to perform the methods described herein. In such applications the kits may include any or all of the following: assay reagents, buffers, nucleic acids that bind to at least one of the genes described herein, hybridization probes and/or primers, that specifically bind to SAILOR. In addition, the kit may include reagents such as nucleic acids, hybridization probes, or primers, that specifically bind to SATB1 exon 1d variant transcripts.

The term "kit" as used herein in the context of detection reagents, are intended to refer to such things as combinations of multiple gene transcript product detection reagents, or one or more gene transcript product detection reagents in combination with one or more other types of elements or components (e.g., other types of biochemical reagents, containers, packages such as packaging intended for commercial sale, substrates to which gene expression detection product reagents are attached, electronic hardware components, etc.).

EXAMPLES

The following examples are offered to illustrate, but not to limit, the claimed invention.

Example 1. Identification of SAILOR Expression in Breast Cancer

SATB1 is transcribed from multiple gene promoters, which generate multiple SATB1 exon 1 variants. The ATG start codon for SATB1 translation is located in exon 2, and therefore any sequence within exon 1 from any variant will not be translated.

The distal CpG island upstream relative to SATB1 exon 2 (~20 kb from exon 2, chr3:18,485,113-18,487,056; Assembly hg19; SEQ ID NO:1) contains the far distal promoter for SATB1 (exon 1d variant). The adjacent 85.8 kb lncRNA gene encodes SAILOR, which is a lncRNA that spans 1.8 kb (SEQ ID NO:2), and is transcribed in an opposite direction from the same CpG island region, either from the same far distal (1d) promoter, or from a distinct promoter that is adjacent to the 1d promoter. FIG. 1 shows a mpa of the SATB1 gene locus.

Figure 2:
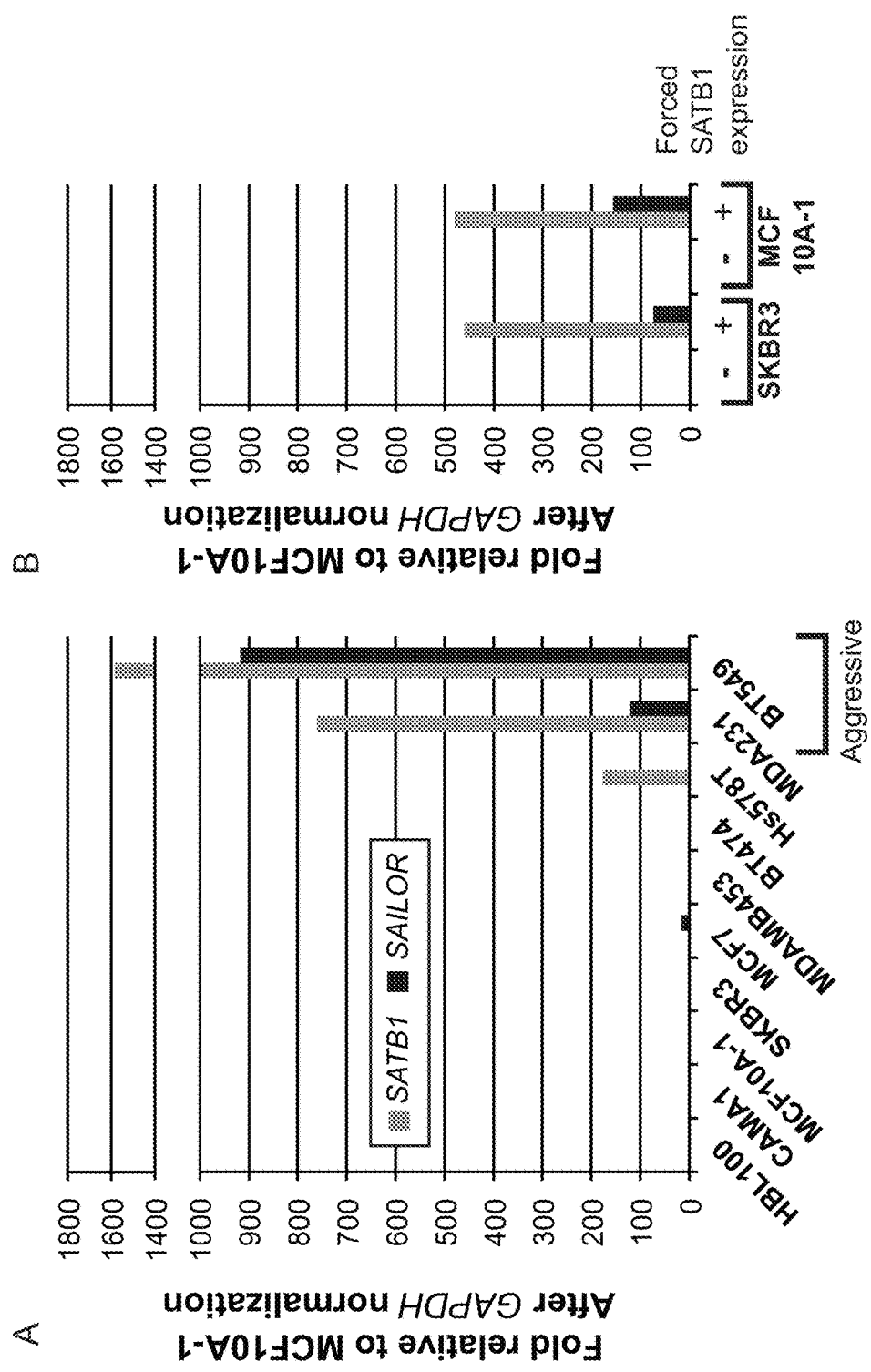
FIG. 2, panels A and B, show transcription levels of SATB1 exon 1d variant and SAILOR. (A) SATB1 exon 1 variant and SAILOR are specifically expressed in aggressive breast cancer cell lines (MDA-MB-231 and BT549). This was determined by quantitative reverse transcription (RT-) PCR with specific primers for SATB1 (one in exon 1d and the second in exon 2) and primers spanning SAILOR exon 2 and 3 to identify the transcripts. (B) Non-aggressive breast cancer cell line SKBR3 and non-tumorigenic MCF10A-1 (a variant of MCF10A, which has a low ATM level; Ordinario et al., PLoS ONE, 7(12):e51786, 2012) were either untreated (−) or forced to express SATB1 protein via the transgenic SATB1 proximal exon 1a variant (+). The data show that both SATB1 exon 1d variant and SAILOR transcription was activated by forced SATB1 protein expression. Thus, SATB1 protein can activate SAILOR transcription.

Quantitative reverse transcription (RT-) PCR based analyses of SAILOR and SATB1 transcript levels in both aggressive and non-aggressive human breast cancer cell lines have shown that SATB1 and SAILOR are each transcribed specifically in aggressive breast cancer cell lines MDA-MB-231 and BT549 (FIG. 2). The expression of transgenic SATB1 exon variant 1a in the non-aggressive SK-BR-3 and non-tumorigenic immortalized breast epithelial line MCF10A-1 was found by RT-PCR analyses to result in the activation of endogenous SATB1 exon 1d variant and SAILOR expression. The SATB1 protein therefore appears to activate the concerted transcription of SATB1 exon 1d and SAILOR from the aforementioned CpG island promoter(s). In support of this finding, SAILOR has been shown to contain long introns highly enriched in "base-unpairing regions" (BURs). BURS represent specialized genomic sequences of 200-300 bp that have a distinctive phosphate-backbone structure that is recognized by SATB1 (Bode et al., *Science,* 255:195-197, 1992; Dickson et al. *Cell,* 70:631-645, 1992). SATB1 acts to remodel the 3D organization of chromatin and regulate gene expression by binding at BURS located at target genes and tethering bound BURS to the scaffold-like matrix SATB1 forms within cell nuclei.

Figure 3:
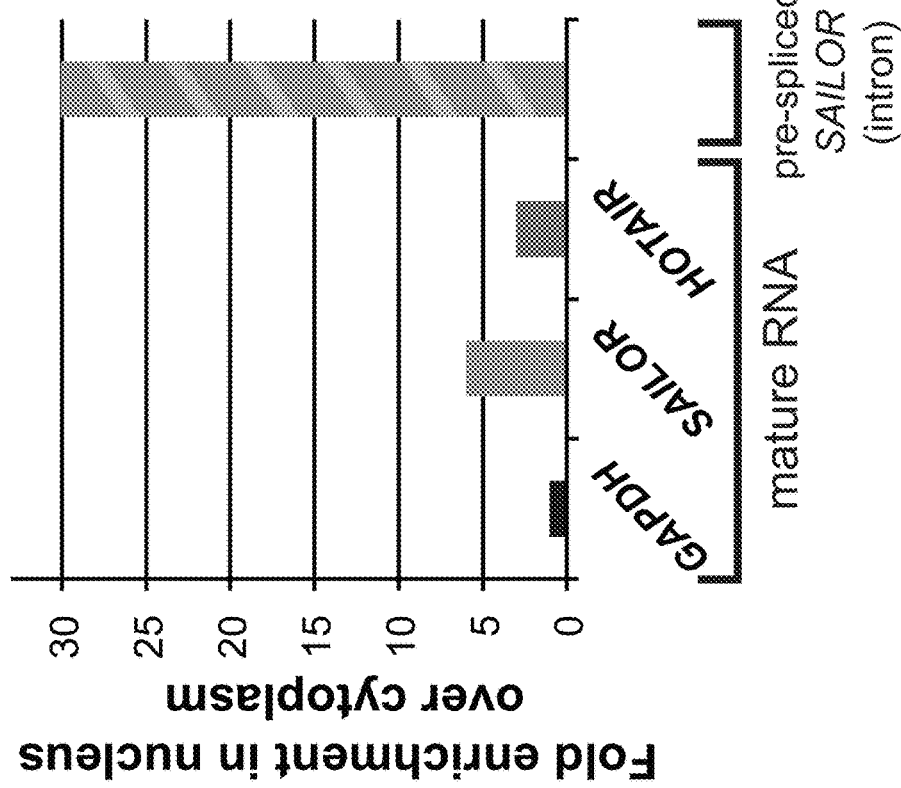
FIG. 3 shows that SAILOR is located in nuclei of aggressive breast cancer. The nuclei of BT549 cells were isolated from cytoplasm using a hypotonic swelling procedure followed by mild homogenization. Total RNA was harvested from each isolated fraction (i.e. nuclear and cytoplasm) and subjected to RT-PCR analysis using primers for SAILOR. Additional primers were used as controls: HOTAIR is a known nuclear lncRNA, GAPDH is reported to exist predominately in cytoplasmic fractions, and pre-spliced SAILOR transcript will only be found in nuclear fractions.

Furthermore, RT-PCR analysis of pre-spliced and mature SAILOR transcript levels has shown SAILOR is predominately localized within the cell nucleus as opposed to the cell cytoplasm (FIG. 3). RT-PCR analyses were performed using specific primers spanning mature, spliced SAILOR exon 2 and exon 3 (5'-GAGACTTCAGGTCAGGAAAGC-3' (SEQ ID NO:6) and 5'-CTGGGCTGTGAAATTGATACC-3' SEQ ID NO:7), and primers designed specifically for SATB1 exon 1d and exon 2 (5'-GGAGCCGTTCTTGGTTTCA-3' (SEQ Id NO:8) and 5'-TTAGACATTTCTGAATGTTC-3' (SEQ ID NO:9)). A second primer set for SATB1 exon 1d and exon 2 was also used (5'-GAGACTTCAGGTCAG-GAAAGC-3' (SEQ ID NO:10) and 5'-CTGGGCTGT-GAAATTGATACC-3' (SEQ ID NO:11)), and a pre-spliced SAILOR primer set for RT-PCR (5'-GAAGCCG-CACTTTCTTGAAT-3' (SEQ ID NO:12 and 5'-AATCTC-CCTCCTGCTTCCAT-3' (SEQ ID NO:13)).

Figure 4:
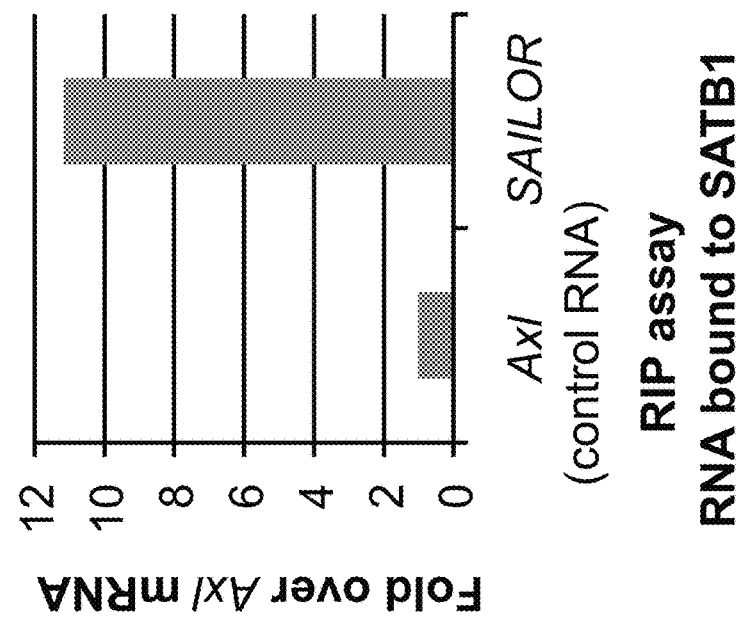
FIG. 4 shows that SAILOR is associated with SATB1 protein in BT549 cells. A RNA immunoprecipitation assay (RIP) in BT549 cells indicated that SAILOR is greatly enriched for association with SATB1 (11-fold) relative to coding mRNA AXL that is abundant in these cells, and compared to IgG and FoxP2 antibody controls that did not precipitate any RNA. This putative interaction suggests SAILOR and SATB1 share a common function.

Co-expression of SATB1 and SAILOR in nuclei of aggressive breast cancer cells suggests that these factors might physically associate. An RNA immunoprecipitation assay (RIP) in BT549 cells indicated that SAILOR is greatly enriched for association with SATB1 (11-fold) relative to coding mRNA Axl that is abundant in these cells, and compared to the IgG and FoxP2 antibody controls that did not precipitate any RNA (FIG. 4). This suggests SAILOR and SATB1 share a common function.

Figure 5:
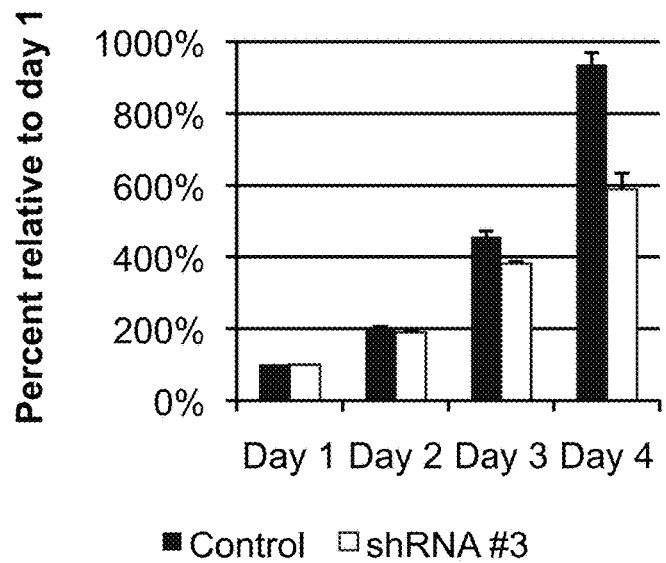
FIG. 5 shows that knock down of SAILOR slowed growth rate for BT549 cells. We have successfully knocked down SAILOR by ~80% in BT549 cell lines with a short-hairpin RNA (shRNA) approach. Reduced levels of SAILOR did not affect SATB1 transcription or protein level. However, SAILOR knockdown cells show a slowed growth rate, suggesting that reduction of the SAILOR transcript level overrides the effect of high SATB1, which promotes cancer progression.

The effect of SAILOR on the growth rate of BT549 cells was studied. SAILOR expression was reduced by ~80% in BT549 cell lines with a short-hairpin RNA (shRNA), 5'-GGTGGAAGAGTAAACTGTTCCCGAAGGAACA-GTTTACTCTTCCACC-3' (SEQ ID NO:14), which targets SAILOR exon 4 at sequence GGTGGAAGAGTAAACT-GTTCC (SEQ ID NO:15) (FIG. 5). Reduced levels of SAILOR did not affect SATB1 transcription or protein level. However, SAILOR knockdown cells show a slowed growth rate, suggesting that the aggressive cancer properties of BT549 cells are attenuated when SAILOR is reduced.

Figure 6:
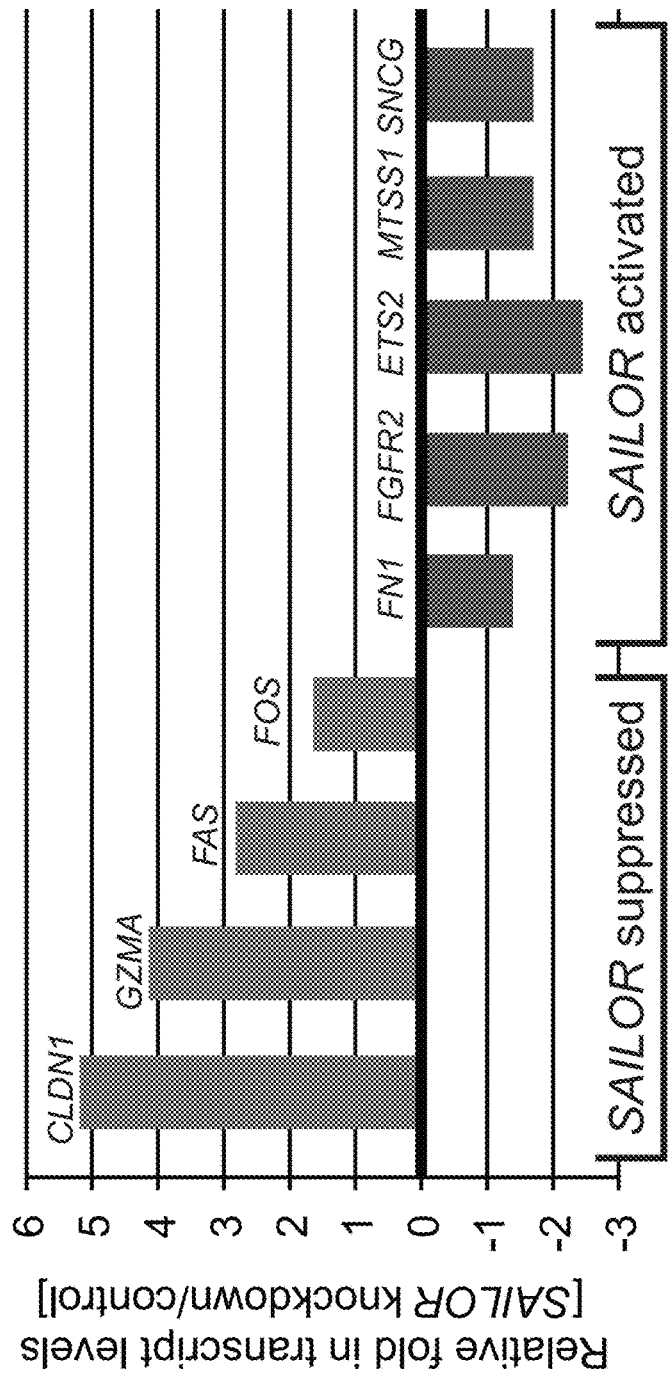
FIG. 6 shows that knockdown of SAILOR leads to changes in transcription levels of some specific genes known to be SATB1 targets, such as Claudin1 (CLDN1; repressed by SATB1) and fibronectin 1 (FN1; activated by SATB1). Expression of these genes was altered in the same direction when either SATB1 or SAILOR was knocked down. Therefore, at least with a small number of genes found to be SAILOR-dependent (~10% of 85 genes), SAILOR seems to affect gene expression toward cancer progression.

The role of SAILOR on transcription of some genes known as SATB1 targets in breast cancer was also evaluated. Trancript levels of Claudin1 (CLDN1; repressed by SATB1) and fibronectin 1 (FN1; activated by SATB1) were altered in the same direction when SAILOR was knocked down (FIG. 6). Therefore, based on the small but important number of genes found to be SAILOR-dependent (~10% of 85 genes in a Cancer Pathway Superarray RT-PCR assay), SAILOR seems to affect gene expression toward cancer progression.

Figure 7:
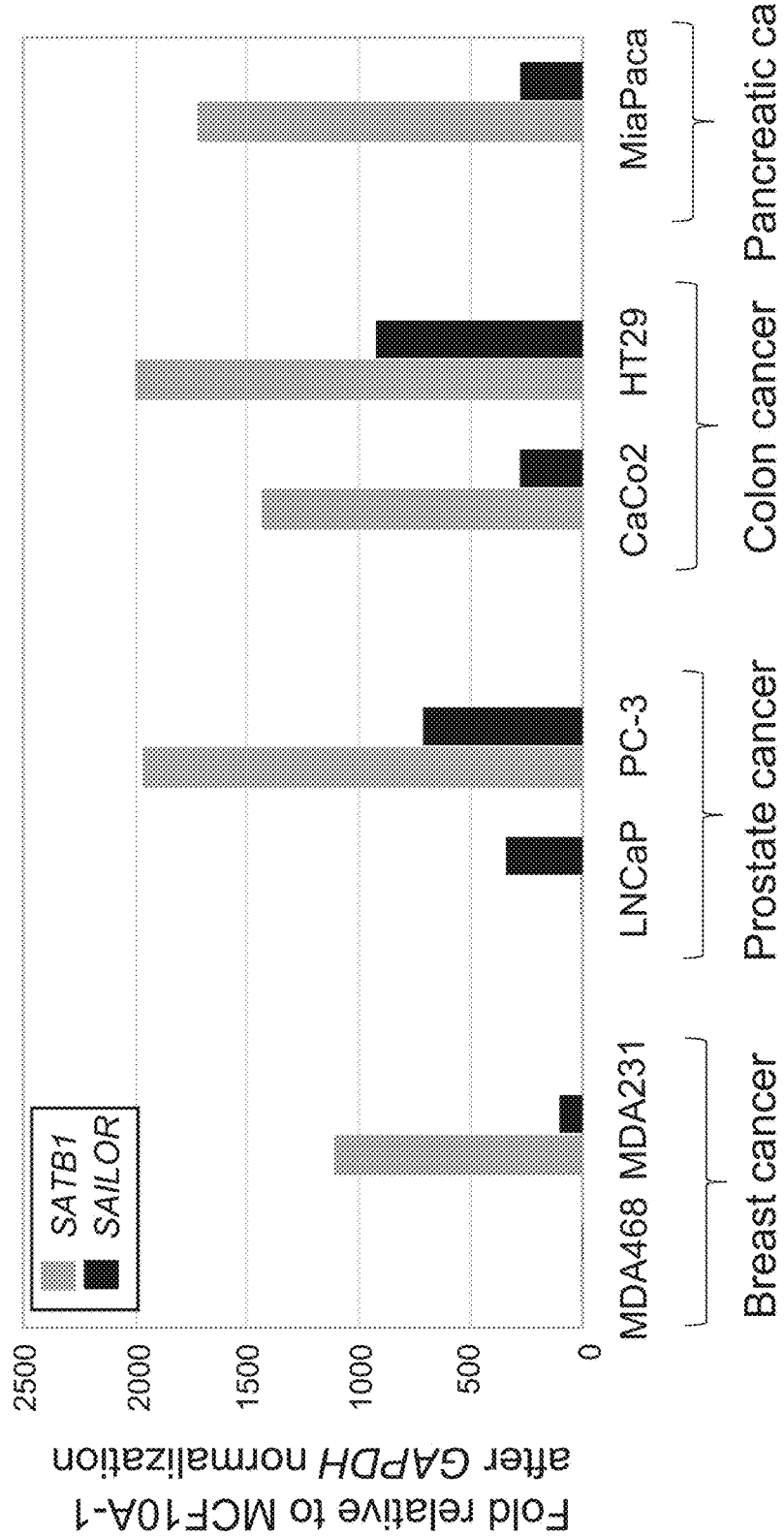
FIG. 7 shows that the expression level of SATB1 and SAILOR transcripts increased in aggressive types of cancer cells, as determined by qRT-PCR performed in non-aggressive cancer cells (MDA-MB-468, LNCaP, and CaCo2) versus aggressive cancer cells (MDA-MB-231, PC-3, HT29, and MiaPaca) from breast, prostate, colon, and pancreatic cancers.

High transcript expression levels of SATB1 and SAILOR were not restricted to breast cancer cells. High expression of these factors also occurs in pancreatic cancer, prostate cancer, and colon cancer cell lines (FIG. 7). Importantly, within each of these cancer lines, expression was found to be more highly present in the aggressive cancer form (e.g., higher in HT29 cells from colon) relative to non-aggressive cancer from. These data indicates that the link between aggressive cancer phenotypes and elevated SAILOR lncRNA expression is not limited to breast cancer.

When the non-aggressive breast cancer line MCF10A was exposed to chemotherapeutic drugs, surviving cells showed a greatly up-regulated expression of SATB1 relative to the initial cancer cell line population (FIG. 8A). Furthermore, the forced over-expression of SATB1 resulted in an increased resistance to a wide range of cancer drugs, indicated by the need for a higher dose to achieve 50% cell death in culture (FIG. 8B). These data indicate that cells that evade typical treatments are those that already expression SATB1 at high levels or that up-regulate SATB1, and in doing so evade cancer cell death. In either case, these findings are indicative that detection of elevated SATB1, and by association SAILOR, in a patient during treatment may faithfully identify a cancer that has acquired resistance to the treatment.

Figure 9:
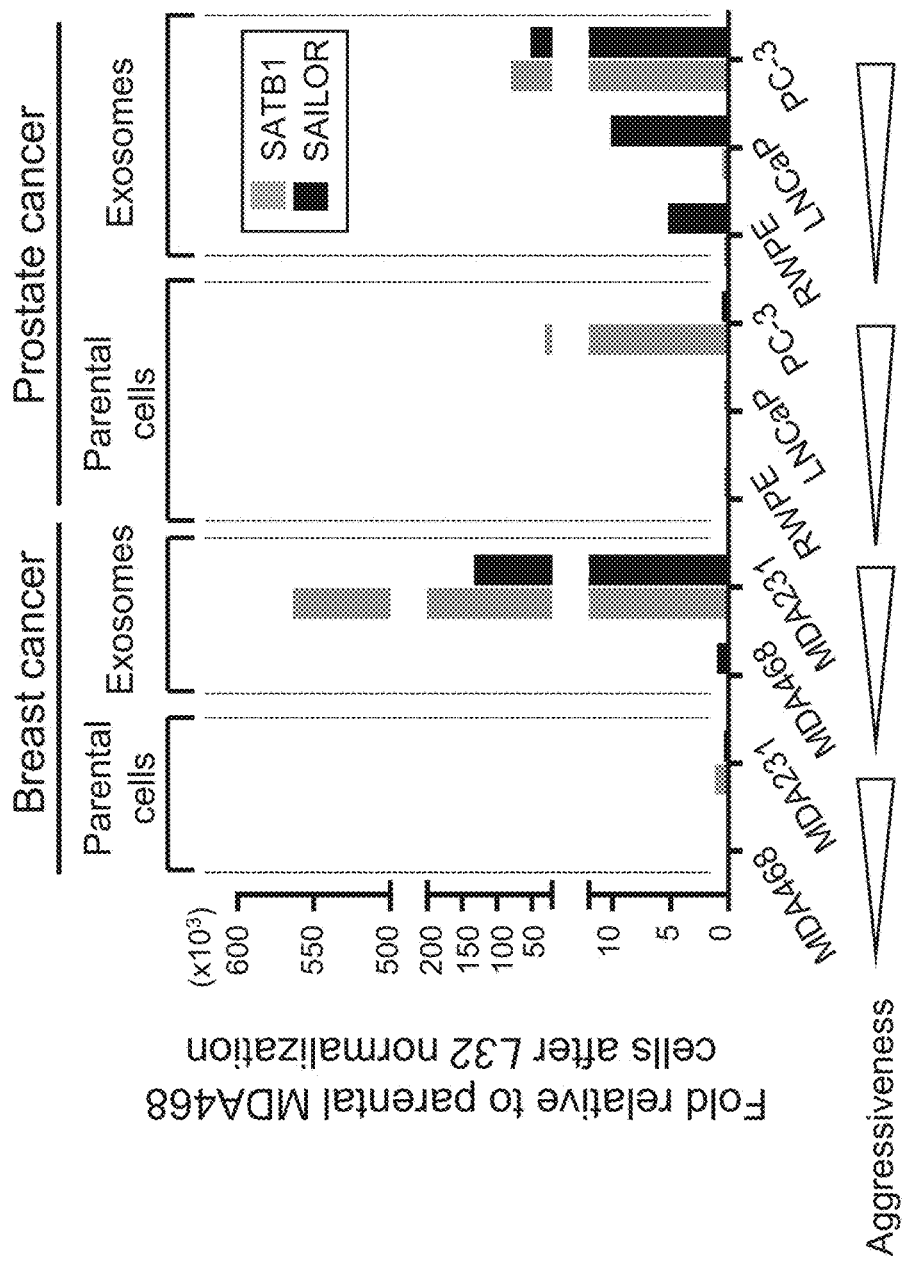
FIG. 9 shows that SATB1 and SAILOR transcripts were present in exosomes (circulating extracellular vesicles), and the abundance of transcripts was proportional to aggressiveness of the cancer cell type. Endogenous SATB1 and SAILOR transcripts within a cell population (control breast cancer cell lines; MDA-MB-468 and MDA-MB-231), and those transcripts in exosomes isolated from conditional medium of each of breast cancer cell line and prostate cancer cell line, were detected by qRT-PCR

Exosomes from cancer cells were also evaluated. SATB1 and SAILOR transcripts are quite abundant in exosomes from cancer cells when purified either using a commercial kit or centrifugation. The level of SATB1 and SAILOR transcripts detected in exosomes was proportional to aggressiveness of the cancer cells (FIG. 9).

These data suggest that SAILOR is an important factor for the metastatic potential of tumor cells and that SAILOR and SATB1 are co-expressed specifically in aggressive tumor cells in human primary tumor specimens. High levels of SAILOR and SATB1 exon 1d variant transcripts will predict metastasis and correlate with shorter survival times. SAILOR transcript levels alone can serve as a prognostic marker. Determination of RNA levels for both SATB1 exon 1d variant can also be used.

The present examples, methods, procedures, specific compounds, and molecules are meant to exemplify and illustrate the invention, and should in no way be seen as limiting the scope of the invention. Any patents, publications, and publicly available sequences mentioned in this specification are indicative of levels of those skilled in the art to which the invention pertains, and are hereby incorporated by reference to the same extent as if each was specifically and individually incorporated by reference in the context in the application for which they are cited.

```
Illustrative Sequences-All sequences are shown 5'
                    to 3'

SEQ ID NO: 1
CpG island
>hg19_dna range = chr3: 18485113-18487056
CGTTTCCCCAGTAAGCACGTGGCACTCCCCGGACCTGCCACCTGCCTGCT
TCGTCCTTCTCGTCGTGGTTTCCCAAACCCCGGTTCTGCCGGCCCGGGAG
CCTTAGCACTGGAGCAATAGGAAAAGGCCACCGCGCTCGGGTCTGGACAG
CAGGAGGGAAACACGGTGTGGACTGCGAGGCTGCACCTGTGATGTCCCGG
CCCCTGCTAAGAGGACGGCCCTTTCTTCTGCCTCTTGCCCAACTCCAAAC
CCACATTCACGCCAGCAGCCTCTCCAGGACCGGCCTCGCTACAGCCAGCG
AGGGCTCGAAATGAGGAGTGCCGCGGCTTTCAAACTCCGGGCTCCAACTT
GAGCGCCCCGGCGCCCGAGTAGCTCCCGGGATGCAGAAGTTGCCACAAAC
TTCCCAGGCCCCTCTTCGCCGATGCTTACAATCAGCCGCGCAGGCAGGGA
GCGGAGGGAGGCGGAGATGGACCGGGAAAGGATGCTGAGCAGACTCGCGA
TCCGGTGGGGGAACATTACCACTCCCGCAGCCCACTCCTCCAGGCACCTT
ACTGCCCGCCCGGCTCCAGAACGCACCGAGAGGCTCCCCTTTTCCCCATT
TGCTTCCTTCGGTCTTTTCCACTCCCCTTTCCTTTTCTAAAAGGGGCCAT
ACCGGTGACCTGAAGGAGTTTGTTCAGCCAGGGTCTATTGGGCAGGTGTG
GTGGTGTGTCCACACCCAGACAGAAAACGAATGGCATCTTCAAATCCCCC
ATCCCGACCGCTCTCCCCTACTCTACCAGCCCACCCCTCCAAGGTCCGTC
TGCGTGAGAAAAGGGGCTCGGAAGACCGTTGAAGCCCTGCGCCCACGAGA
GGGGAGCCCAGCCGCCCCAATAGGGGACGAGGAGTGGGTGCTACGGAGAA
GTTTGGATTGATTCCGGAAAAAGAGGGACAGAGATAAAACAGCAAGAGTA
GCAAGGGGAAAAGGGAGGCAAAAGAGCAGAACTCACTCAGGCATGGACGT
TGGGGGCGGCGGTGGCTGCGAGTGCGGGCCTGAAACCAAGAACGGCTCC
CCGGGCGGGCGCGCCGGCGTCGGACTTCCGAGGCGGCGGCTTCTGCCTCT
CCTGCCGCCGCCGCCGCCGCCGGAGCTGCGGCTGCCGCGGAAGTTAATTG
CAACTTGACTTCAAGTTGTCCTCTTTCCCCATACGAAGTGGGCGTTTAAA
GGGGAGAGCGAGGCGAGGAGCGAGCGAGCGAGCGCGCGGGGCCAAGGGAA
GGAAGAGAAGGAGGGGGAGGGAGGAGGATGTTAACGGGCGGGGGGGGAGA
AGGGGGAGGGGGCGGCGGCGGGGGCGGGAGGGGGAAGGGGCCGGCGGGAG
CTGCTCTCGTCTCGTCGGTCGCGGCGCCTGCAGTCTGGAGGCGCACCGGA
GCGGCCGGGGCGTCCCCCGCGGGAGCCCGCAGCCACCCGGGACGCGCATC
CAGACGTGGCGCTTCGGACCGGGCACGCTGCGCCCGGGGCTCGGCGGAC
CCCGCGTAGCCGCCGCTTCGGAGCTTGTCGGCGCGGGCTGGCCAGCGGG
GCGGCCAGGGCCCGGCCCGCCTCCCAGCGCCCGCCCGGCTTCTCCCCCT
GGCGGTGGGAGCCTCGGCGGCCGCTGGCGACACTAGGCGCACTGAAGCCC
GAGCCGAGCCGAGCCCGAGCCGCCGCCGCCGCCGCCGCTGCTGCGCACCG
CTCCCGGGCTCCCTCCCAGCGCGCCGGCCGGGGTGTGGGGGGCGGCGGGC
CGGAGGGGCGAGGGCGGGCCAGGGGGCGCACACGGGGGTTGGCGCGGAAG
ACAGGACCCTCAGCCTCGAGGGGTAAGTGTGGGCGCTTGGGGGTGCGCTT
GGGGTGCGCGGCGCGGTTCTCGTCGCCCGCCAACCCTGCCCCCTCACCTC
TCCGGGGCCCCCAACACGCGCACTCCTCCTCTTGTCGCCTGCG SEQ ID NO: 2
Canonical SAILOR lncRNA sequence after transcript
splicing
>NR_125803.1 (SATB1-AS1)
gcggccgctggcgacactaggcgcactgaagcccgagccgagccgagccc
gagccgccgccgccgccgccgctgctgcgcaccgctcccgggctccctcc
cagcgcgccggccggggtgtgggggcggcgggcccggaggggcgagggcg
ggccaggggcgcacacgggggttggcgcggaagacaggaccctcagcct
cgagggagccctaggtgaccaggcaaaatggcagttccttccagctggt
cctcagatgggcacatctattagcctctgctcttgtaagaagttagctgc
agaacccacatgtgaatccttgtaggactctggagaagatcaaatgggag
cttagatgtggaagctctttggaaaccaagaaacactctgaaaatgaaaa
gggtggaagagtaaactgttcctgtttctccatcttgacaggaagcagaa
gttctccttagctgattttcttcttgccttatactgggttctttaacac
cagaacaaaaataaataaataaaagaatcttccagaaattcatgaagaga
```

| Illustrative Sequences-All sequences are shown 5' to 3' |
|---|
| cttcaggtcaggaaagcctgaactttctcatccaacacccgttcaagtcg gaggatgctgattaattcatgatggaaaggtatcaatttcacagcccaga cctctacattcttgaaatgctcttctcatgggagacattaaataagcttt gaattaactgagacctctgtggattctataactcaaagacccaggctgac ggctggtggaatagctaccatctcaaacatggcgtgatgctgcatcagag agaaaaataagctcttgcattgacaatgaaatgtctaccctgt |
| SEQ ID NO: 3 A transcript variant with an extended 5' end and a truncated 3' end *** Underlined sequence is the target of shRNA to reduce SAILOR levels<br>>TCONS_12_00019762<br>gccggggcgtccccgcgggagcccgcagccaccgggacgcgcatccaa acgtggcgcttcggaccgggcacgctgcgcccggggctcggcggaccc gcgtagccgccgcttcggagcttgtgcggcgcgggctggccagcgggcg gccagggccgccgcctcccagcgcccgcccggcttctcccctggc ggtgggagcctcggcggccgctggcgacactaggcgcactgaagcccgag ccgagccgagcccgagccgccgccgccgccgcgctgctgcgcaccgctc ccgggctccctcccagccgcccggccggggtgtggggggcggcgggccg aggggcgagggcggccaggggggcgcacacggggttggcgcggaagaca ggaccctcagcctcgagggagcccctaggtgaccaggcaaaatggcagtt ccttccagctggtcctcagatgggcacatctattagcctctgctcttgta agaagttagctgcagaacccacatgtgaatccttgtaggactgtggtgtgc gatcaaatgggagcttagatgtggaagctcttttggaaaccaagaaacact ctgaaaatgaaaaggggtggaagagtaaactgttcctgtttctccatcttg acaggaagcagaagttctccttagctgattttctcttcttgccttatactg ggttctttaacaccagaacaaaaataaaataaaa |
| SEQ ID NO: 4<br>Long non-coding RNA (unspliced) (identification TCONS_12_00018460, TCONS_12_00018461, SATB1-AS1)<br>>hg19_dna range = ch3: 1846850-18572715<br>GCGGCCGCTGGCGACACTAGGCGCACTGAAGCCCGAGCCGAGCCGAGCCC GAGCCGCCGCCGCCGCCGCCGCTGCTGCGCACCGCTCCCGGGCTCCCTCC CAGCGCGCCGGCCGGGGTGTGGGGGGCGGCGGGCCGGAGGGGCGAGGGCG GGCCAGGGGGCGCACACGGGGGTTGGCGCGGAAGACAGGACCCTCAGCCT CGAGGGgtaagtgtgggcgcttgggggtgcgcttggggtgcgcggcgcgg ttctcgtcgcccgcaaccctgccccctcacctctccggggggccccaac acgcgcactcctcctcttgtcgcctgcggcttcctcttgttgcttgttgt ttggctgggttttgggggggtgagtagagggggttactgtagtgtgtgc aggcggaggaggaagtcaggtgagaggccgcgaagcaccccaccccaac ccagcctgcgtgggggtgtatgcttcccccactaggggcatttgggccattt tttttttctccgtcaatgttcggtcgagacgatgtttcctagagggcctc cttcacttacagtctggtctgcctcctcatcccaccctcgtccg tcttagcccccttgtccaggagcctgcaccccaagtgaggagcacgtggc ggaaggaggaggaggccctcttgaagaccccacgctgtgacccagcc cattagttaaatatttatcctcacatcaccagctgtacttttcaaccca ctgaaacaagacgcctaggcaagttccaatttccccaaaaagctgggcc aaagcggagagatgagggttttattgacattgggagagaaggggccaag gaaccttccaagtggagactgaaactcaaaaaatctctacaaaaagact agggtgactggaggctcaggactgcaggcttaggagaaactggagctcca tcaactttatttctctcccctgcctctcctccccccagcctgtgaggaag ctaacaggtcttttgtttttgtattgtgtagcctttgggaaatttgcattg agtatgtcaacagaaaattactactgtttactcaaagggattgcagaaag ataaaacatagtaacatagtttttactttcctcttcttgtacgcttgt gtgtatttggcaagaagtgtagttaggttcatggcatgaactgcaaaacg tcaggttgtaacataaggactgtagagctgcctaggtgtattttttagaa gccgcactttcttgaattcctttcacacaaggcttgctctctcattaagt ccccataaaatttattaggagaggggaaactatggaagcaggaggg agattgctaagatttccatcctgccagcgcacagcactgtttgcagggaa gttcctggaaagtgattgtgggctgaagattcagttttttcctaaaagctc tgttaggtcctgttgtgtcagatggctatgaataaagcacgctgggaaaa tcctgatatccgtcagtcttatttttatcttttacacagtggttgattcg actttcaagcccctggtgacaaacacatcaactctgctgtatttttgtgtg ctttttctaaataaaggagaataacagcatgtattcatgtgctttttcc cctcatccatggttattgaattcactggaagttattcatctttttcagt tgatcatcattttatgccgagaccacaattccaaacatataggaatttt taaaattatgaattagggttctttagggaaccaaccctccttttaaag atacaagtgcccaccacaactcctagttttgtaaagcaaagcaaaaaggt ataatgattataatgagcaaaacatagtaaaacgttttccttcttggat cacttttctgtcccaacagtccaggagacattaaaatcctcctgccttaa tttaccaaaatgctgcatttctaaccagtacaatatctgtgtctgaga aagacatcaggtttggaatggaaaaaaatacattctcggtattaattac tgcttaacagtaattattgtagcaggcagttgattttccaattctgaaa gcctgaaatgaagctgaacagaattgaattttttaaaaaaggtttttt tttcttttcttacactcttatatactcatctgcttccccaagttatcagcc | aagccccctataactgaaagtatgatatgctcctctgagttgaaccgagac cattttgcccctcatttttttgaagttgcttttttcctcccaataagctcttgt atagaaagcacatgggctctgttagaatacagaattatgcaattctgggt gcagtgcattaaatgacatagtttgataaactcttaagccttacagctca gatgttaataaaatattgtagttggccacaaaatttcatagcacaaggcta agatcattttcagaagaaaggggcatttaatctggattatttggttagt tgctatggtctgaatgttagtgttcccccaatattggggttcatgtgtta gaacctaatatcaaaagtgatggtattaagaagtagggcctttgggaagt gattaagtcatgaaggcttcaaccctcatgagtgacaggagtgcctttgt aagacaggctgaatctagctaccttgccccttccactgtgtgaggacaca gcaaccaaaagtgccatctgtgaagcaaggagtgagccttcaccagatact gaatctgctggtgctgtaatcttggactcctcagcttccagaactgtgag caataaatttctgttgcttataaattacccagtcaaagataaatttgttgt agcacctcaaatgaactaacacaataatacatttgtgctactagatttttt ttaacaagtccaaatgtgacttaaatgactgaaagacaaatctggaacat atcaaatggccaataatagtagctggtatcaaaagctgcactggttattt ccttaaaagaatagacaataaaatattgcctactaaatattagaagaaag atcaagggaaaggataaaacagcattggccttgaaggaagttatttgctg gaaaaaagacatcaaaatgtgaaaagacaatggatcagttagtggtttga atcaaagaaatacttgaggaagaaaaaaatatatatatatatgtacatatt tttctcttaagaccagaggaatcagagatcctaaagctctaggttggaag gtattttaaagttaatttgttctgtcaaatcttagaggccattcaatg cagatattttgggtgtgaagggaacttactacttaccgccattaaggca aggattttttacctataccgtacttaccagagaatagagtttcactatatat tgtgcaagtgaatggataatttcaaaagtattttcatctttatatacttta ttatgttttttaccttatatatattttttaccttatattgcacagaatta gtcttcctgaaacttccaaccgtttagtcttcgtcctgccagttgcagcca aacagaacaaaatttgtttatcagtcaagataggcaatgtgctggagtaac aattccaattttttagtggcctgtaacagcaaacgttttcttggttatgg tttgaatccattgcagttcagctggtctgttccatgtctgtcactccagg tccctggctaatggaacagttgccatcttgaatgttttcatgttgttatgg caaaaataagatcactctggagtttcatgcagcaatttaaatgctat ggcccagaaatgccatcatcatatggcctcacaaagaattaaccaggat tagttgtgtggctccaaagaatcatgacaagaaggtcggatagtgcagcc tatcttgtacccaacagtagagagctgtggtacacaattctgcagactac tgctactggtagtaatccttgtccatatgataacctgccagctaaacaggt ctcttcctgtagctttttatggcccaagtcttccattttttagggcaaactg ccagatagccaccagcttagagggaaacattgttatcaggggaacccgc cccaatatttcaacatagattctttatatttttccctaagtgtcggccag tctgagcaataaagagaaagaattaaagagaagaaaatttttacagctggc cgctggggatgacatcacatatcagtagatccgtgatgcccacctgagct gcaaaacctgcaagttttttattagggattcaaaaggggaaggtgtgtat gaacaggagtaggtcacaaagatcacctgcttcaaagggcaaaaggcag agcaaagatcacatgctctgaggaaacaggaccagagcaaaatcagaaa ctcctgataaggtctatattcagcggtcacgtattgtgtcttgataaaca tcttaacagaaaacagggttcgagagcagagaaccggtctgacctcaaat ttaccagggctggtgttcccaatcctagtaagcctgagggtactgcagg agaccagggcatatctcagtccttatctcaaccacataggacagacactc ccggagtggccatttgtagacctccccccaggaatgcaattcttttcctaa gggtcttaatattatattccttgctaggaaaagaatttagcgatatctct cctacttgcacatctgtttataggctctctgcaagaagaaaaatatggct cttttttcccaacccccacaggcagtcagacttacagttgtcttccctg ttcccctgaaaattgctgttactccgttcttttttcaaggtgcagtgattc acattgttcaagcacacatgttttacaatcaatttgtcagtttaacaca atagtggtcctgaggtgatgtacattctcagcttacgaagataacaggat taagagattaaagacaggctaagaagttataaaagtattaaattttggga actgataaaatgtccatgaaatcttcacaatttatgttcagagattgcagt aaagacaggtgtaagaaattataaaactattaattttgggaactgatatg tgtccatatttaaagtgaaatcttcacaatttatgttcctctgctgtgact ccagccagtccctctgtttggggtccctgacttcctgcaacacattgtgt gacttctttactctctactgtctcttttgaatgcaacactaacactcct gtacccctagaaccccctaacaaagtggcctcttatccaattttatgtca ctcttttatatttactaatattatacattgtattttctcaggacttat tttcctggcaagggtataataaacaggcatttttaacaactgttttctga aaatgtcatggtcattatcaaaatttgaaattttggtctgagtagctactt ccctttgttgaacatcaaatgtgttatatgattttgtaacacaaattt aaaaatcctcattcattcatttatcctacttttgttcattcaataaata ttcattttctacctagtagaaggcaggcactcttttaaggattgggata tggagatgattaagagttctcctcttcaagaaacacattttctgattggg cagacagaattaaaagtcattataatgctaatagaagcacaaagtgttat gtgaacattagaaaagacaaaagctagctggcaggattttagaaagt tccatagaggaattgacacttaaactaagtcttgaggataagtgagactt ctccaggcagaaagaggagggagagagggatatttcaaccaaggagacc agcatggacaaaggcactgaacatgacaaagcttattgtttatggaactg taaggaattcagtgaggctggcgcatgggtctttgtaaaggctgaaaat tctgaagggccttgcagacattctctggagttttggacattatcccataca |

| Illustrative Sequences-All sequences are shown 5' to 3' |
|---|
| tcaggaactgcaaactcttatgtctaccttgggccatgcatggatgtaca
tgactaaagcagaccaagttaagactataagcagtcgtggggctggca
atgtgaagaatatatcctctgtccaaatgggatagtaaatgccattggtg
cctccattctccaaagaaaagcaggaaatttagatgtatatgaaaaattg
aatattaaatgttgtcaacttatccatatttttgaagtacactgttagtcc
ttaagctaattttttgacctacagacaaattttgtatagcttttgcatgtat
atttctactgaaggtcaaagtgtttataccccattggagaatagtagccac
tctttatctgcaagttatatgttccaagatccccagtggatacctgaaac
tgtggatagtactgaactgtatgtatactgttttgtcctatacatgcata
cctgtgatgaagtttaatttataaattaggcaaagtaagatattactaac
aatagctaataataaaattgaatagttatgatacactgtaataaaagaga
ctatgatctctctcttttcaaagttatcttattacactgtactcacctatt
ttcagactgcaattgacctcaggtaactgaaactccagaagagaaacctc
aaataaaggaagactattgcctgttttatctcaacctatcccatagccat
gtgcctaaggactgtcttgaggatatttaatttttgtcattttttttaatt
gagtccactaattacttactcttcctagctgctctcttgctttcatgcca
gacttgctgccactcaatagtcagaaatatgcagcaacaccccacacttt
cctatagcaattataatgttagaaatactaggtatcctttcataacgcat
gctgaccattttcttgtagattttggtcccatgggtacatccagatttta
aagtcattcaattcactgggccatcaggtctttaagttcttgacaacttg
gctgtacagattacaaattttattcgatcttcttgactgaaagaaagtca
acgttcctgggtgtgttttgtctaacttataaacaataacaatcatccatt
ttatgtgttctgtgagttttgaatatgaaggggcagcatgagcaaattat
attttatgtgaactttgaagtaaataaatatatctaggcaaagccacttt
aggtgtccaactgtctggattctaatcctggttcaattagttgctaccta
tatgacctagagcaaatctcctaatttctttatgcctcaatttcctcatc
catgttacagggatgctaatagttagtagatggggttagtaggtgcaagg
tgcttcagaatagaaaaatgaatttactaggatgtaagtgggatataagt
acttaactcctggatgacatgatgttgtgctgggggtacacaagccaaag
aagaattatggcttctatttctggaatatttatttttttacttgaggattt
tagaaattatttcttatgaaaacagtgacacatataatggaattaactg
tagcattttgcatgaatttttaaagaaaaacaagagtctttaaagatcttt
cagctgcttcggatttttggggggaagaatgggaactgcatttttcttcctt
ttgctgcactctctcctttatcaggttggtggaaatgcttatgattagca
gaccatatacactagttacattagttacattttgcctcaaaactgtgaaag
tacctcctgtatttatgtgctatgaagtgctgcccaagtgcagaatctttg
ccatttaaatgttcagatttttaaaccagaaatgtgttgggtaaagaaga
aaattattagagcatgaccttagggaaatcaagtcacaaaaagaaaaga
gctgaactgaattctatttcccattctgttactaaccagctggcttatta
atgtccataaagagagaggatttttgtccttttcactgataactcccaca
ccttgaataaaatagataatgttgaatgatcttggaaagacactttgtta
aagtctcagtttcctcagctgcaaaacaaagatgtgatcttaaacttaaa
ctttattgtgtatggaattaaatagagtttttgtttaaaatgcaggttct
ttgagtccatgcccagaaatttcagatttggtagaaccagatgctattcag
caatccacatggattgggggcttgggttgtaaggagcaaaaattccaactt
aaaaagaaaggttttatttttttattttgcttcattttttgtcccccctct
cttccctccccgcacataaattggaaaatacaatgcaaggactgcttaa
ggcataattagatctagctgttcaaataatgtcaccaaccatcttttctt
tatgcttcttctctcttttaacttttatacttagtctggttttttcctttaag
gagttcatttttaagaacttcattcttaatctgccttttctcctagcttc
cattcttctgacatagaaacccagcacaaagagtattccttttttctcaa
attttccagctaaagaaactacacccaacttgactgctattagattatgtc
aggtacccgtacctgcactcatccaccatggtcagcacctgtgattcacac
ctcagcagccttgagtcaaatgcccacccttggatttgggagtacagtcac
tcaactcaaaccatgtgggcttggacgtgaaggtgggatggttctccaag
acaaattggaaattaattttttagaaataaggaaaaatgggtgcttttag
ccaaaactatagatctccttccactactgagcattttaagacgtatttta
gagatgaatgatccaaaaatgttacaaaaatataaccagtattccaagac
attgaggcattcagccctcaatgtgacaaagcaggggctgagaagtacct
aagatggtcacagtcccagtgccaggtgcctcacctatttacctcagtgt
ttgggaaaatattaagtattttccacgtgttattgtattagttttcaca
ctgccataaaaatacctgagactgggtaatttataaagaacagaggttt
aattgctcacagttccacatggctgggagaggcctcaggaaacttacagt
catggcagaaggcaaagggaaagcaagacatgtcttacgtggcagcacga
gagagagagagagcaagcgaggaactgccatacacttttaaaccatca
gatatcatcagatcttgagacagcactaggggatggtgctaaaccatta
aaaccacccccatgatccagtcatctcccaccaggtcccacgttcaactt
gtggggattacaatttgacatgagatttgggtggggacacagagcaaaac
catatcagctatgaaggtgatctatgtgcaggtgaactgtgacttgtgct
atgggacagtggattttgagaatcagtcaaaatcattattgttatgtt
tgacatgacattttgaagtcattcaggcatacaataatagtactactct
aggatcttcatgacataacctggaagttggttgatgcaattgaaaagaca
aagccctagtacaaaaaaaatgggacaaagaaacaggcaggaccagcaa
ttaaatcttgctttgatttggttatcagtttgtgtttattttaataatctt
ggacaaatgtattcatctaatgaatacagcccccagcctggatcccagcat
gcctggttccaattaatgtttgaaacataatggatacatgctatacagat | aatgaaaggggtaagcaggcaacagtgtggaagacaaaactgagttgac
ttagttatcagatagggtcttaggtgtattacatgcgagttcatggaagta
aattccggatgaatgaattattaaccccctatttttgttaagtgaagaagct
gctatcatttccttaagctcattaatacaattaataaaaatgtct
acctcttcattttagtattaagtcattagtttagtttcagatgcttttcc
atacccttgccccactgttaccttcaccaaagtaatccaatgtgcagaga
aaagtgttttcaacaaataatgctggaataaatagatatccacgtgggaa
aacaaaacaacatttatccatatcataccatacacaaaattcatttgcaa
tggattatagatccaaatgtagaaggtacaagtataaagcttttataggg
aaacataatgtaaattgtagatagacaaagattcttagatgagccatag
aaaacaataaccataaaataaaaaataggtaaattacatgttaaaatgta
aaacttagcataatggcatgtgcctgtagtcccagctacccaggaggctg
aggcaggaggatcccctttagctcaggagttcaagtcaagccggggcatca
tagcaagactgcatttctatgattaattaattaaaaagttatgtttaaag
aaaagcagagtgaggagtgatatctgaaattccttattaaacaaacatt
actactagaaggatttcctctcttgtgcatttagttcaagttttttgttt
gttttgttttgttgttttgagacaggggctccactctatcacccaggct
gcagtcagtgatagaagctgactctgtgagcttaagcaaagcacatggg
ggattttcaataccaaaatcagggatgcaatggagcctaagaataag
aagaactggctcggcacagtggctcacgcctgtaatcccagcactttggg
aggccgaggtgggcggatcatgaggcaggagattgagaccatcctggcc
aacatggtgaaaacctgtctctactaaaaatacaaaaattcagctgggcgt
ggtggcacacacctgtagtcccagctacttgggaggctggcaggagaa
tcacttgaacctgggaggcggaggttgcagtaagccaagattgcaccact
gcactccagcctgggtgagagagagagactctgtctcaaaaaaaaaaaaa
aaaaaaaaaagaatagaagaactattgaagtgctatagggaaccaagtca
attctttctctccatatctcatcttttgtctttcttcctcagagtagtcca
gctccctgcctcctcagttcacacagtgaatcatggtttctaattgttct
tgagccattttcagtcagtccaccctgagaaaggaccatcttcctgtctt
tcacaattctcagggaagagtctgattggcctgcttgggtccagtgacca
cccttattccaataagctgtgaccagaggcaggatgatgtttaaagaaac
atagcatttttctttcatctcttgtaatgtggagtgaaaagaaattgcatc
acagttgagatccactgtacatttactcttcattagacatgagacagagt
tcacaaaaattttgcatttggtcacagttttaatggcaacaattattgt
tgtgttggtttttacttttttgattatctaatatcggcatctcctctct
gcatatctatgtattgactaatacatattaagggccataaacaaagatgg
ttcatttttagaaatgggcacatttgtttataaattattagccaagatcta
ttcaaatccagacatgatttgttctagtctggatatacaataaaattaat
ttaaataattttaatcaactcaaaaacagcaaattccaagacaattagg
ataacttttaagaactcatattttattgagttaacagatggtaaattaaaaa
acaatgaagctaattttttaaaatcattcattgaattaaaaaatagactta
tttaacaaaactgtttttaagctgcttttttatcctaatatgcatgtttt
aagattccaatttgggggactctagaaagacgcagagtgagtttcagtat
atgaacactcttctactgagttacttttttaaaagcttcagaatcatctga
aaaaaaaactatcaacaataaaatataagaaataagaatatttcagtta
ttggaagggatggagggtttgcttcttcaattccagttttgcttgctaaca
tggtcctatggtgtattagtttgttttcacactgctgatgaagacatacc
tgagactggcaatttacaaaagaaagggtttaattgaacttacagttc
catggcagtcagggaagcctcacgattatggtagaaggcaaggaagagcaa
gtcatgtcttcatggatggcagcaggcaaagagagagaacttgtgcagg
ggaactcctcttttttgtgagacttattcactatcaggagaacagcatgg
gaaagacttgccccagtgattcaattccctcctaccaggttcctcccaca
acatgtgaaaattcaagatgagattttgggtggagacacagccaaaccctc
tcatatggtcttctgtatttctgaccttgaaatatcttgagagtttcctc
tgctaacagagtgaaagttgctcctggccagaactttatttctgcatttt
aatggacaaacataaaaaacttcccatctgatggcttcttgagcctagtg
catgggtgacttgaaatatgctagcaccacacagtaatttttctttgat
ctttttctgttttctccttttgttttctagttgtaagtgccagaagctgact
gtgagcttataggaaaaggagaatttcatggaagcacactgaaagcatgg
gttctttccttttgggttctcacttggtggggtctccttgcagctttg
gaggtgggcaattaacatccccccagtcatgaagtgtaccagaaactgt
ggttgttttcaaatgagagttcaatcacttctacttcctgaggatttat
agatgaagttggagataacaccattgatacattaggatacatcatttgca
ttttaccagctattattagttttaacatgatggcatatttagaactagag
ttatccatgatagaaatgaagttgttccataaaaaaaatgggaatacattt
gtttgaatggctagttgctcaattactgttatagtctttaccatgggcag
tcacaaactgttgcaatttattttatggtcctgtcgaaacttcttgtctaag
atctgatcttattttacgttgtaggtattccattacttgatcaataatgt
ttagaattgtatatatttgtttttgtagaccaattcattagttgtaatt
gagttagaaaacatttagagatatagaaacacatttattgttgagattgt
agtaaaaatttttattgttatgcatttgaaacttcttggcccctagcc
ccctttcctctgggaaattgtttttataatacccaatttgataataatga
atgtcttaggaatgtaattataacagtatagtaggagactatattgt
ttttaattaaacaagaacaggtgaaaataagaatagatcatgaccaaatg
aaaaatgtactagagagatgtaacttctgttttgcagaaatagaaatca
aagatatagaggaaaaacttcataacttcataaacatccaaggaaattaa |

Illustrative Sequences-All sequences are shown 5' to 3' taagagtttaaatggataagaggtaattagatgacaaattatggagctcta
atttagaatgtaagctacttaatgtgcaataaacatcttgttgttacccaa
cccctaagacatagcttaacatatagcatagcttaacatatagtatatac
tattattgttaaataaacattattttcttgaatttataaataaaataatg
agtgttttaaaaatagagcagatggatcagaagtaaaaacttgttataat
gttataataaaataaaactttccatatgtaacaactacactgacattgta
ggatttcttttgagcaaaattaaggaatgcaaggcataagtaaataaatt
tttaaatttctgggacgaagaaatttcttaaagtacatgtgaaggaaaa
acatacacgcttttgtagattgccttcatctttcttatatagaacaagaa
cttttaaagaacacaggtaaatgtccacataattttaagagaaacaagt
ttgaagtatactagaaactctggttgtttccgtatgagagttcaatcact
tctacttcctgatattttacaaatgcaattggagataacaccaatgatgc
actaagctacaacatttgcattgtaccagctagtattagttttaacacga
tggtatatttggaactacagctatttatgtagaaatggtgttgttctata
aaacgttttatgcctacccaattatcagcttatacataaaagcaacagaa
taacaaaatcttccaggtatcagagaacataacaaccgaatgtcttttcc
ttaaaaattgcaggaaatattgtccagatcactgagaggtgaggtagtat
aaaaactcaagaataagaaattccaataaaaagattaatactaagcatt
gaaggcaaagacaaaataagtgaaaatagtgaaatcaaagtgaatttggg
aattgatgctgatagctagatatttttttactaagggagcaatgttttcaa
taaaataatcctggagggttttacatttttaaatttaaagcatctataccta
gtgatcacaatgtgaaagaggacaggaaggaaataaaagcattataaga
agcagcattttttgcttttcttcaagtcattaaataagaatgcatataaa
agtatagttgtagacaattttaatgtcggcactagtagaattgaaagcagg
atatctattttctaaataattatcaaagataaaaaagcaaacatagtcca
ttcaaaagacaaatgaaaggcaacaacaaggaattattgaagagaagaa
agtttaagtccaatcaagctttaaaaatataaaataaaaaatcaaagtc
aattttcctattcaaatggaaagatcctatattaaattaaaatcaaagtc
taatggtttggtggtgcttaaaaaagtcatacgtaaaggaaaagaacaca
gaattattttttaatggcaaagtttttttccagcctaacatgttcacatcc
aaatcaaaaatacaatatgaatatcaaacagggcagaattttttggcagaa
aaactccaaacagtaatcatgacaaaagggactattttatacttgttaa
taatgtcgttctactgaaggaataatagtactgaaagagtatgcattaaa
taactacaaataaaaaataatttatacattctgttttaaaaatacagtat
tacttaccacagcaaataatatatatacaagcagtacaaaagtttacaa
atttaggagctatacaagtgaaatactttgtatcagtaggttaaataaga
aataaattattaatttaatacattttttgaaagcagaagagaaaatttac
tatctgttcctgaaaaatgttgaaatagaataaaataatttttatcttaa
ttattaatatcaaaattaattaagaattctaaaaatgtacatatttaaaa
caggatgggatgaaagttgctataatggtttttgccataataatatcattt
aatagtatttttaaaactctgatcaatgtaataaaaacataccaaggaaag
aaaagctatatagaatgaaaaaagagatacaacattatgtattgaaaaaa
tattttttatagtttaaaaaacccaaagtagtcaatgaaaaacctaaataaaa
ataattggtgaagataattaaaacatataaaactaacataactcagcagta
taaatgtaagcaatcattaactcaaacataaactttttaaaagagaaact
ataaaaaacaaattcacagactggtttcaagtgtgaacgataacatttttt
atattgttatttcccaagtttaatggaaatgtaataacaatctcccttttc
atttttttactttttgaggtagtggtgagaggaattttgattttagtgtaaa
tctagaagaaaaagtagtcaagaatagcaaagttcaattttttagaaagaa
ggagtgactagtcttatcaaatatttaaatatataataaaagttataataa
ttaaaactatactggcaccaaaataaatatattaatgaggcaaaacatgt
gggcaaataattatataaaaatatatttgataatggctggacca
cagattaaaggagagggaaatgttttgcaatatatgggctaatggaaaa
aaaaaatcagcttttacactcattatgtacataaaatacattatgcaaac
taaaacctaggaagtctaacgagactttatttataggcttaaaacatt
gtaacaaaattgcaaagtgaacagtaaaatagatttgattatattaaaca
cttgattagttaaacaacaatgtaacaagcaaagggtggctatgtgca
attgcaattatttgaacataataacaaagagttgatatgatttcacaaga
gctcatacaaactcatacttaatcaatatatgagataagaatgaaatcac
atttcataaaatatgaaatataacacatttgcaagcacataaaaatccag
ccttaataacaatgaataatactacaaagcataaactttaaaagagttta
tgtttaggtttaatcaactatttaaaattgatgtcaaggacttacacttt
cagctgttacattagatcagctcatcctataaggacaagtagaacaaat
agaaaagttgaataaatctaccaaacgtttgtttaaaagcactggagag
ctccacagtggagagagcttgagcagcagaaatttaaagaaagatcctaac
tgcctgtcagaaactaaagtaaaacatcacttaaagaagagatgatcttc
cagaggtctaaattatctctacaattttttcatacacaatgtctggcattc
aataaaaattaccaggcataccagaagacaagataaaatgactgaaaacag
agctagaggagatccagatataggagtaacaaattttaaaatatctatgc
tatctttttaaaaattatatgagtagatagaaaatttcaacagactactat
taactgtgataaagtaacaaatggaaattccagaactgaaaaatttaactg
aaattaaaaactcaatagttggatataagagcagattagaaattcttgaa
gaacaaacttatgagcaatagaaattttgatgttaatacctaacaaagtc
agaaaaggtgtattggaaaatggtttctctcatgtaactggtgacatgta
aacctatataccactttttggaaatactttgataatgtgaattcactatt
tgaacaaaaaaaatttatatcttttaacccagtaatcttatctctgggaat
gtgccataggaaataagttttttaaatccacagtgcctcatgtatgaagat
attcactacagacttatgatagtaataactatctacagacaatgtttaaa
tactttatttcaattaatgcaggttaatcctcacaacaatctatggtgct
agtgaacattactatcctcattgtacagatgagaaaactgaaacattgag
aagtcaagtaacttgctcaagattatatagctagtgcatagaggggcaaa
gatttgaaccagattgcctggttccacatgcactttaacctgctttattt
aggcttttgaaagcaacctaaatagctaacattgactaaataagtgcagt
atacctggtctgtgtgacattttgcaggtattaaaaagtgaacattctga
acccttttagcaatatggcaaatacttctgatgtgatgtatgcatataaa
tatgatcgaaagcaaatatcccaaaaggttgatggcagttatgtcaggtt
agtagcacaatagtttctttttctcacatttttagtaatgtgt
gttgccatattaaaaaacaaatattaaaaagtagtagcatgtattagat
cagagcatgggctcagactgcctgtgtcatctcttattagatgtatgacc
agggacaagttattgacctttttgtttctaagtctctaagtttatcctgta
aaatgaagataattgtagtaacttacctaataacatgattgtaaggattaa
attatttagaacactatttgttacttggaaaatatgcaatcataagctat
tttgttgttattgttattttactaccaaagcttattgtttcagAGCCCCT
AGGTGACCAGGCAAAATGGCAGTTCCTTCCAGCTGGTCCTCAGATGGGCA
CATCTATTAgtaagtttcatttctgtatttggatcttattcatcctttat
tatgaattcccaatactgaggtttctaggaacctacctgccattggctg
aagggttgcttctgaattcttcccagaggcagtgacaaaaatcaaacat
ccgatgtgttctttacctttcagtaagctcagcctcctgcttgtgtcac
atctctaaacatcagtacatgcgtgattgaaactgtctattgaaagcaat
attacattaacattatcaatactgaattagagaaaaaatctatcaatgtc
accaattccacctgtctcttgatgtatgacttttttacctgacaggctaaa
taacaatagaaagttctttttaaaaaatagaagagttgctatgcagggac
ttttttggaattaagtgcccagagaacctagaaatgtgcttttaaaactt
tttgttttcacctggcagatccaaaaaaatttggaagctttggtgaat
tccctcattacttgaagttgttttatgaaaattgaatatatatatctgtt
aggttaccaagacttatggttagctatcttaatggctagtgatataagac
cttgtaacaaacctaccaatggaactgacaggattttaccagggaggat
attgcagtacctgtaagaggaagggataacaaattggcacttcatcattt
gtgagaacaattgcctttaatgtgtctatttggttttcataatattgcag
GCCTCTGCTCTTGTAAGAAGTTAGCTGCAGAACCCACATGTGAATCCTTG
TAGgtgagtccaccatttcactaatactgtgttttaattgcctcagttac
gtccatctgacattcattggcaaagtccttttggttaaacttcctaataat
tctcagctctatcatatgtaaatgtttaacacattgctttaatgtttga
gtttttcattttgttgaagttattattcctctcaggttattcatgaag
gcatttctggatttatgcctccctgacccattccaggatttaccccaaa
ccttccacactctcttctaacaggaaagttctgttatgacacaataagtac
ttattaagacagattttaccttctcaagtctcaggacagcatttcacaacca
gaaataaccggtcacatgaagaaccagagtctggtagtagtgaaattcat
tttccttcttgaaaaagtggatcaaaggattcaaacagcaagtggtgaat
caatgaaaagtggtaaaatggtgaggaaaaaatgttactaaaagatgacc
tcaagattactggtgcatatgaattgcttttttatataggaaaatactgg
ataatttcttattgtcatagtataattagaagcaatttcatgtgttcatt
ttgccacatgagtttaaatggaatagatttggttccctctctaacatgag
ttcagtgctcgaacttggcaaacatttctaaacaattctgagcttcctac
ctctgcttgaaagtgagaacaattgtatttatctattatttgtctattag
gttatgagagcaaaatgtcataacataaaacacctggcacccagcaagc
aattaatgctagtccttcccacccctatttatggaggtagaaagaaaaaa
gataacagcagctctactttttattttttacatatatccttcattgattac
cttatgagtaaacctaaaaacagcaaaattctcatctcttcatcctcat
ttctcagtgctttatcaaatttctactatgaactaagaactgagtgctat
gggagacacaaaggagagtcaggtattgttctgttctcaaggacattggc
atctagaaagggagattttttttaatgccattagagagacaaaataaag
cactgtcctgttttaagcaggaaaaatcattttaactggggttaccaag
gaagtttcatggaataggtagtgtttgggctttaaagaatgggtatagt
ttggaaagcaagaagagaggaaatacaatgagtcatgactgaagcacagt
tgacccttgaacaacacaagtctgaactgtatgggtccacttatagtgga
ttcttgtcatccaaaagtggatcaaaaatggtatttgctggagtgcaaa
acccatgtatagggaggactgacttttcttctatgcggattcagcagggt
ccacttgagtataccaggattttggtattctgtggggtgtcctggaacca
atccctgcgcatgccgaggggagggacaactgtagtataattgagagaa
aaaccattgtcccaggattggaaggacaggttggcattaccttggtgaa
ccacttcttccctgtagccttcaacttcttcacttgtgagagatgtagaa
taatccctgccctgttggtctttcagGACTCTGGAGAAGATCAAATGGGA
GCTTAGATGTGGAAGCTCTTTGGAAACCAAGAAACACTCTGAAAATGAAA
AGGtatcttttttccttttctccctttaccataaatttcatgatggca
cttaacagagccagtcgttttggtatttaaaaaatgtttggtgaaataat
tagttattggttgaatgaataatgaatttataagtgaatacatgaatttaaaca
aaggtatggagtaggaaagcacataatatgagcagagaataagggattct
atttggaagcatgcactagaactggatgttagggatgtgaatgtggctag
ctggaatgggtctgtggttctcacaatggatctgttgaccagcagtgtc
aataccacctgttaacttgttagaaatgcaaaaagaattatgaatttgaa
actcagggtgggacccagcaatctgtttctctctaagtcattctgatgca Illustrative Sequences-All sequences are shown 5' to 3'

```
tagcaaagttttgagaaccatgactttgtattaaggtggggagtttggaa
attattttctgtaagttcggtgctaatgaagattttcaactgtgggtgg
acataatcacagccgtatttctaggatgatgaggcagaaggttgtaccta
caatatctatgacttcagcattaaaaggacaattagaagtactggaaaac
acaccgtatttgccaagctccagaaatgaagattttgttttttacctattt
ccgaataatatcccatacttacctaagaggcaaagcagagcaagcattg
ctcccaggcactggggaaacccacttggtctgcagagcccaggcaggatg
agaatgtttatgtgaaaaaagtaaatgagagcggactgtcaaatacggcc
ccaacctttctgcagagagaggagtaagtaagcctttagtcctgaccaac
tgtggggaaacattaaatggaaccttccaaattggtttaaagtgggcagc
taagcctatgccaaggactaagccaactgcactggctacaaacacactg
tgtcttagggctggtggatacaaatttgccaaaggagagcacactacat
ggaggaaaaatgaagagccgcagggaaacatttatcctaaaggggaaaga
gtcaagacagagatatcatgggtcagttgggaaggagatggagggagag
gcaggaggtgagctgttcagattgctagaatgaccaatccagatggctag
gatgaccagtcatcctggtttgcccaagagtgagggatagcccacatcat
aggatttccaggacaatccttgtcaaagcgggacaattagtcaccttaag
actctgcccttttcacctgtgttcaagacctggggagaaggcataataaaa
atagaaaaaatcactgctgtcaacctccgcttctcaaaatattgtccaga
aactagcagcataggctcacctgggacgttgttagaaatgcagatactc
aggcatcctagacctactgaatcagaatctgcatattaacaagagctctg
agtgatttgtatgcacattagagtttgtctcaaaagatcttgtggcatcc
cacagtaaataatggagcacaagtggcagaaataatttcctctgggctgt
aatatggctaatatccaggttgatcagatactaagctaaaaccagatcaa
ccttgcctgggaaggacgcaacctagggatggagagcaacccaggcgag
agggagaaagaggctgacacaaaattagccaagaggggacccctgaacta
ttaatagtagtagtattttgtagggaaagtgagaaaagccagcaagccagc
aattgtatggtaagaataaagctagagaaattaatgttgccagtactgtg
acccttatttttaccacttctaggctgatgtgggctgggaaatgggttatg
cttagaaatgtggagcctgccaagtgtggtggctcacacctgtaatccta
gtactttgggaggccgaggagggcagataacctgaggtcaggagttcaag
accagcctgaccaacagggagaaacctgtctctactaaaaatacaaaat
tagtctggtggtggatgcctgtaatcccagctgctcgggaggctgaggca
ggagaatcgcttgaacccaggaggcggaggttgtggtgagccgagatcac
accattgcactccagcctgggcaacaagagtgaaactccatctcaaaaaa
aaaaaaaaaaaaaaggaagagaaaaatgtgagccacaagtggtaagc
ttgtagcggtaagcttgtagagaaaaatccaaaatgatcatccactaaaa
gtgttcaactccagatcttggcctcatccacttgcatatcattcaaatac
agtgtgcaaagaatagttttctttctttttttctacctggtctgatcttca
tgggcttcagctctgcagtctagcagggataattgacacttaattaatag
tgtttcattctcctctagcttgaacatatttctttctctttcaacattga
agccagtagttctaaaaatcaaacatgcaaacatgcatcagtcacctgga
gggcttgttaaaacacaggttactgggtctgccctcaaggtttctgattc
agcacatctgaggtggaccctagaatttgcattctgagttcccaggtg
atgccgacattttggtccacaggccacacttaagaacctctgattcaaa
ctattcagagttttatttcatatccaaaagtgattatttaaaaagtatctt
agattaatgctcctcaaactgattgattttttccaatcatgtaccaaatac
atagtcctatttcacatgaccagtattcagctttgctgcaagcaactca
ccatgccagttccacacacctgaacaggttatatcctgtttaacaagatc
agcccactgatcacatactaggatgtcatgcaatgtcaatttatgatag
aagtttctaaacatgaactttcatctgtatttatctcaccccgaacagg
aacagttttggacttttgcgctggccctcacccactcggatgcatt
gttatagatgacacggtctcttataggaaaatgcacagtctttcttagat
tctctacctccctcttccatctcattcccaacatagatctgggtacatga
gtggggtcttattataatcttgtgacacccttggatcatgcactaccctc
taaataatcaaatagttctactatagagaggctcaatttatcttctcct
ggaattgggaccactgaaatataactagaacccaactgatcttttgagat
gttgtgtgcttgcccttactgctactgccgtagttctgaacattttcccca
agcatcaaaaggcccatggcctcttttcctagacctctgccagtcc
accaacactctcagtggggaagtaagaagcctggtggatcctgcttccca
cacaaaggccatgatgagacagatgcttctaagtccgatatatctaccc
actttctgctgtcacctctgtacctcctgagtcacatggaatgtggtgct
gagccaaatggtcagtcttctagaagcagtggaatgttggaggcagctta
taccttagctgattcttaaattttcaggaattttgtgagccagttttaa
acacagccattgttgaaaattaaacaatataaacttataatcaaatatat
taaaaataaagataatgccctcaactcatccattcctattattgttttta
cactttagtactatctatgcttattgtatgtgtatggtggaaatactaca
taatgatatttaatggtgtactgccacacagctcttcacaactctgcatt
cagtgacatcactttggtagcttgaaatcagccatgataggagtatttat
atcttggaaattggcaaatattacaaatcagcattccaccctcccttacc
tccccaccccccagccagttgttaaacatttaccagcatgcaaccaccca
gagcctgcatctgggaaagtgagccactaaccaatgacctgtgataacc
ctatacatatcagctgttactaagctgcccttcccataacggtctgccc
caaaaggtgtgtgtgcagaggagaataaaaactaaaaccctaagatcat
cttatttacttgccctatttctgcctcttttctctccctgccatctctgg
ggtccagaagtagaagcttttttattgcctccggagtttattcttatacat
```

```
caaggataaacattcatgacctaacatcatctctcttgttttctcccgcc
aaagctataaggatagtctaatcatgaaaaaacattaaacaaactcaaaa
tggggacagtctataaaatacctaaccagttctcttcagaacagttaagg
tcctgaaaggcgaggagagaagaagaaacaatcacaacttggaggacatt
aatgcactaaatttaatatggtttcataagttgggctgaaaagaaaagga
cagtagaaaagctgggatatgagaatacagtctaagtgtagtactaatgt
taagttttttaatctctaactttgatggcatggtttatagaaaatagaaacat
taggcaaagctgggtgaaaggtatacaggaactctactatctataccaact
tttctgtaaacataaaattatttcaaaataaaactaatataagaaaaaa
catggccgacataacagatagaatggatatcttctctagtctatgaaaa
ccctgtgtcctacattcacttgctttgtgatataataaaaagggggaaagg
aaggggatgatagaaacattattcctcttaataaaacttggatttttaaaatc
ttttatcttttcacagcataaaacattccacttaggatgctatatgttga
gcattaactttctcttttttctttatagtctttctgtaatagttcaaatcc
tgcccaccctgagggtggatgtttctcagatgatgaaggaggtcataaaca
gagagtagattaatataattatctttatttcatgtctatttgcaaatggg
ccattgttcacatagttgtctctctcttctaaatggaagaatagttggagt
tgggggtggggaaataccagaactgagaggagtaaaggtgcttcaagaca
atgcttcttaaacttttggttttgttgcatctcttgggggatcttgttt
aaagtaggttggagtttcagtatgtttggggagggcccgttaatctgatt
ttataaaaagttcctagatgatgccatgctgctggtctctgagaagcaag
agtctggggtcctttctaaagtgtttcctctctcctctatacagtcagaa
aaggaaagctgcttactggtcagagatttaaaagacataggagatatacca
cacttctataagcacagaaacaaaaacaaagaaagaagaaacataataac
caaaatatgacattattgcacacaatgagatgcagtaaaagatggactac
ttaggcattcactggacataagtgaagctgcctttggagtttaattttaa
gttctcagtaactcactgtatttagtcatatcgtttcacatacagacaaa
attccttctctactaagaaggaactaaagctctcagaattactgagttgc
acagtaccaatttacatgaatatttttcttcctctaaaagtttgtaatga
ctatggttcctggaaaataatatttcatttttcaattcatactcttaat
ctaccaaaaaaacactcttccaaaaatataagctagaaaaaacaggtaatt
tgctcatatcatagagacaactcataccaataaaaaaatacattttaaaa
tttggaaaattacaatgagagaataaagcattttgcatgcagatgtgtta
tgttttttactccacaatattgggagcttccaaagtgtaacatgcatttac
agagccactctcttagcatttaaactgggaggcattttttcgagaagcatg
agtcttgctcagcggtcctgtagccactctagcaatctcacacagtacat
gacttataaatattgtatgtgcttgatggaagtagacctggctttgctaa
tcacttaccagttcttttgccagtatttctttgttttagaagtaacttt
gtttagcttaccaaatgtatattgtccaatttgtaggaaatataagtaat
attgcaacagcaaaatgggattgtatgtgcagatctctgcatcctgtg
ggccctgtcatgttagtaatagcttttccttgtgctgttgccactgccaa
acagactgcttatgcgatctttggctttcttaactcctctttggggatca
ataaagtgtttctttttttttcttagataccaacttcatctctctcttaaga
atacaatattagtttaaaagattgttcaactaaaagcaatcttgtagaga
ttgtcacccatgattgatgctgggtgagtagaaaggaaaatgttgatttt
atcctctgcctttcagatctttgaagggggaaagtgggctagttttttaaa
ctgcagcctgatcaaatgtttcaaaagttgttcaaaagtaatcttagtcc
aacactgctcctctgacttttatctagagaaaatagaaaagtttataatt
aacgatttgtttctttttaagtacttgtgtacatttttctcttgcaataag
tattaataattgaaaattattaaattgtcattttaatgtttttttattaag
taagtttgatatgtttcttagcaacgaagacctgtggctcaaataggagc
agacaattcatgaaatcaaattttaaattcaagcagagctatcatactga
catatttgtatttcccttttgtcttggaatttattgggttgtttaaaataat
aagtttagccaattattttgttattctgttattaaatataaatttgca
gtctaaaatttttttgtgtaaaggtgagtgtataaatgaataaaatataa
ataaataactaatgatcacatttctactgggaaacatcattatttcttac
tttaaatgtgtcaattatctttccatgatgtgttttgtgcacatgcaagtg
ttggctaagcctgattctcttttataaaaaaatggtaaatctcaaataa
aagtgcaaaatattatctttcatgcaaatacactaataataccaaagaaa
gcagaaaaacttacttaaaaataatttttcttgacaagagattttataaat
agcagcttgactaatcaatttcattactgttccttagctgcagccatgtt
ctcttggactatattgctcaatgatcttgtgctttcttttgctactcatac
taaataatttgtgttgttttgcatttttttatatcaggagcaaaatactt
aaaaatttataaaagttgaagggaaaaagggcactcccatagtagataaa
agaaaatgtagcattacttcatcatctttatggagactcttcagaaagat
gcatgttttttagaaatatgaaatgatatagtatctgaaagttgcttt
aactactaatgattgggatggtaaattggcacaaccttttctgatgggcag
gtgggcactggtcattaaaaaacaaaacaagaaaacccttaagctgtata
aagctattcatacagagagatttactttttataaatttacgctaatgaaat
aatatggttgtgttcccaattagcataagaatgtttatcacagcatgg
catatattgaagtttagtaaatgaagatacatccaatctgacatctctat
tcacaaccacaaagagataatgtagaaacatatttagtaatgtgagaaaa
tactaaatattaagtgaaaaaggtaagttacaaataatttgcataaaat
catctcatacaccacccccccatatatatacttatagtatgttatataat
gaaatgttaacagtctctggtttgggtgttggattatgaaatacatttt
tttctcatatgtatattcttgacccttcaactaacaagcattatgttttt
```

| Illustrative Sequences-All sequences are shown 5' to 3' |
|---|
| aataaggaaaataatcattcacctttaaaaaatgaattccattaatatgc
ttccatttgtcctttgaaaatttaatacttttatatattagttattccat
aataagtagttgattttgaaaatagaaaattaggtagttgttctaaaaca
aggcaagaaagggttgtgtaaaataccataatgacttatttttattaatag
ataagccataaatatcctgatgaattattttctgatgagaaataagaatt
gctgtggctcagagttacatttttcttgtaatgtgaccaaggccaaaagga
atttgatagctattccaactttgtatcgtaaggagtagttttttaacattc
ctgaatagataagatagctcctggaatcttcccaattttcaactatttct
ttgatgactatctatagtgattgatttgttgatataaatgttaagctgac
atatatttactaaacgtctattattagttagatattactaactgctatgc
ataccagagagcatgaagtataggctctcacctaaaggaactacagtatt
gttgggtaataaattgtatgaaacagaacattttttagagaatataatgca
agtactaaaatgactgaagagataagaaccatgatatttataaagcagtg
gataaatgtaggctgagagtttgggaaaaacttcaagaaaagttgtgact
tgcctggcttttgaaaagataagtgatacttggtttatgagagaggagggaa
aagcatttcagcttgtgagatgaaggtctaaagtccttagggctgaattt
gctggttgtggctatgtttactgcagttccagcagagttagagatgggt
taggccaggacagtaaggatatctgcctgaagattcctgttttccctt
agagggaatagatttaaggtggcagggatcaggtaggaaatgatggggac
cctgaagttagagctgagaatgtcttctcagcttctctgataccatgctc
taagtttgctcccatttctttcgtggttccttctcttttcatttgttggc
tcccaacctcttctctactcagtctctgaatgttggactcaactgaagtt
cctagctgctcttctgcctctgttctcattccctgaatgaaagagaagg
gttcaaactatccaccactatggtttaatacaattacagagctccttga
aaagtgatttgtctagggctggggagggataaaagaagatgagcctggag
gatgtcatggtaccaaaagtaagtactcaagaaaagcgggggggcacat
tgaagacacaggagccaacctaaaagagctaccaatggccaaagctag
accaatttcagacaaaataaaatattgaattatgaagcagaataaaataa
acacaatttagtccatactgatataaatataatgattgaataaaagtaaat
ggtagagaaaggacaacttcttacagaataattccaaataatagatgcaa
aaggaaaggaggaaataagaaaatcgttgtgagaacactagaagactgtg
aaacgttgctgcagggagggatctgcctatgcatgcataaattaatggaca
atgttttgagagaaaatggctatttggggccaggtgcggtggcttacacc
tgtaatcctagcactttgggaggctgaggcgggcggatcaccaggtcagg
agttcaagaccagcttggccaacatggtgaaacccgtctctactccaaa
tacaaaaaattagctgggcgtggtggcaggtgcctgtaatcccagctact
caggaggctgaggtgggagaattgcttgaacccaggaggcaggagcgca
gtgagccaagattgtgccactgcactccagcctgggcaacggagcaagac
tctgtctcaaaaacaacaacaacaacagcaacaaaaaacacaaaaacaa
acaaaaaaccttttacaataattaaaaagcatgtaaacaccacattagcc
aaatgatcaaggtcaacatcaccagtaataagacatactgcaacaggta
ctgtgaatatgatgcactgagaagagcacctcacctctgtggtatcttc
ctgtgaatacatagcctcaatttgatcatgagaaagcattaggagatata
tctaatgttaaatggcaggttagtgcagcacaccaacatggcacat
gtacacatatgtaactaacctgcacattgtgcacatgtaccctaaaactt
aaaagtatagaaaaaaaaagaattactcagactaggagacccaatatttg
aaatacaaagtaaacctctaaaaataaataaataaataaatagctattac
tgcaaaaaaaaaaaaatgcaaattgaggagtatttttacaaataacctgac
agatatttctcaagagtgtcatgaaagacaatgataaacgaggaattgtc
tcagattggaggagactaaggtgatgaagaattaaatacaatgtggaatt
ctggattggacccaggaacagaaaaaggcattagtggaaaactggcaaa
atctgaataaagtctgtaattcaggtaatgatattgtaccaatgttaatt
tcttacttttgatcattgtaccccggtcatgtaagatgctaacattagaa
gaacctgagtgatgggtatatgggagctcagtgctatctttacaaatctg
taaatgtacaattatttcaaaataaaaaagttaaacatacaaaacatctac
ctacagagacctctcagtcctctgtttctctgataggatcttattttttct
gccttttaaaatctttgccttcttcctgtccacatttaaaatcttcacc
cccttttgtcctcacatgtgttatcttgtcacctttgaaaacaaaagccac
tgggtcttctggataatttctcagatggaagtgaatggcaagtctccttt
tgccctccaagtacagaaatcctagatataaatattgttttttaaaatgtat
aggtaaactcaaacagggaaaattccccaggtgccagcacagaaagcgatg
gtctgtagacattagaaaccctggacctgagggcaggactgaagttgtaa
tgccattgctgggacaggaaagaaagcttcaggcatggataaggtaagga
gctagaactggaccctgcatcctcaaaaacacagggtgtaggaaagaccg
atcattggccggggaggtgtcaaagatgtgcgccttatgctagggggcac
aattgggaaaataactcatcataaattatcaaactcaaacctgcactctt
tgtagttgtgggatccaaattcactatctctatatgcacagaagctaat
aaatgaacgtagaaatggttatgaaatgggtaacacttctatgggcttgg
cagggacaaatgcaaaccactttgcagggatgttttcataagcctgagc
aagagagtctctcaggtaaaaagctactgaatgtcagtttactatcaaaa
attataaagcaaagaaacaaatcctcatcagcaatgaaccagaaaatta
acactctaaaaactaaagataatttaaaaaatctaaatatagtttgaaa
taagtatgtttaatttgttaagaaaaaaatgactatgaaactagaaaat
gaagattttggaaaacatggaattttagaaaataatccgtgtaagccgttg
atattaaaacctcaatggaagtgttacacacgagattagacacaatgaag
agcaagaattagatactagaaaacagatctgaggaaatcatccagaataa | agatcaaagaagtacagagaagaaaattttggaagaaaatttgattcatg
aagggtagaaggtgaaggttcaatatttttctaaaagcaattctacaaga
atagaagagagatggagaagcaatatttcactttttatctactttatggtc
acacacatatatgtatgtgtgtgtatatacgcacactatatttgtgtg
tgtatatatatatacatatatatacacctatatatacaggtatatatata
cacatatatatacctatttatatataccctatatataccctatatatacacc
tatatataccctatatatacacctatatataccctatatatctctataata
cacctatatatacacctatatatgcctatatacacacctatatatatcctta
tatatacacctatatatacacctatatataccctatatataccctatataca
cacatatatatatatacctatatatacacctatatataccctatatataca
tacctatatatatacacatatatacctatatatatacacctatatatatata
tatataggtttcaccacatccccttagtaaatttccatatggtctagca
aatcctttatcacatggcatcactcttatgtggtaactcaactgaaacta
acaacttaatatttcgataggactattacaaaaaaattgtgctggaaata
aaatgaaatagacttggctaacatggaccttttataattggagctcaaca
atgaaaaaaatagataattagtaggaaaagtaaaagtttagttttagggt
tctgtaatatatagggtcgtgtgtgtgtatatatatatatatacacac
acacacacacaaatatagtgtgcgtatatacacacacagatacccaat
agctggtggataataaggactgtctgctgtactcagcataatctcactat
ttattaaataccacactcaactcatcatgctattgctgactggaaacatc
cctttttcctttcatccaaatttattttactatcttccagatccaatctaa
gttttgacttttctatgaagggatctcaatgatgcatctcttttccttac
acttctgttttgttgcatctgaaccactcagtactaaattgtgttctat
ctacaccaagcttgtccaaccgacggccctgtggctgcatgttgcccagg
acagctttaaatgcagctcaatacaaatttggaaagtttcttaaaacatt
atgagttttttttagcgatttttttttaagctcatcagctgtcggtagtgt
tagtgtattttatgtgtggccaaggcaattctttttccagtgtggccca
gggaagccaaaagattggacgcccctattctacaccaagagttaggaaac
tatgaaagccaagcaaatcctgtccactgactgtttttgtatggtccaga
agctaagaatgatgtttacattttaagtggttgaaaaaaaagagaag
aagatgtttcatggcatattagaaattatatgaaattcaaattttggtg
tcctctcagtgtccaataaagttttattgaaacacagtcatgtccacttac
gtatgtattgtctatagctgcttccacgctgtaacagagttcagtagctc
caatagaaaatctgtggtgcacaatggctaaaatatgcactttctggcca
tttccagttgaagtttaccagtctttgttctacactgcaattttgtcatg
tcaagtacaggattttaagaaatgaatctcacttcatagtgcaggaggta
gcagtgtcccctctccctgttgggaacttggactcaagagcagttcttttc
aaagtggtcctcctcagaaattcctctttcatctctcaaacctgacactt
ttatatccttgaggtgggtgagggcttccaggaaatttgtaactaggttt
cagcacatcccctttagtaaattttccatatggtctagcacctctcttttt
acatggcatcacgcttatgtggtaactcaactgagaataacaacttaata
ttttgatagggctattacaaaaaaattgtgctggaaataaaatgaaatag
acgtggctaacatggaccttttacaattggagctcaacaatgaaaaaat
agataattaggaaaagtttagttgtagggttctgtaataatttt
ttaaataagataagcaggtctttacacatttgaaaagatcctgggtgaaa
ctacggagcaaaaatagcgttttactgtggtatcattttttcttttcttgg
cttcagctgtgtgtttttagtgaaataaaatgaaaatagtattgaatgtcttggga
gatttgtcattttctttgataactgctaagacaccagagggtttcaattgt
ttttgatcctctttgatcttcctcagctactctttttttcagcattgtagt
attttttgaaattttttacatgagaatgaacaataaaagttaacactgtcat
aattaatttgaagagtatggctgtgtttacacaataaaaccatttgcaac
catcatcttcatcttttttctcagtagattaattttcatttgcatatata
cagcataactgcagcaataacaagcaaatatcttttttgtctttccaaaag
aatactttttaaaaattagaccatttcatagtcttgaagtttagtgcta
aagcatttcaaacagcattcgtatctgaaaacctaccactgtcttttaca
ggaataacagaatgtttaataaccaaactttagccataccaaactttgaa
tttccccagatgcctaagatggcaatatttcatgggtccttttctagtagc
tctgtttagaaaacaaaacagctaggcttttgtttagatggataattcaac
aaggatttccactaataatcatgtccagttcgttcagggggagcacactc
aagtttgatgctgcatcaaccgagtataaaccaggactgttttctgcaat
tttagctttcagtctgtattagctgtgttttaaaaagaacaagaaaaga
gaaaaaggaaaaattgtaattgtaataggcttcctttttgtgatctcttagg
gagaggtcttttttaaataaggggcttgaacttgaccttcttcaatggcac
aaaggtccaatgcgcagttttaaagctatatttaaattttaataattat
actcattggaggctagaatgagacttctcagaacttaatcctcaatcttttt
agtgaaactgcttggcaaagaacagaagctcaggaaaacgtctgcagtag
gtacacaaatattttccctgattcttcatcccacagaatcaaactgactg
ctttgaggtcatcagtatagtatttgagtttgcaaatgtaatttaatata
gagttataatttaaaaaatgcttatcttcaagataaatctagttttagcg
acctgatactgaaactagattttcaacattttaaagaaatcacactctca
gtgttggcaaaatgcatggaagagccactgtttgtatgctgtttgttgaa
agcataattttttaaaatctttctggaaggcagttttgcccatatctgttg
aatgcctccaaattttgcataaaacctttaaaccagcatttttacttttag
gagattcatgctaagaaaatagtcgtagatgtttgcaaaattatagctac
aagattttttatgtaagtgtttttggtagaaacaagaactggataaagcat
aaatatttaacaaccaggctctattcagccattaaaaatgatactagaga |

| Illustrative Sequences-All sequences are shown 5' to 3' |
|---|
| aatatttaatgccatggaaatggttaaaaaagctgattaaaaacagtatg
cacaatgtgattccctttttgtaagaaaaaaaatttgcatcaaaaatactg
gataaaaacaaatagaatgttaacagtagaatctgtatataaaggaattg
tgaataccatttttccaacatgaaaatagcttcttaaaatattcttaaaa
ttaaaatgcatagtaggtgtaaaaatctcaaactataggaaagtaaaaat
tgtaagccttttccttttaattgcataatttggtaggggacacacacac
acacgcacacacacacacacacacacacacatacatgctacctctgttt
tggttttttattcaacagtttatcttggagaattttacgtgttagtgcat
gtagatctacttcattctttaaatttctatgtggtattccataatatgat
tgtgtaatacccttcttatcaactactctgattattcttatcaactact
taccacacttatcagctactctcaccattctgttccaacagcaggattta
tagatttgaccttttcttcatttcctctctgcttttcacttctctcctt
ttccagcttatatagttattatttcatttgacgctctcttttttgcccc
atctgcaaaaccacaactctcaattccctgtgtaaccaagcagacaagca
ctgttgaagaaaatcctgccataggggcagttatgtcccaccttttaagac
actcaatactacccggcaatcctgctagtttctctggtgaggtcaccctc
tcactgtctgccactattatttcaaacggtctccattcccctcaaaagtc
agatttcctggatctcctccaactttccctctcagagactgatgatgtc
tcataatatagaaaaaattgaagccttgacttccatgtaccaattttataa
accttctcaattgtgtatctttctctctcttccttctttttacatggaa
gaaatgtatttgcttgctgttgtttcatttaggaattttgtacatattt
ttatgtaatattattttaacagttttcctatgtagactgcttttcttagt
tttgatatcagggtttattctgcttgacttgtagaatgacttgggaaact
ttcttttgtttctttgcttttcctttactcggtgctctaagaaatttg
ttccttgaaagtttggtagcagcattttggtacaagtctttgagtagtgg
taagggtgatattagtgtatgtgtgtgtgtgcctgtgtgtatgccaatct
ttgattaaccttttctttagtttctcctataattattggtctatctcaat
tttcttctacttcctaagttcattttgtaattttatcttcagaaaaca
tctactttgtcttcatctagattagggatttgtttcttccctgtggaac
tctttggcagttgatcaagttgatgaagttgataaagacctcttcttaga
atcatttaaaaaaatcctacttgggagtggagtcacatgacttctgtgc
cttcctacaaaatgtgtgtgtgtgtgttttctgtttacatacatg
gttttctcacaatgctatcttaatatgctcagtaattttatggaataaaa
ttgtataaaccctgcttgaataatatattctgtgtgcttgcctcctttac
ctcataacacagtgtacaaaaagggaattgaagaggaagtcaaataaaga
aaagaaaatactacccgtcaactttgcaacatgtacggcctgtgtcacca
cacaatctgtgaataataagaagttactttaaataatacttcagcagtta
tctcaatcatgtgatttgtttgaacttccaaggctaatactttcagctca
acagttatctatattataacataccgtaatgccttatggagagttaaaaa
ttctcatttcaactgtcctcttctgcaaagcttaaatagtcacctaatga
aactcaccccctttcatgtattgatgaataggtagataaaaattttag
agggaaaaataggggctgggtcaccaatatgagaacatagataagtaggc
acatttgcctggtgggtggtcagctcatttgcaggggcatctgtagacag
aaactggagattgcagtctataggctgatctaatgactgccatga
atgatagtttcacatagatgtaccaactgaaaaatgacatacagatggtc
cccgatttgatggctcaacttaagatttttgactttacaatggtgtg
aaaacaatatacattcagtagaaactgtacttagagtacccataaaatca
ttccgttttcacttcattacagtattcaataaactccatgatatattc
aacattttgttataaaataagccttatattagaggattttgatcaaccgt
aggctaatgtaagtgttcagagcacatttaagacagtttagactaagcta
tgatgttcaatcgcttgggtttattaagtgcattttcgactttaagtat
ttttaacttatgatgggtttatcaggatgtaaaacccaacatagtcgagg
agcctctgtcaacatttctgtgactttttattgatgaagttcgcaaatt
gctaataacctctcgtgtttgttacctcaaatttcataattgaaggccacgcta
cacttgagttagagatgagtggaaataaagacataattttattttaacatc
taagattatggacccattgaaacctagaatccaggattctggagtcttga
tttctagatttactagtgtattggtataaaggagtatgtaaataaatatt
ctcctttttttatgggtatatattgctatgttaaaaaattatttctagag
aataagaattatacaattgcctaaaatgtcttacttaataatgataaattt
aaattgaataaagatttttaatggctttcttttttctactttttttaatctt
atgcttttttcttattgcatgtgtacgtatatgtatataatatatatata
tatatgtatatatatatgcttcatttgagtactgaattgagtaattcttgc
ataaaaagtttgtggatttaagctgtcagagtcttttatgcccatgag
tgttttcctttactcttacacatgattgataattttgctggacatagaat
tcttggttcaaaataatgtaatctcagaacccaagaagacattttttcat
tgtcttctaggatccagattgcagttgatactttttgtattctcattctaa
tttcatgcttttgaagctgaaaataactctttttcataattttgtgaaggt
tttgtgatttttctttattttgaagttctacattttcaccaggttatg
aacatttctgctgggagttgatgttcctgtcagattaaaggtttgcatc
tgtttttttccagctcagggaatttttttattattatttcttttcattattcca
aacttattccttattaattctgttcattgaatctctgttaaataagaaa
ttgaaacttttaaatctatacttttattttttctgttttcttcacactttct
acacctttacccttctcaatgcattctgacagaatggttgcttgatctt
tgaggttgctaatctgttcattattgtgttcatgcaaaaaaaaaacaaa
cagatttttcttaaaaactgaaaatcagcaaaatttacaagagcgttctc
ttgagtatatattgggtcacagattcctaagtgttgctgtgaacatattt |

| Illustrative Sequences-All sequences are shown 5' to 3' |
|---|
| ttaccttcatttttttttcctgtgatttggaagggacagtactggttaaa
tgttttaaccaaccatcttgaatctgaatctgctgattgctatctagta
tgtgtcaggttccatgttaatcactggataaacaatgcaggcgtagagac
ctcaatcaaatagaacatcatgaacattgcaaacactaaagcattttctt
ctgaggcacacagaaaaggtgagagaaagtggagagagaggtgatctga
acagcaaattggggtctctcattctgtatactttcttaaggtgtttggat
tttattatgtacacagtaggtagctgaaaaggggtttaaattttgtgtta
tctgtttttagatagagatggcatcttgctatgttaaccgggctggtcttg
aattccaggcgtcaagcaatccttctgactcagcctcccaagtagctgag
actacaagtgcatcccaccacaccccactggttttctcaggctgatctcaaactc
ttttttgtagatatgggggtcttgctatgttctcaggctgatctcaaactc
ctggcctcaagtaatcctcccatcttggcctcccagagtactgggattaa
gggtgtgagctaccctgtctggccatgatgaaaagttttaggaaatttt
ttttttaaaaaaaataccatgcaaggatgaaaagaaagaaggcaggactgga
aagggaaaatcttttaggaggtaattcctgtagtctagaaggatcattgt
catctaaccttttgcaatggcactggagactggaaaaggagcataaaata
cttgacccaatacctccctaaatgcgcttttattagaaactggcattac
aactcatgtaaagagctacatcattaaccaacaaccacaatggtcacctt
tttgtaatttatttttgcttgttactttttccttatccacactatagtcag
gaggagtagtgtcagtaaagtttttataatttagtactgttatatgttgt
gcaaattttacatcatgtattttatgcataaagggtagatcatgggctgc
ttcaaaatgaaattgtattagaattgtgtgggtacttgagtattgatagt
ggggaatcacatgtaattctaaattgtgagcccaagtagccagatgtgat
attgagaggatgaggcaattcatccctaaactccaaggcagatactaaat
tttcttcaaatgtcattgcatggttgaagattacaatgctccctggaa
gagcagaggcattcttaggtcaaggataactctcttactagtagaattta
caataaggtcacatttctctgactagaaaagtggggcgttgggaaaattta
atagaagtgtagtaataaaagtttttttttaaaaagtacttgttttacgca
tagtcctatgtataacaaagcattgaggttattccagcaagacagatgtg
gagcaggtgttgaaatttaatggataagtaagtaatacagaggcagtaga
tcagtaatggagatggattagatcatcaaggaaatgggtataaaacaatg
tattatgaaaatgccttcgattgtttctttcaaaagttttctttatgct
agatttaaggcagagtttcaggttcaaaattttgggtataaagtgaagcc
gtgtcttcagtttttcagaattctgtgttttgtgaagctactcttgaaa
gagtcatttcccatagaggcatatctttaagtctatacattggcaaata
aaatagttttatagtctaatgtaccgaagtttcaggcatattttattatat
taacaaacgtatatatgaaaatatttttgattatgtaaaatttaaaaattg
cttgaaatttgtaccatgaattgatgtcaaataatacccaaatacaattt
ctatatattgataaagtggcttttactaaaacccatatattttgatttt
atgaaacagtataaaaattcactgaaagtcacctaatttactgtgtgtcc
ctcaagcaccagccgctactctagatacttggatacaccactgaacaaat
cgagtggaacatccctttcttgaggaacttattttcttgtgtggggagaa
agactgagcaataaacatattataaaagttaaatacttagtaaaagtat
aatgaaaaaagtaaaagcagaaaaagaaaaagaaacccaaggtaaaggggat
cagaaatgtgggtgagatattttaatttttaaatttttaaatagggtcttca
aggtgggactcgttgagcaagaaacattttctgtgaagacatgaaggaggt
gaaacagtagaaaagcattatgaagtgctgccttaagcactcttaaaaaa
agaaatttgttttcataggggaatttgcattttatctttttacttaattgc
tgaatttatttttgattagtcaaaattccaaattcacattacccccagcattg
ttccctaaaatatactgaagttatttttacatcaatgtctacttcttttgg
aataatttatatcaatatatttgttcatgcctatctcagaatccaaaatg
taggtgcccctctttttaaaaagaaattatatatatatatatatatata
tatatatttctaaaagatgaatgcatcttcactccacatctcaacctgca
ctgtatttgaaatcataaagcttttgattctaagatgatacaaagtga
tatagggattttttgatggtgaattgtagggcaaaactatttgaggtattatt
cttttttgagttcaataaatagttttccatttgaaatattcatgttttgcc
cttccatatgtgtttcattttcctacctgaacaataattgtttgctgagga
tataaatgcctgtgcaatgttatagggagacagtaggttcaatctgattg
cactgaataaagtgcagtgatttgcactcactctttcataagatattaat
tttggagatttattggagtaaaccctatacattatagatttttgcacttt
tatctatttaaaaatgtctgttttttattaccttctgacgattgtctcact
gtgctaaatattaaactacctcttttttttatttagtcattcttttaaggaa
ctatgagtttcatgtgccaacttttaatttaattgattaaaagcaaaac
taattttcttaatcacagtttccttggcattgcacagctcaacttgcagt
tagagaaaagaataacaaaacaaataagcaatctgtacttaaaaaaagttt
tggacagtaaaacaaatgtaaaattgtactcaagtaagcaatgctaatt
aagtggtagagttgtattttaaatgattaaatcaatgaaagaaaatatct
tatgccttttcttttgaaaattaagcacttttttgtgttcttattttggt
taggataatttggtgaggataactcaaagaatagttctggattattccta
ttataagaccaaagaaaatgcaagatcagtatttgcagagcttgggtggt
atatgtggagcaaacaaaaagggtcagaaaacttttattgcttttgagtgt
gtgtgtatgtgtgtgtattttcagtgtgatgaggaaaaacacctactaat
tatgctaactttgcagcagtttaaacataacatatgatgctactttcttag
ttatgcgataaggtatgtgtttgctgctgtggttgtgtgatataatgttt
gcttttcttgatgtgttacatatcttacaactaatgacctgttttttaa |

| Illustrative Sequences-All sequences are shown 5' to 3' |
| --- |
| aatgtacacatatgacactaatgctgaaacactaatgttatgctttatta |
| ggatttaatgtatggcaaataatgttcaattttttagcctccactttat |
| gcagatttaaaaaaaactcgtactatttgctcagccccagaaatgcacag |
| aaacaaatagggggaaggcttttgacctcagtgaattcccaggttattggc |
| aaagtcaaaggggctacagaagtcagtatcatagtgcactgagggaagct |
| atagccactatgaggccatgtaaaaagaaatgtctaattcaggggtgaa |
| gcagttgggagagggggcatttcagacaaaggcccctggaggagatggatt |
| ctgagctgagtgtctagggaaagcaggatttagttaggtgaagaaggtat |
| agggaagacctttcagtcagggaaaacacagtctacaaagcagggatgca |
| agagagaacatttgaaacacttgtcgttgttaaatgcaatgacattcag |
| atatgccattttcactcagagggaaaataagcaaaattgaagtgccaagtt |
| tggaaaattgatatcccatttcacatctgaattattgagaaatccttaaa |
| cacaaaatattcgttcctctgctgtttttgaaaactgaatgtttgaacat |
| tacctcttctgctgaaagtaaacacttttatagtgacccaaagttttcctt |
| gattttcctaaatatactctattagaaagaaaatatagattttcattgca |
| tcaggaaattcatatgatcgatttgttgcatttttttggaatgagcaatac |
| acaatgaaagaagattttgcttttgtctggagccaccttcctgggcctgc |
| tagcaaacttgagaccctcacgctttcacacctgaggcacagctgcaacc |
| acatcaaggtcatcagtacaggatgttgatgcacacactcacacagcac |
| aaataataaactacatgcattttccttggggcaaaagcaaatggtatgg |
| ttgagttttcttttcttcgtcttcagcaaagtggcatggtggacattatg |
| ttttatttaaaacttttaaatgacatttatgtattttcatacataagtg |
| gaattcaattctgttgggcccggataactgggtgtgacctttggactgtct |
| aggtcagaataacctagaacattttgagaaggtacaaattccctggttct |
| gctcaagatctattgaatcagaatctctggctataagtacatatgtttta |
| tttttagcaagtccccaggtgatttcttgtcactctagttagagaaccac |
| tggtatacattttgcaactgctttggccctgggttaagtatttagggccc |
| caaataagtgaaaaccaatagcatatgttttgacacgatccatccaaactta |
| aaaaatatttatatatacatttcagaattatagtcttgtagccttttttat |
| aatttcaaaactccttctagccactatggaaaacaccacaaacataacttt |
| ttttgtgcatctaatactttcagaaagtccaaagctcaatttgtatgaagca |
| tggactgcctagcatttatttcttcctgacacatttgattttgtcttaca |
| gaaaatttttttctttactaatttatacctctcaaggttacatttgcctac |
| agactctttctttcagtattttcgtatttatgatgggcactgaaacctatt |
| taaattatttctgacatacattttccttcaaatgccataaacattttctt |
| gtctcactaaaatgtctagtgttagtttttctgtatttctggttttaaaat |
| atgtccacaattactattcctcaataacaattttttgcataggagatcttta |
| tcttttcagatagtatcataatcccctatgctattctgtaaaaatacctt |
| ctgagtcctcttggatgtataactggagcaagtgaagggcaggaatgatt |
| ttaatgttttttcttacctctgttttctccatgccaggtgaaagaatgagt |
| gagctgtgtgtccctttataatgtaaggacattttccagcatcactcatgc |
| tagaaaagcaaactaatacgggatcctcaaaattaaaactgtgaacacata |
| gaatgccagagcaaaatctcatcctttagcatctcatttctgaacagttgt |
| gttactctgtcagagttcaattgggaacaaaactattatgatatacaga |
| atccataatagaaagacctttatacaaatgtgagggtaaagttgaagaaat |
| gtccaaaggaggaggtaaagattcaaataaaaaggaccattcagtggtcc |
| ttttgacacactggtatgagagaaccagtagcttacaggaaaatctggga |
| agcaaagcatgtccagatgctgaagttgtactgtgaaggggtgagagtag |
| agaagtatatggaaagctgttgcctctgtgtcaggtggtgtgtctgggt |
| agcatttgatcagcagtgccacagatgagaagcagaactggacatggaag |
| agaagtgaagtaaggacaagctggaatctataggcatctctgcatctatc |
| tttcactgcatctagccatgacaaactcagagtataactgactacagctt |
| tatctccaactttttttttttttttgagatggagttttcctggctggagt |
| gcagtggcgtgatcttggctcactgcaacctctgcctcgcgggttcaagt |
| gactctcctgcctcagcttcctgagtagctgggattacaggcatgtgcca |
| ccatacctggctaactttttttttttttaagtagagactgggtttcacca |
| tgttggccaggctggtctcgaactcctgacctcaggtgatccaccttct |
| cggcctcccaaagtgctgggattacaggtatgagccaccgcacctggcct |
| acctccaactcaaaaacctcatgtgaatttcgattttgatcaactgtaat |
| ctggaactgtaagtgaaaggaaactttgggaaaattcttccagcatagcc |
| aatttgataaattatcaaatggaaaccttttagatcttttatgagtttaat |
| gcatatacttctatattttctagagcagcatgttttattttcttttttcag |
| ttatagccaagattttgttttaaactgcttttaaaacaggcagaaaactat |
| agcctccccctccttcttttatacacttcctacattattgatatcctatt |
| tgataaatgtattttttccttattgacaaatatgattttgagaagttgta |
| tgaaatctctgaagacattaggacctgtgtcttcatgacttgagccataa |
| gtcattcagctctctggatctgatccaccacattacatagcacatataag |
| tctttttgatagccgcatactttgagcccaagctaaggaatcatttgtcct |
| tgctgtatagcaaaccaccctaaaacttagagggcttaaaacaacaacaac |
| tccttatttatcctgattctgtgggttggctgagtgcttcctctgctggt |
| ttcatccaggttcactcatgagggtgagttggctggaggataggctaatc |
| tgcaaagtccaagatggcctcattcatatgtctggcagttggtgcttgct |
| gttcacaggggcatcttgtttgcttttgtgtgctctctcatcttctagg |
| aggctagactggcttccttttatactggtctcaggacagcaccccaatac |
| aacaaactggaagcttggagaccttttaaggcctagcttcaggtgtcaca |
| caatgttacttctgcacattcttttttgtcaaagttcttcacaaggcaagg |

| Illustrative Sequences-All sequences are shown 5' to 3' |
| --- |
| ccaaatttgaggagaggggaaatacatttcacatcttatgagaggagat |
| gccaaatgctgtggccatgtctttcaatgtacagttgcatcttaaacgag |
| aaattatcttttagttaggtttcttttagtaagaaattccaccttctgcct |
| ccctcatcttccctcccaaaatacacagacactactagtaatttttgtata |
| tgagtggttctcagttgagtgcagttttgtccctgtcttcctcaagggac |
| atttggcaatgactggaggcattttttgattctcagcgagactttgggagtt |
| actactggcgtctagtggctagagaccaggaatagtgctacacatcctac |
| aatttatagaacagctccctgttacaatcagttatctggtccaaatttgtg |
| ctgaggttgagtaaccctgccttatatggaatataatgctagcaagttgc |
| ctgagtaaaacttttggtcaagagtaatacctaaaggtattctttttacac |
| agtctgaaatgatttaaaattttgaaggaatcataaattttctttttgggt |
| ggaaaggggctagttatggaagctgccttttctgtcattcattatttatga |
| gcaaaccattttagatagaatatgaccactcaaacccttcttttaagattc |
| aaactgaacacagtacttagacttttcgagactctgcgtgtttaattttca |
| cctctcattctggcttttaccttttgtgtgtgcacacatgcacattgtttt |
| agctactttttgtcagaaatctttttaaggactttttccacattgttttaaag |
| gttgaaaagtatgtattaattggtcaaagccattgtctctcattaaatca |
| ggaataacaatttacatagaaccctgtgattttttgtacttgtatctttag |
| atatgggctagaaaagttaaacattctctaccatattgttgttatgaga |
| ggctgaaattttcaagatttccctccagaataaaacatggtgcaattta |
| aaacaaaatgggacaaattggtgataacgcaaaacaagaattgtgtacaa |
| taaattagatttccttggggcagagaaaaataaaaatgctgaaagggat |
| actgggtacagttttttcattgttttaaataagaatttttaaaaataga |
| aatgggcagaaactgtttatgcattgtagccctttttccatattccaatta |
| caattcttgggttactcctggcttgcatggtcaccaagtttggttattca |
| tgtttctcaccctaacacaccccatctgctccctcctgaaggtgtgtgat |
| cacaggtatcatactttatcaagcaatatgtagtgacatccccctctcaac |
| tgacagaggctgtttgttgttgtgcccgttccaaagcagtgtttgactgat |
| aatggtagagtggtacataatttgaattcctcagtagaagtttattacat |
| tagctcaggcctgaggattcttgcacaattttgagagaaagagagcacaa |
| gaaagaaagacagagaaagataattctttgaaaattcaagaattcatttgag |
| atcaataaaacagttattctaatctgtggatgagacaaacccatagctg |
| taattaagatcactttggttgtctcaacaacagattaattcctctttttca |
| gttaaaaggttgatgtcatgaaagcaatattttactggagagaaattgct |
| aaaatctgtttgcttaacaaagcaattattgataacctgcaattgcttat |
| tgcttccctgtcatcgacttgttggcaaaaacagtctcacgtctccgata |
| gtgatgcctacttttacttcagggaagactgataaataatatagtttttca |
| cagaaacatgtaagacaacaataatccttaaactatgaggcatcatatcc |
| acaaaaattgaggaagcgttgctgaagtactaaacatattgtttgagttc |
| tctgcttcaggagtattgaccttttgacttttcaattgatatctctctttcag |
| aataatagtgatgaataatggaaataaacgtctcttaacttgtggtgtcag |
| caacaagatctttttcctttagggaacttaacatatgggtatcttccaggga |
| gcggataaatgaactgattttgaagtgctctcctaatgcaaacatttttct |
| ttgtaactgcctcagaaaaatgcaggcatccaaggtaggccttttcatcagc |
| cttgaagtagttgttttgtttgcttttttattttttgtttttttacaaga |
| ctcttccttctctcactcagaaataaatagcaacagcttcttgtgacatt |
| ggcctatatcttgagttcttaaaagtgtaaaacactggttttgaagtatt |
| actgcaccaatccccaaggtataactacactcacttaaatggcctcacaa |
| ggatagctgtaccattcttaccactttagggtatcacttccttttagatgg |
| tagcaataagaatagtgcaagattaagactcttttctagtagccatggta |
| agagtaccacctgacatttgtagagattgttatacattttcaaagtatac |
| ttaaatgcattagagaagaggcagtgtagtgtaaaggtcaaaaacttag |
| actttggagttaaggcaacacttttttagcaatgtaaaggcttagtttct |
| ttatctgtaaaaatatagataatagtacctaagttgtagcattattataa |
| agattagatgtatgcgaatagcttagtcttataactgtgccctagttagc |
| acagcataaacggtagctcattgttactaccctaaattaaatgacaggtc |
| cttttcactgtttttatatatttagatcttaagatagttattataaattt |
| attgctacagtacagaattttttttaaaaatctacatcggaactgagat |
| ccctggaaatttgcaccacattccagcaaagaggcacaagagaacaaga |
| taggcagttgaattctccgtgaccaaataaaccacattctcatacaaagc |
| gcctccaagatcacagattccagctgacatcttctaaatagtatcttaa |
| atactgtaaacatggctaaaaacatcttctaggttatcaattttttaaacca |
| gagactaaaatttggatagtgctgacggagcaccaaatagtgctgaaaca |
| gattgcatcagcctcctatttttgcactccatgccattaggaacaccttc |
| ttttacgatctttttctgaggtgctaattcactaaacaaacagtacatgt |
| taccccaggcaccaaatccttcaggatgctcccaagttgcccattttct |
| tggaatggtttgggggccacagaaagctcaagaactgtttcagagcctgc |
| tgcctggggtgccaaagaattatgcacgaataaaaccctgcggggaaaat |
| gtaagatgctaacttagaatggatagaaagaaaaaagaatggatagaaag |
| aaaaaagctttaaaccatcagcaaaattcaaattagaaagggataggtag |
| tcacaaaaatgatctgaattgtgatgtaaaacaaaataacaaaaataacat |
| gctgaagtctgatgttctggtgtagcaaacccattcactaattctgaaat |
| ggaatactattcttatatgatgcacattatagtcccaaatgccaaaatta |
| gaacttagacatatataatttggggagacctttaaatatgagaccctct |
| ttgagcatttaaaaaatatttaaacatctgaaaaatgatgtacatacatct |
| ttttagatgtatatatattctatatcgatttttttattggaaaatcta |

| Illustrative Sequences-All sequences are shown 5' to 3' |
|---|
| agccatcattaccctgagagagggcagtcaaggagagcagaagagcccca |
| agcatgtattctcagagtccgtttactataaattggaaaagacaaagaaa |
| atgataactgtaatcaatttgcctttaccttgatgtcattctagaatttt |
| gaaccatttaatttgttttctcccaatcctggccacagcactttttttct |
| cctttagctattcattgagaaaacatgagaaataagggaggcttcaaga |
| atggtttgaggtagtatgtccatccccccaggttgaagagtactctgccat |
| ttggttttggtggcttctccttgccttatgtttatctaggtctctggctt |
| cagatctggcatacacacaacatctgtgtgtatgttgtatgtgtatttta |
| gatggttgtcttcaattagagaataatacttctgaggtggcatctcaggc |
| atagtcattttttaaaggagttcttactttctgggtatgttttgcttaga |
| gataaaatatgtttatcctccgttttaacaccaaaagagtggctgtaaaa |
| cagttggatccaaatgttaaaagtaaaatgggaaattctctttgagcaga |
| gtgtgcaaggaaagcaatatttttgtacagtttgctattgttttatgaat |
| ctttagtataataacaccctgatgttttactcagctcatttatgtgtctg |
| catattcactccgaaatccaaaatgtcatttcaaacattcccagacatgt |
| taattcctttaagttggtgtcaactattttcatatttcccaacttatcaa |
| ggtataatggaatgaattacaatttctagttcttagaaacagctagaaaa |
| tttgttcagcttggtgtttaaaaaaagcaaatggccagtccttagtttct |
| gcttcctcaaacagtttatgactttgcaggagttatttcaatgacttctct |
| tggtaactgccaagccatctcctgcatttgatttagtttctaggagacat |
| tttctagaaaaagaagagaatgcttgcaacaaagatggcaaatagaatta |
| ctgaatgtaaccctttcctgtaggaatcttgatgggagtaagcaaatgt |
| ttgattggtttcaccaacctgggtcaagttgctatgtgggtgactctcac |
| ctggagatctggtgtgagagactgaatactgaagtcttgagagcatggtg |
| ggaatgaagggctgagacaagggcaccaaactcagaagaacttaaagcaa |
| tgtcaggagctgagatgtggaacctggaagctaaggagagcatgacagtt |
| tgggctgaagtccaggtggtcagacagaaattcagtgtgcatgtagttat |
| gggcattctaaggttaggttggattcatttataggacttttgggtgagcc |
| taagacacaagattcacattggctaaacccacttactatatcttaggata |
| acaaattttatcctttacataaagatagtatctttaatttgtttcaaaac |
| tatgtcttgagcttcataatgtcattgaagaaggggatgagattaagtta |
| gaatatgctctatttcctgttgcaggatttaaattatgaatgaatgagtg |
| tgtgaattagatctatttataagttaactgtctccatctcctttgtttat |
| aaaatagcttatgtgttgatttcatgacagaaaaactcagccttgaagg |
| ttttcccaacaaaactataacttcacttaagtttttcattttctgactc |
| ccatacaccccaaccaccctccacaaacacacacacacacacacacaag |
| cacacatattttacagttaagtataagatatccctctggaatttcatttt |
| ttaggggtctctaaattttttcaagctctctctttttttaaacttctgt |
| ttttggttctattcccagaaccccatatacacctcacccagagttttacctc |
| gaatccactaatttactgcccatgtcatgaaatgtaaacttattcaatagg |
| tgaggtttttttttcctcctgagaatcccaaaaagaaaaatcatgaaaatt |
| gcatttattggtcagaattccacgtttcaaagttctgatattttagtat |
| ctgatcaggagagaaaaagtctttcacatggaaattaaatgatttatac |
| aaattagtttgaaatttgagatagaaataagatcattgaaatatattcag |
| agatttagcctgaaaatacctgagtcttgaggtcatcatctgaaacaatg |
| tgccttattattttgaaataattataaagatggttcgagtaagcctatag |
| ttctagaaaattccttatagagttactataaatactgaacagtagtcttt |
| gaatcatggggatgaatgtttcatataagtcattcacaaagtggctcag |
| tggacaaattttatctcagaaagagaatgccccataggagttaaaattat |
| catggctgagaattcctagatgatgtcaccagaatctgaaaacactactg |
| tggatgcaataatgatgctatctgcattttctgggtctaacttctgacaa |
| ggaatctgagttttctggcaagcagaatgcacatcagagtacacaaggg |
| catgtcttggcaacttccacctgagcacacatgcacggcttcctgttttg |
| gtctgatagcttccctgggcttttgttaatgcaaaattacccacacaga |
| gatgggttgcccatgcaaaagagtaggtgtcttatttttgggaaagtttgc |
| ttcacattatctttgttgttttattctactaaccctatttcctctttttat |
| tttacactagcgttttaaattcacttcatttgtctgtgagaaatacttcc |
| ccccgccccctcacttcttaggcttatttctcttgttatctgtttttctt |
| ttcttctctaggcactgccttattactgcttcatttgtttgcaatattaa |
| tgtctgctaaaatgtcttaagatatacaatgttaattcatttgctcaatg |
| atttaaaaatatcttggtgagtctctcactcctccacatgtacatataccttt |
| ggaggtaggacaaaggtgccttaaatattcattgtactttcaggtttata |
| cagtttgggttgggagttatactttcacaaactgtggtacaaaaataaaa |
| agtgatggcttctataaaaggtaatgatgaaatgctatgaggcattttct |
| catgtgcttttttggtcattttgtgtgtgcgtatatatatattccttttgtg |
| aagtgcctgttcaaatctcttgcccataattttccactggattaaaaaaa |
| ttgcattatagaaattgttacagtctaggtacaagtcctttgcatgta |
| tatattatatgtacatacatgtggcttttaaacctattttcttacgattt |
| taattctgtgaagtctactatatctttatgcttttcctttaatagtgag |
| tgctttctgtgtcttgtaaaaggatttttgttattcttaagtcactaa |
| gatatatgcctgtgttttcttgatgtctaagtctacataataaatcatt |
| agagaaatgtgaattaaaaccaatgagttattactacagagtcactagaa |
| tggctacaactaaaagactgacaatactaagtgttgttgaggatgtgaaa |
| caagtggaatcaccatacactgataatgagagtataaaatgacaaaacga |
| cctaggaattagtctggcaatttctcatgtaaacatacacctgtcctacg |
| actcaccatttatgcttttaggttttactaaaaagaagtgaagacatgtg |
| tcaacaaaaagatttgtacaagaatgtttaaagcatccttattcataata |
| gccagtcactccaatgtccatcaataaaacagtagataaacaaactttgg |
| tttattcatataataagaatattacttggcaataaatatatacaaattact |
| gatatacataaataatataaattattctcaaaatgctgagctaaagaagt |
| tttccacaaaagagtatatgctatatgatttcatttatatgaagggccag |
| aataggtaaaacttcacctgtgatgaaataaagcagtggttctgtggtctg |
| aatgtttgtgtctctctcaaattcatatgtttgaatctacttaccagtgtg |
| atgacattaggaggtggggactttggaggtgattaggtcagcaggacag |
| agccctcataatttgggatttactgcccttaatcccaattaaaagtttcca |
| gaaatctctcttgctccttccaccaagtgaaaaaaacagcaagaaggcac |
| tatctataaatcagaaaacaggccctcaccagacattgaatgtgctagtg |
| ccttgatccttggactttccaccctccaaagctgtgagaaatataatgttgt |
| ttataagtcattcaatttgtaatattttgttagggcagtgttatgctgac |
| tgtaacaagcgggggattgactggaacaaacaaggaggaaagatgtgcttgag |
| caatggaaatgttatatatatagataggaggtgtgagttataacaacagttt |
| atcttcatcaacactggggaatgcacatttaagatttgagcatttcatt |
| gtatgcaaataatacctccttaaaaacaatgaaaaagttctagagggcaga |
| ttttgcaattaattgattagaaatatggcatattggtttacatattggggt |
| tatactcaggagtctcaaaccatagttctgaaacttattagctggcaaagt |
| ctggtaagtaacataacctccctgaacttgttttcccttttgcacagctag |
| aataatacttcttttaagagatgttataggaatgtatgtaaaaggcttat |
| cacaagggctgacataagaaattactttattgactaattctcctcctttt |
| tgtccttcttctttgtttattacttagtaaagtgtcaaatatggctgtcag |
| gttttggttgctgctgtttgtgaagatgataaattgttaacagaaataca |
| gagcacactagtaagatcatacctgggagagaataatgagtcatctaatg |
| aatttgagacaaatagggatgtcctgaatgtagtgtcaataatgggtctt |
| gaatttgggagagaaatcagaaaaggagctttggatctgaggtgtgctga |
| acagatacaccagatctctggggatgggaagggtctggaaaggtgtgact |
| tgtagtatttgctggtttccatgctgtaaatactgtgtcatgaccaattt |
| aaagttaccaaaccagattgcaaaattcctgaatgtttatcagtcagctc |
| ttttcagctggtgactgccacctccagcaaactgctagatctgagtcatc |
| tgctgagacagagaatgagaaagatacaattatttttctcaccttacacca |
| ggtcttcttgcttgcaggatacattgagtttaattaaatttattttgctat |
| gaatccccatttctgaatgtctctctacagctcacgctattttcagttat |
| gtatgaaaaacacttttatcttcttgtgcccactaccttcaaagagggcct |
| ccttttttataatacagaggccacccagggcccactaggcctcagtctggg |
| agagattcaagcacagcctcacactgtgaaaaagagcaactcttccttc |
| ttttcctcagtgctaggcttctgcctcacttaagaaaatatttcattctc |
| tccttgctgggaaagacagggacactttcaaatctagttcattatctcct |
| acctcccattcctccccctgtccagttcataagtctgtctgcatgaccg |
| caagtgtagacagggttgttttcatgagctggaggaatactgacaaacca |
| tggaatggggtttaaaaactttatgtaatgtcatagagctgtctatagcaa |
| taagagtacttttgttaagagtacaagaagactcttcttaacttacaggc |
| aaactaaacactctgttaaaattccagaagttctttgtcctaaa |
| aataacaggaatgtaaagaattttttgcccagggatgtttcttttcaata |
| ttacttttttatagcaaaataaaatgaaaaacaaacaatcaacagaactat |
| acgcccatgtttccatggtaaaatgtgacatactcattaaaaataacatt |
| atgtagtcctaagatgattatgattgttattatttttaagacagaa |
| tctcactccgttgcccaggctgagtgcagtgcatgatcttggctctct |
| gcagcctctgcctccatgttcaagtaattctcctgcctcagcctcctga |
| gtggctgggactacaggcacgtgccaccacgcccggctaatttttttctat |
| ttttagtagagacgggtttcaccgtgttagccaggttggcctcgatctc |
| ctgacctcgtgatccgcctgcctcggcctcccgaaagtgctgaaattacag |
| gcatgagccactgcgcctggcctccttaagattatcaatgaaaaaagtt |
| ttattctcatgaaacatgtttatactatacttagtatggcatttaccat |
| tttaactgttaaaaatacaaaggaaggaatgattggaaatgaagttttca |
| gactgttaagtcactattattaccgtgaattttttcttttggtagtgggat |
| tttgggtggtttcttcctccttctctgtgcacttaagtgcttttccaaat |
| tttctatacaacaagcaaaaaatatctttcaataaatttcccgatgccccc |
| agagaccacatttatattccaccatcttttgtttatctattccggttttt |
| ttttaaattcaaaaccatttgaagtctatagtcaaattatttttttataac |
| acatataggacaaatgtctagtagcataaaaatgggctcctttagctatg |
| atgtacagtggtgtccacctctctggttattttctcttgtgcttcaataaa |
| gaaggctagtttaaaaaataagaacctaagctttcctcactgcaaagtac |
| cttttaacttgttggcaattcaatcttcaaaccctttaaatatgtatgta |
| tatctatatctgagttatacgttttcaacattttattatgaaaaatttca |
| aacacacagaaaagctaaaaaattggtacattttatactactaatagacct |
| atcagctagattctataattaacattttagtatctttgcttctcacata |
| tctatttacccttccatcaatccatcttatttttttgatacatttcaaagt |
| aagtagcagaacgagtatgctttgctcctaaatactcttccacgcatgt |
| cttttaacctgaaagagttcgatgttttcgcttttttttcttgcttttggg |
| gtaaaatttatgtgcaatggaatgttgaaatcttttagttaccagtcagtg |
| agttttgacaaatgtgtgtctgtgtcacctaaactcttgtcaaaatat |
| agaacatcaccataatacgggataatttcttcatgtttcttctaagtccc |
| tgaactgcccatcccagagccaaccattgtcctgatttgattctacaatg |
| taatgttttttccaaggctagaactgcatatcaatggaatcatacagcatg |

| Illustrative Sequences-All sequences are shown 5' to 3' |
|---|
| cagtcttttgtgctattttcattcagcataatgtctctgctgttcatccg
tgttgttttgtttttttagtcattttcttttgttgccgagttatctccca
ctgtataagagattgtttaggtatccattttcctgttgatggatacctag
attattccaccttttagtactatgaacaacctgtacgactcttttttgta
ggcatctgttttcattgctcttgggaaaaacctaggagtagaattgctg
gatcagaaggtagatgtgtatctgggtgttttttttaaaagaaacttctca
aactttttccagagaggcttatcatcttacactccaatccacaattcata
ggagtcctattttctctatattctcggcaatacttggcattgtcaatcc
tttttttttttaatttagctttattatgtgtgtgtagtacctgaattgta
tcttttactgtatatatttaaagtatatgaattgtattttttaaaatgttg
aaatgtttggtcaattctttgctgtctaaaggaggaaaaggcaagagag
acaagttttgctctaacaaacctagacttcctgagtccacagcacattga
aattggcacaatcctagtattttgtaagaatccatttttctcccatgaag
aactttgttttcccaagatttaaatggtaattactataggctcacttcac
cattatcataatcatgattgctggtccctcctcctaagtccttctctttt
gtttcttcacttctcaattcattaagactacttgtaaggatttatggagtt
gcttcatacattcctggcatctttgtcaggtaatttcctctgtctcatgt
gttcttaggctgtaggcatttgtgtccatgtctgattcttttcttaatct
ataaaaattttgaagaaaggaaacatctaatttacccttagcacagccact
tgcacctagtaggtgctgactaaacatttattgaagagatgatggagtag
tgaagaacacaaaccctagggctagactcttccacctaccagctgtgtga
tatcaagcatgttacttaccctctctaagcctcagttccatctgaataa
tgaagataataagagtacctaccttactgaagttttgtggggattaatga
gctaattttaaaagccttagaagaatgctaacatactatgaatata
tacaaataaaatgaaaccaaatcatctttggatcatatcaattttata
gaaaactctggctttctaaatcaatgtctaccctatttggaaattttct
taaaaacaacaagcaaaagcaataattcaatctaaagctatttctt
tcaagtattctagttctgttattccagaatttggtgaatgaatctattta
tccattatgattttgtagcctttgatcatatgcctctcattctccagatt
ttcagaggaagcatgtctgtaatacctttcttttttttcttatttaggggt
ctttattatgtcttccttgaagtgctctgatcagatctgcagtactgga
gatgtaaattcaactctacttttttttctttttaaaagaagagcaacat
aatccttagtgatcctaaatattattcaacttatcttaacattcaatttc
tttatatagcaaaggaatgcattttttagcaatgaaataaacagcaaacat
tgacattgcttattaacagtatttacggtcgaagtgccccacatattctg
aaaggttatgttgtacattcttttaagaagacttcagggttttctactga
aagaatttgaaaatcaagacttggaagggtcctgagagcaacattctata
gaggaaaaggctaaaaagtaccccaggatcttcagtagcagtgatagtat
ggctttgttttccttcactggactaggctccataactaagcgtcttatat
ttggaagtcaaaatgcattttgtttgtcttcttacaacatagagaacacat
gcttacaaaatcaaggagagcattgactattgtgacctgtttaacatat
ttctccgctttgcttcggatgagagatttcaaatctcatcattaatgtgg
tgaaaaatattgaattggaaaacactaacattgtcttcccatattgagtc
attgtctgttttgtaacttccaaacaagaaaaagatattaatggtcacctt
ggctgtttccttgtgacctccaacatggctcgcatttaaaattgaatctg
gactggggtgtctgggggtagggagtggaaatctacagggtgcagaataa
aggctagatgtgtccacttggtattaaggaaatgcttctgcaagcacaaa
aagaaacaatattttggtaaaaatgaatgtttttccctgctccggcat
ctgcttgcgtttacaatggccgcagtgtttttctttacctggtaggtggc
ctctccatgtatcgatgaggcactgcgtgaaaatgtgcctccttatgtcg
gagggaaatttgctttcacttcttttccctgctctcctgtgcctcccttt
gttctaatcatacatgtgaggagaaaagccagtgatatcagcaatcattt
tcttctccagccacttttttggagttaataattcaaacagatcttttacaa
actcattttattcttagaaatggccttattgctaacagtctgctctccag
ttgtactttatcaagcagcagatctgttgtaaaatgtgatgactggattt
catctgttttgccaccccctaagaattcattgcccacagctgcttcaactg
ctgttataagagacagtttaattttttgtggtacattgattgataactggg
ctccctggtaacatggtcttccttgaataggactgctgttttctaggtct
cagatccctgaagatgctacataactccctgtatgaaacaaatcttcca
cacccctaatagtaatatccaaatccccaaatgaacagaaaatacacaca
aatgcctataggtatctcaatttcatgcctgtaggtgatataatatggaaggga
agttcccctcggccttaggtgtgatgaaatcagcgaagcagaaaaaacag
agaaacaaccaagcaaccaaccaaacagaactggaagacttgtcacaatt
ctgaaaagttgtctaaactggtctatactgagtaataaagttgcaggtac
ttcttactcctgactaattttctgtagctctccaggtgaaccatgtagg
atacctgctatgtatctcaaattaaaaataatagtaataataacaaca
aaagagagggcaaaatagttggcaaaaggagaattgtaaaagatcata
aaaacaaggggtagaaggattgggtaaagagatttgaatctccaagttat
gggagcaatcttatcatcagtatatgaaaaacaatttttaaacaaaact
ctcattattcttttcactatcgagggccaaaacttcatgtttacacac
acttcaagaagaggacaatgatgtaggtcctaataaaaccattactact
ggttagtaaatttgctaagcctactgctgaagaaagttgagggcttgg
ttaaaaccttagcagataatttagcacaaaataagttcttaggagcctaa
catgcctgatgattttggtgaaatctgtttcttcccaaccatgtacatcc
aatgactgatgcatttggtggcaatgttaagttggatggtcacaagttct
aatctgatatcccatgttgcttcattaatgattggtccggtccctggtg | accactcctgtatccatttccagagcaactcttactctgcctactttctt
tttgcttgagttaaatgcgatggttagataaaactatctctgtattgaat
gttattcattcaacaaatatttattgagatactataatgcttcaggcact
aggagctggaattcagtaatgaacaagacagaaaaaaatttctgccttcc
tggaccttggactctagtgagtgagaggaataataaacaaaatacgtaaa
caaagtaaattgaaattagatgaaagtgaattagtggctcacgcttgtaacc
ccagcactttgggaggctgaggtgggtgaatcgcttgagtgcaggagttc
cagactagcctgggtaacatagtgaaacactatctctatgaaaaataaaa
aaattagccgggcacggtggcgcatgcctgtagacccagcaacttgggcg
actgaggtgggagaattgcttgctgctgggaggcagaagttgcagtgagc
taagatcctgccactgcacttcagcctgggtgacagagcgagatcccgtc
tcaaaaaaaaaaaaaaaaaaaagataaggcgctaatagtccagaaaggagg
gtaggaaggaaagttttagacagagtagccaagggtggtctcattgataa
ggtgattttgatgaaagacctaaagagagttgggagtggccatgcagaa
tatctggtggattagcaatccagacagaatagcaagtgcaaaggctgtg
ggctggacatgcccgacattttttgtggggaaagctaaagaggctgggat
tactgaagtagagtcaaatgagggagagttataaatgatgtcacggagg
taatgaagaccaggccacgtaggatcttacaagccatgaaaggaacattg
gcttttgctctgagtcccatagaagcattggagcttttgtgtgcacaaa
acactggagggtttttgtgcagaataatgaatgtttatgttgactgagaata
gatgaaaagagtgcaagggtgaatggtgggagatcagttagaaggctaca
gaagttattcagagaggataggatcagggtgacggtagcaggggtggtag
gtagtcatgttctggatacatctttgtggtagaaaacgatagcattttgatg
atgcctgttagagtaagagtagagttatggctacaaccaaaatatgaatc
taagtaactggtagaattgagattcaatgaattgaggtggggaagactgg
aggaggttttttgtggcatgtgtatgtaaagacactgattttggacatg
ctaagagtaagatgtctattagatattcaagtggaggtagcaagtaagca
cttgaatatataagtctgtagttgaggaagaggcaaagttggagataga
aatttgagtatcatcagcatagatggtatttaaagccatgagattaga
tgagatcccttagaacacctctgagagaaggcatctatgaactgaacctt
ggagttcagggagatgaggagaaactagccaatgaagctgagaagggagtg
gccaaaaagagtactgctgggcatggtggctcacatctgtaatcctagc
acttttgggaggccgaggcaggcggatcacgaggtcaggagtttgagacca
gcctggccaatatggtgacaccttgtctctattaaaaatacaaaaattag
ccgggagtggtggcgtgtgcctgtagtgccagctactctggaggcgaagg
cagaagaatcgcttgaacccagggaccgaggtttgcaagtgaccgagat
tgcaccactgcactccagcctgggcgacaatgcgagactctatctcaaaa
ataaataaataaataaaagagtaccatgtcctagaagaaaagtgaaaaa
catgtttcaaggcagatacagtgattgattgctgaaaggtcacatgtcgc
tgaaagacaaatgatgggaatcattgaatggagatttagtgaccaat
ttaacaatatagagttgatcagtgacctcagaataacttcagaatatct
gttgagcacaagtctgaagtaacccaaaacagcttatcaacctctatgga
ttaaataaaacaatgtgctcctgtgtaagtaacttgttttgaaagcaagct
ggagtgagggagctagatattgagagtttcaagttccttaccatcacgtt
cttgcacactaaagtattgaaagaatgtaatattcaaaacaggcaagcaa
acaaacaaatagaacatcatctgaatagattatatgtaacagtcttcaat
ggaaaccatgacaacagggaaaagaggccttgtaaaaaaattgtgtgtgt
gcttcctgctctgcttttctcaatgtattttatcatgtcatggccttggcaag
aacaagagggtagagataaaataaactgatttctcatcttttggaaaaa
aacaaaactggcctaatgtaaatggataaaagtcctctctgtagttgtca
atttaaacgtaaagccccaatttaaaaaaaaagtgaatggtgttgcagtt
gtgtgggtggatttggtagggagttttaattttgctacagagtggagttta
atctttgctaaagaaaagtatatccctttgattttttttagaatgcccaa
ggtccgtctgatttaaactagtattggaaaaagggaagagagatggaagg
gagtgatcaaagttggaaaacgatagaacttcccccccatgaaacacaaga
aaggtgaatacaggtgaaaaataaagatagtgctgctccacatgtttgga
attgcattttttggtagtctcaactaaccgaaatgcagccacttagaaag
gctgtcacgaagcttatgtagtataggataggtgtgggactgcccctcag
ggcagaggggaacattaaacatactgattcctgttggttatttgatttcc
tcttttgaggttagtgacagaaaacttacttttttaatttgtgacctatcta
ggagtggggtacaaaggagaaataaaacaaagagataatccatgagaa
gaacaatatactaagtccccttaatgacccccattggagtgatgtggttg
gcttgatactgatgttcaatagacaccctccccctcccatcttcagtcgtc
tttagctctaaaatctctgtggtcgaacttttgagatagcgtgatgtgcc
accacatatgccatgacccaagggactggctggcaattactctggatgct
tcttgaaggttctcattgttcttgccctaacctgcctctgtaggatct
caacttttctcttcccgctccagctgcactatgtatccgtgcttggctct
cagttgttggattctcatgtctccttttcacagtggctcaggtaagggg
acttgttgcaacatctcgagatgctgtctttagtcctagctctcttggaa
gagaggaaggagatgagacatactgaaaccacattttcttgatgttgag
cagaatccagttcacagactagaaaatgttttattccttgtaggctcagc
agtacagaaacaaggtggggaaaggaaaaacaatttctaaagagtgaatta
ttatgaattatcttataaatgcccatgccacctgctttacttctcataat
tcactaaacctcctttacttctcataattcactaaattcactatgctctg
catttcatctgtggtgtgatgagttaaaattgccttgtgggaatttttt
cagaacatttgtccacttgaacaaaaatcaatattctgtctcttaaacag |

| Illustrative Sequences-All sequences are shown 5' to 3' |
|---|
| aagcatttgaacaagttgcactatgcggaggtgagaacaataattatatt
ggtacatgtcttaaaaattacccagaagcagatgagaatttgtgaataaa
tgactcattaagaaagtgtccccagaagaagtcagtaagtgagtgggggc
atgaggagaggaaaagggaagtcaagcaaagtgtgctattttttggccaag
tcttatagtagggagctttggcctaaatctacaagggaaacttagagcat
aaattgagttgtctgccataaatcaactgggaggaacttaggttttcata
cacttgcattatcagtcatagctaagaacacccaagggccatgtaaactc
ccaattacttctctcacagccatagggtaatcctctaaaaacagacaaat
ggacaggccattggaaataagagtcctggacctaggaagaaattcaggaa
acagtaaaggaattcagggaaacctaggtgggtcactgcagtgactacta
catcattttaagcattattgagcgtttggtggtgcctagaaagctgtgt
gtgtgtgagtgtgtgtagaaagctatttagttctcacaataccccttagaa
ttatctctgttttacatactaaggaactaaagtgttcagtaatttggaag
agtgtttaaaaaaaggtctgcaatagagccaagattcaaatcctggtctg
tctgaaggccatgtccacagtcagttattctctccttattatactacct
cctggtcagcctcctaaccaaagtaagaggtgaagtgcagaaaggatagg
agaacttgggatagggtaaacagaagaaaaaaaaaagcagagatgataaa
atagtttgtaactaagaaatgttatagcaaatgagtgggggattattctat
ggccaagagaagggaagactgaggaaacttactaatgatcttcaagttca
tgaaagggttttaacacagaatagattggccagctgtgctcaaatttctac
atagtgaatttaaaaagaaaactatttgctgttatagcacgaggatttta
ggctggattgaagaaagtgttctctgggcaaaagggctattgagcactag
agtgaaatcctataaactcaaattagaaagaaaaaagcagaaaagaaa
agagaaaaatataaagaaaaagaaaagaatgtgagcacagtctgtcat
gctgtgcaaatgtatgagatgttaccttgaacacagctgcttcacacctg
caaccttccacagagggagagccgtgaattaaaaaatataaagcagcgaac
ttcattgtagctgaggatgccaggaaacctgatggccttctagaaactat
catattaattgttgtattagggcagaaacatgtactggtctggtttagta
gtttgcttcttaatgcgaactctctttttcacttttgtcctttctccccc
aaagacaaacatttccaagacattatgtatatgtaaaagagcattttatg
tagaagtacaagagaaataacatttggtgatgcaacaatgtggcacagatc
aatgactgtttagatagcaaacggagtggactttgacggtaccttgtgaa
gtggcacatatcattgaataatctattgttttgatgtcctctatgcaccc
ataagcctgccctgaaaattttctgcataaccaatttagatttatgta
tatatatatacacacacatatatacacacatatctctatatatataca
cacatacatatagatatatatacataaacactctcaatgatgtgttgaga
tggtatgtactgcagccagactttaaactagctcattattttataatggg
gtgtatactaaaaatttatttttgaagtcacttacaaatgtgttttccca
tcaacattctgctgtagatgtcattatttgggggcagaatatcactgtaa
tcacaccaaatttacctgtgaagttactatttccagctacactgtagac
taaattaatagttctgagttactgagaaactcgatcaccagtcactat
ttctctggaaaaaaatgaattccattttgaatttggaactccagaaatat
ttccatcctaatgtgcctctcagtagaggtttgtcagaggtttccaca
cattgggtaaagccaattgtcaaaagtcaaatgttccctgaaatgtgcttt
tccttaaccagagtggtgacttgtgctctgtgaaagagaattttccttc
cttccatttaatagcaggctttcataggattgaagaatttgtacaagag
caacaattattattagcacctactatgtattggacactatattattcatt
gtatatatatctttatgtagcctccataacaaccttgggatgttatat
tattatcaccattctacagaagaggaaatagatgtaaagaagtcagcttg
ctggaagtcctataaataaatgatagaattgggttgtgctgtggtttt
gaatgtctcctcccaaattaatgttaaaatttaattgccattgtaacagt
attaagggtaggactggtaagaggtagattaggccatgagagctgccctc
ctcatgaatggattaatccagctttcacaggagtgagatcattataaaag
gccaaatttggtcctctttgtcgcttgccctctcttgccccttctgccttc
caccatgggataatgccacaagaaggccctaatcagatgccagctcctca
atcttggacttagcctatggaactgtgataaatattttttctcttttagaa
attactcagatactggtattttgttatagcagcacaaaacaatctaagac
aggttgtgaactctggactgactgaccctaaattcaagagccttttcatg
gatgttgtggtggacgtttgttggttgtgtgcctgacatccattctccct
taccattattttcctttggaaaattttaccttcactacctgtccccata
ccacaccacatcacagacattagttttgtatggaatgtgaccccactgcct
gtcttaggagtgagcccagattgacttaggccaaccactatattatattc
ctctccctcatttcccctcccatactgcctggctcagagataagtaggt
agctcaatcagagccaatgagatagaaggagatattccttgtcaccttg
gaaggagaagctccctcttttaactgtgttgcaaaagaatgtgagttctg
aagtggtggaaacattttttttacctataggagacagcgctgtttctgggt
ggcaaccactgtgtagagccttagttgaagcactggggcagaagacag
agggaatccagggtcaaaacaacaacttttggactcctgggtcaaccctt
atctgaagtaagagcggcttctgggctcaattgtaaacatatttgctcaa
acaacaacttgtagtttgagccacgttatggggttcgtgtcaatttcaac
ataaaggttgtaagtaacacaggactccccaggactattccttcatta
aaaacatttacatcttccaaatctctggtatgatgagacttgacttccac
aatcacactcctgaaacaattcagcaacctaattaatcaaataagattac
attcaggctattctccttgctaagtgaaaaaacttgcccacttaaaattt
acgaagattctgagcaatacagaataaaaaacaaagaatgtttggttaat
gattttaaggtaggcagaaaaaaaactaattaaacgatgcctttttctgat | aattctagttaattggagttttaattccagtaggaataataaaaactggg
gtctaagttttggtaagtaaagttttcaaattatttatatttgcttaattt
agaaaaatgtatgtacacattcatttccctgtgagacattaaaatatatg
aacatagattaagcaaaatatattttcctttattgtgataattccttgtt
atctccagtctttcccccaaatgtgataagaatacatagctacagaggga
ggagccaagatggccgaataggaacagctccagtctacagctcccagcct
gagggacgcagaagatgggtgatttctgcatttccatctgaggtaccggg
ttcatctcactagggagtgacagacagtgggcgcaggtcagtgggtgcgc
acactgtgctcgagccgaagcagggtgaggcattgcctcactcgagaagc
gcaagggtcagggagttccctttcctaatcaaagaaggggtgacggat
ggcacctggaaaatcgggtcactcccaccggaatactgcgcttttccgat
gggcttaaaaaacggcgcatcacaagattatatccctcacctggcttgga
gggtcctaccccacggagtctcgctgattgctagcacagcagtctgagat
caaactgcaaggtggcagcgaggctggggagagggcgcctgccattgccc
aggctgcttaggtaaacaaagcagcgggaaagctcgaactgggtgagc
ccaccacagctcaaggaggcctgcctgcctctgtaggctccacctctggg
ggcagggcacagacaaacaaaaagacagcagtaacctctgcagacttaaa
tgtccctgtctgacagctttcaaaagagcaggggttctcccagtaggcag
ctggagatctgaagatgggcagactgcctcctcaagtgggtccctgaccc
ctgacccccgagcagcctaactgggaggcaccctccagcagggggcacact
gacatctcacactgcagggtactccaacagacctgcagctgagggtcctg
tctgttagaaggaaaactaacaaacagaaaggacatccacaccaaaaacc
catctgtacatcaccatcatcaaagaccaaaagtagataaaaccaaagg
atgggaaaaaacagaacagaaaactgaactctaaaaagcagagcac
ctctcctcctccaaaggaacacagctcctccaccagcaacagaacaaagct
ggacagagaatgactttgacgagctgagagaagaaggcttcagacgatca
aattactctgagctacaggaggacattcaaaccaaaggcaaagaagttga
aaactttgaaaaaaatttagaagaatgtataactagaataaccaatacag
agaagtgcttaaaggagctgatggagctgaaaaccaaggctcgagaacta
cgtgaagaatgcagaagcctcaggagccgatgcgatcaactggaagaaaa
ggtatcagcgatggagatgaaatgaatgaaatgaaacggaagggaaagt
ttagagaaaaagaaataaaagaacgagcaaagcctccaagaaatatgg
gactatgtgaaaagaccaaatctacgtctgattggtgtacctgaaagtgg
tgggagaatggaaccaagttggaaaacactctgcaggatattatccagg
agaaatttccccaatctagcaaggcaggccaacgttcagattcaggaaata
cagagaacgccacaaagatactcctcgagaaggagcaactccaagacacat
aatcgtcagattcaccaaagttgaaatgaaggaaaaaatgttaaggcag
ccagagagaaaaggtcgggttacctcaaagggaagcccatcagactaaca
gcggatctctcggcagaaaccctacaagccagaagagagtggggaccaat
attcaacattctaaagaaaagaattttcaacccagaattttcatatccag
ccaaactaagcttcataagtgaaggaaaataaaatactttacagacaag
caaatgctgagagattttgtcaccaccaggcctgccctagaagagctcct
gaaggaagcgctaaacatggaaaggaacaaccggtacgagccgctgcaaa
atcatgccaaaatgtaaagccatcgagactaggaagaaactgcatcaac
taacgagcaaaatcaccagctaacatcatcatgacaggatcaaattcaca
cataacactattaactttaaatgtaaatggactaaatgctccaattaaaa
gacacagactggcaaattggataaagagtcaagacccatcagtgtgctgt
attcaggaaacccatctcacgtgcagacacacatagcctcaaaataaa
gggatggaggaagtctaccaagcaaatggaaaacaaaaaaaggcagggg
ttgcaatcctagtctctgataaaacagactttaaaccaacaaagatcaaa
agagacaaagaaggccattacataatggtaaagggatcaattcaacaaga
agagctaactatcctaaatatatatgcacccaatacaggagcacccagat
tcataaagcaagtcctgagtgacctacaaagagacttagactcccacaca
ttaataatgggagactttaacaccccactgtcaacattagacagatcaac
gagacagaaagtcaacaaggatacccaggaattgaactcagctctgcacc
aagcggacctaatagacatctacagaactctccaccccaaatcaacagaa
tatacatttttttcagcaccacaccacacctattccaaaattgaccacat
acttggaagtaaagctctcctcagcaaatgtaaaagaacagaaattataa
aaactatctctcagaccacagtgcagtcaaactagaactcaggattaag
aatctcactcaaaaccgcttcaactacatggaaactgaaaaacctgctcct
gaatgactactgggtacataacgaaatgaaggcagaaataagatggttct
ttgaaaccaacgagaacaaagacacaacataccagaatctctgggacgca
ttcaaagcagtgtgtagagggaaatttatagcactaaatgcccacaagag
aaagcaggaaagatccaaaattgacaccctaacatcacaattaaaagaac
tagaagcagaagagcaaacacattcaaaagctagcagaaggcaagaaata
actaaaatcagagcagaactgaaggaaatagacacacaaaaaccccttca
aaaaattaatgaatccaggagctggtttttttgaaaggatcaacaaaatt
gatagaccgccagcaagactaataaagaaaaaaagagagaagaatcaaat
agactcaataaaaatgataaaggggatatcaccaccgatcccacagaaa
tacaaactaccatcagagaatactacaaacacctctacgcaaataaacta
gaaaatgagaagaaatggtaaattccttgacacatagaaacactctcccaag
actaaacaggaagaagttgaatctctgaatagaccaataacaggatctg
aaactgtggcaataatcaatagcttaccaaccaaaaagagtccaggacca
gatggattcacagccgaattctaccagaggtacaaggaggagctggtacc
attccttctgaaactattccaatcaatagaaaaagagggaatcctcccta
actcattttatgaggccagcatcattctgataccaaagccgggcagagac |

| Illustrative Sequences-All sequences are shown 5' to 3' |
|---|
| acaaccaaaaagagaattttagaccaatatccttgatgaacattgatgc
aaaaatcctcaataaaatactggcaaaccgaatccagcaccatatcaaaa
agcttatccaccatgatcaagtgggcttcatccctgggatgcaaggctgg
ttcaatatacacaaatcaataaacgtaatccagcatataaacagagccaa
agacaaaaaccatatgattatctcaatagacgcagaaaaggcctttgaca
aaattcaacaactcttcatgctaaaaactctcaataaattaggtattgat
gggacatatttcaaaataataagagctatctatgacaaacccacagccag
tatcatactgaatgggcaaaaactggaagcattccctttgaaaacgggca
gaaggcagggatgccctctctcaccactcctattcaacatagtgttggaa
gttctggccagggcaattagggaggagaaggaaataaagggtattcaatt
aggaaaagaggaagtcaaattgtccctgttttttagatgacatgattgtat
atctagaaaaccccattgtctcagcccaaaatctccttaagctgataagc
aacttcagggggtgatcagccagccacctggtggcaggttgattatattgt
acttcttccattatggaaagtgcagaagtttgtccttactggaatataca
cttactccagatataagtttgcctatcctgcatgcagtgcttctgccaag
actaccatctgtggactcacgtaatgccttatcaagtgtcatgtgattcc
acacagcgttgcctctgaccaaggcactcactttacggctaaagaagtgt
gtcagtaggctcatgctcatggaattcgctggtcttcccatgttccacat
catcctgaagaagacggattgatagaatgttagaataagcttttgaagtc
acagttacaatgccaactaggcgacgatacttgcagggctggcgcaaag
ttctccagaaggctgtatatgctctgaatcagcgtccagtgtatggtact
ctttctcccatagccaggattcgcaagtccaggaatcgaggggtggaagt
ggaagtggcacctcttgatcatcaccattcactgtcaccctcacgtctac
actacaacagttttgcttcctgtccccacaacattgcattctgctggcc
tagaggtcttagttccagagggaggaacactgccaccaggagacacaaca
gttccattaaactggaagttagtattgccacctggagactttgggttcct
cctaccttaagtcaacaggctaagaaaggagttacagtgttggctgggg
tgatttacctggactatcaagatgaaatcattctactattccacaatgga
ggcaaggaagagtatgcatggaacacaggagaccattagggcgtctctt
agtattaccatgcctgtgattaaagtcaatgggaaactcaacagcccaa
tccaggcaggactacagatggcccagactcttcaggaatgaagatttggg
tcacaccaccaggaaaaaaaccatgaactattgaggtgcttgctgaaggc
aaagagaatacagaatgggtagtagaaaaggtagtcatcaacaccagct
acgactacgtgaccagttgcagaaatgaggagtgtaattgtcatgaatat
ttcctcttgattttgttaaaatgatgtttatgcatgtacacacttgtact
aagaaaaatcttcattttcttttcctttattatgtgacataagattat
tgacttcctatcagcatttaagtattgttaactttaggtaatagtatctg
ggttgaggattggtcatttctggttttatgaaggatagttctatgaagg
atagttgtattatcttaagcataattatgacctattaatgtgtttatttg
aagagtatgtatgatctcaggagatgtgtgtgggtacaagctgacaaaag
gtggacttgtgatggttaatactgagtgtcaacttgattggattgaagga
tgcaaagtattgatcctgggtgtctgtgagggtgttgtcaaaggagatta
acatttgagtcagtgaactgggaaaggcagacccactcttaacctgggtg
ggcaccatctaatcagcttccagcgaatataaagcaggctgacgaaaacgtg
aaaaggctagatggcccagcctcccagcctttctcctgtgctggatgctt
cctgacctcgaacgtcggactccaggttcttcagttttggaactcagact
ggcttttcttgttcctcagcctgcaaatggcctattgtggtaccctgtga
ttgtgtgagttaatacctaataaactcccctttaagtgtatcaatgagt
tctgtccctctagagaaccctgggtaacacaggatgttacagataaattt
gctatgaatatttgtgtacaaatctttatattgacagatactttaattttt
cttggggaaatacttggaagtaggttgcatggattatatgcatgtgtgt
gtttgcttttttaagaaactatcaaatggttttccaaagtagttgaatca
ttttacattctatcatcagtgtatgagagttttcagttgctcaaaattct
tgctaaaaccagatgcggtgtattttttttaaattagccattctaatag
gtctataatgttatctcattgtgattttaacttaatggtgttgagaatct
tttcaggtttatttgccatctatatgtttctttggtgaagtgtcgttc
aaatcttttgtccattgttttcttattattgaattttaagaattttaaat
atatatatataaatatattttggatataagtcttaaatcagatatgtggt
ttgcaaatatttctcccaagtatctggtttgtcttttcattttgctagc
agtgtgtttcaaaaaatagaagtttttaaaattatgataatgtccaattta
tctatattttattttacagattgtgattttggtatcatatctaaggaatc
tttacctaatcaaagttgcagaagttttctcctaaaagttttataggttt
aagttttacatttaggtctatgattcatgttgagttaatttttatggtgca
agatatagatcaaagtttattttttttttcttgcatatatatatatatcca
attattccagcaccatttgttgaaaagactaatctttctctactgaattg
cctttgaaactttgtcaaaatcatttgtctgtatatgtgtgggtctattt
ctggactctcttctgttccatttgtctatttgtctctatcttttacaccagta
ccaaactgtcttgattattgtagctttcataataagtgttagttctctcaaa
tttgttcatcttttttttttcagagttgttttggctattctgggtcctttg
aattttttatatcaattttagaatcagttaatttctacaaaaaaccctgct
agaattttaactgatttggtttaaatgtatggatttggtttgggaagagt
ggctttcttagcattattgagtctttttgactaatgaacacaatataggta
gaacatcactaatctgaaaatctgaaattttgaaatgctctaaaatctgaa
acttttttcggtaatgacatgatgccacaagtggaaaattacacatctgac
acctttgcttcttatagttcaatatatacaaactttgtttttctgaacaa
aagtataaaaaattttgtgtaaaattacctttaggctgtgtacataaggt | gtatataaaacaaatgcatttgtctttagacttgggtcccattcccaag
atatctcattatgcatatgcaaatattccaaatccaaaaaaatttacaat
ccaaaacacttcttgtcccaagcattttggatgaggaatacacaacctgt
atatctcaccatttattcggtgatcttaaattactttcagcaatgtttt
atagttattcagtgcacaggctcttacatcttttgacactttattttt
aattatttcatattttgaggccattttaatggcattgttttcaaaata
ttaacttctgatggttcattgctaatatataaatgagtcattttat
atattgatcttttatcctgcaacattgcttcaactcatttaataattcta
gtagcttatttcaaaaatatagattccagtggattttctacatgaataat
tatgtcattttgtgaataaagagttttgtttatttcttttcaatctggata
cctttttatttctttttcttgctttattgcattgacaagaaatccaatat
aatgtgaaagaagaagtggtgagagtggatatcttgctttgttcctgatct
tagctattccttattttttttaagctatattttcatagaagcccttcatc
aagttgagaaagttcctttttaaggcagtaaaattcctttttaaagca
aataaagaatgtatatttgatatttgtcaaatactttcttctacatctatt
gagatgatcatatagttaatacatttcttttgtttcttttattattatgga
gtacattaattgatttttgttgttaaaccaaccttgcacacttggtcat
gatgtattatcctttaacctggtgttggatttaatttgctcaaattttcag
taacaactttttcaacaatgatcgtgagggatgttggcctgcagttttct
tttcttgtaatatctctatctgttttggacattttaattctgggcttatag
aatgagttgaagaatgtcctctccttttcaatttttgtgcaataatttgtg
tagaatggacactgtttcttccttgaatctttggtaggattatcaagtga
agccacctggacctccgcattctctttgtgggaaattgtataactattgat
ttaatttctttaatagtggagggctatttatattacctaatttttttcttt
gagttagctttggtagtttgtatcttcaaagaattttgtccattgtatct
aagttgtagagtttattcaaataaggttgtatataatattcccttagtgt
cattttgatatttgtaaaatttgccctggttcacttctttcatgcctac
tactgacaatttgtatcttccttcttttttctctgaccagtctggctaggg
atttattaattcatcaattttctcaatttctcaagactgacatattat
tttgcttttgtatgtctcaaaagtctttattttgctatcattttttgaaat
acttttttcagtgggtataggaattctagaaatagtttttccctcccaat
acttttaaagatattgccctactgtttttttacttttgcattgtttgtaaca
gaaatttactgttacccttatttctgtttctgtatacatatctttttcctt
ctactgcttataagatttcctatttatcacccattttgatacattttatt
attctgtgccttagtattcttctctttttatgtttctttttgcttagggtttg
ctaagcttcttatatatatgtgggtttgtcattttatcaagttttggaaaat
tttcatccataatatcttcaaatattttccctccattatgacttcaatta
ctcatgtattaggctgtttgagttgtcccacacctaacactctgtccagt
ttttaacagttatgtttttctatgttttcattttgggttgcttctatttcca
tgccttcaagttcactaatcttttcttcctcaatgtctaatctgctgtta
attctagaaagtatattttttcatcttatacatttttagttttttaatcattaa
aagtttggtttggatcttttttatgcttttcatgttttttacttaacttttt
gaacatatggaatacaattataataaccattttaatatccttctctgcta
actctaacatctgtggttagttcttaatcagattcaattgatttgatttat
ctcctcattatatatcatattttcctgtttcttttgtatgtctgaaatt
tttgtttgaatgccagacattgtaaattatgccttgtgggatgctatata
ttttttgtgttcctataaatattcttgagctttattataggacacagttaa
gttacttggaaacagtttgatcttttctacccttgttttttaggcattgct
aggtagaccagagtagtgttagtcatgggttaattattcattactactga
atcaagacccttcagaataccatactcaatgccacataaatcttgaggtt
ttccagtcttcctggtggatggcaggcactattctcccccagtgagtgctc
actaggtacattttgggtggtcctttctctggtcgtaggtagtatcttta
catgaatgcattacccatactcagaatgagggacattttgtagaaatct
gaagttctctctctgcacagctctttcttttctggtaatctgttctgtga
actcaagctgttttggtctcctcagaccctccatttcatttcctcagctc
atagagtcttctacactccacctgggttccctccctgtctctggcctg
gaaactcccttaaggtagtaaggtagaggaatcacagagtccacatcct
tgtttcacatatctgagggctcagtatcctgcattgcctggtgactcagt
gtcttaaaaactattgttcatatattttgtttattttttgttgtttcag
GTGGAAGAGTAAACTGTTCCTGTTTCTCCATCTTGACAGGAAGCAGAAGT
TCTCCTTAGCTGATTTTTCTTCTTGCCTTATACTGGGTTCTTTAACACCA
GAACAAAAATAAATAAAAGAATCTTCCAGAAATTCATGAAGAGACT
TCAGgtatgcagcataggtgtttgacaactacgtagagcagtgggccagt
cttaatttgtttcattaatctggtaaaaaagaaggatttgcatgaaatt
cgcaattcagattgccatattagccactaagtcagaagacttgagagctg
agccttggagaaacaaaatccttgacagttgttgatgttttttgtaatagg
agacttctattattttagcaaacagaaagactacataaaaatgtcagaaa
gaaactactttggagaaaaaaataggaactgactcactaaagggaccta
ttggggataattacccagagcctgtggtagatcaggatggctgatttaaa
gttattgttttgcaaattctgcaaaaaacaaaaaaacaaacaaagattt
tttttttcttggctttagcaatagtggaaaatttcttccacagctgtaat
ctcatgtaaactgccaaagtggatttttattctctgagttttctcaagcctc
cttttctctaatcagagtaatattggctaatgataaaacagtacaaact
ataatttgaaatagtgtttcaattttcaatttgcagtctgggaatagatc
acaagaattttagtttgttggtttcctgctgccgtagGTCAGGAAAGCCT
GAACTTTCTCATCCAACACCCGTTCAAGTCGGAGGATGCTGATTAATTCA |

| Illustrative Sequences-All sequences are shown 5' to 3' |
|---|
| TGATGGAAAGGTATCAATTTCACAGCCCAGACCTCTACATTCTTGAAATG
CTCTTCTCATGGGAGACATTAAATAAGCTTTGAATTAACTgtaagtaaat
aaatattcaattatttgaatagcactatattctgtttcattaaaaatatt
tcttacttgattttctcaccaataaaagtattcaaaaatgtttaattca
atcatcatcacatcaagaattacgatatatctccgaattatataagtga
ttttctggtcatgcacataccagttgttcttactctatataaatgtactt
ttttgttaaaatataatcatttagtttaaaattgagatatccttgttact
ggagaatttcaaatatatttaacaacaacaataaaaagcttaaatataaa
tagcaaatgtgagtaagcatgggataattgaatggcttttatattttg
gaagtcaattccatcttcatagattaattcttccaggttttaattcacat
tgagttctaatggctgacaccattttcctcctctgtatcttcttcagaa
tatggacatcttggttgttgtgagaatggagttaccaaagttataatca
gttaaacactaagcaaagtgttatggcaaagtgtagtcaagtgcatttcc
tgtcagatggtcaacacccttaagtgcttgaggttgaagagaattgttttc
atctctgttgataggaagaaccaatgatgtgatcctggatactggcaat
tgttgcccaagaaaacctctcccccttgctgtgggactgctgggcacccaa
ataatgcacccaaataatttgatagctcttgttacacagctcttcttgga
ctaaaaggccctcagcattcctgtcaatttctacactcctgaagcttcat
ctggtaattccctgactatgcagtaccaccccactcctagagtgtcttt
agaggtgtttgcttcttcttaaagtctattatcctcttgttcttcgaggg
cttattcttaggggacttggagggcttattaagccctaagactcaatcat
tagcaaccaaaaaattaacttctactctcccaaggtcagggacagcataa
tcttaaaatacagtggttagggaaaatatttgcataacgtattttaaaga
atgcacaggaagggaaggcaaatatagaggaggaagatgattttaagagag
tagagcagaaaatatacagctgccacaaaaatttagaattgcagaaccag
ctaaaggtaggtgtttgttctgcttactaataaaagcatacaccaaataca
attatttggaagcctataattttttagggtaaaattttttaggtgttctt
ctagtcttaccccattatttttaaagatgtaaaaactggatcccaaagagg
agaaatgacttggttaagctcacacagaaactagaatcctcatcctttg
tattgtatcaaatgcttttatgattaccatatgctgccttttttaaggcct
gtgatctccagagagagatttcagcttttttgatatgccaaactaaggaat
tcttagttggccttttttttcttcttgagtttgtgcttgcttaacctaat
gagtaggtaataaccctgtgtttccgaatttcttaaatcagacttttgg
gggatgaaattttgttaatgattctgttaagaaataatgtcttttacact
ttctcagctgaaaggcaaggggatgcaggatggaggttagaaatacacag
ctgccatagtctaattcttatatagatattattgagtgattaaatgatca
agaaaactgcctactgcttctcttttacttttctgtatttagcaggaacat
gaccttttctttttgatccataatgagagagatgaagagaatatgagaga
atatatgagaaatgaaagtgtgctaagaatccacataattaaacacccaa
acacttagttatcattcaagatccttcatgatcttgccaatctatttc |
| ccaactatatcccatattatctccctttgcatacagtttaatccatacac
taaataacttgctattcttttaaatgctttgttttttctacctctgcctcta
ttttcatactgctttctctacctgacattctctgtcccaaactgttgct
attcaaatttgacttagcttgggttacctgagatatagacactgagacaa
gcttttaaggttgagtaatttgttagagagtaaaggtaggagaatgatta
agtgaaagaatgaaagaaagtttattttggaagagcatgttatcaagaca
gctttcagttccaggaagcaactgaagcataatcccacagggaaagctct
tgaagcccagacaagctattctgccttaaagttatcctacccaaggggta
agggagctaagtatttatacaccaacactcttcagatattgcttgagagc
tgctcctagagacattaattccagaagcttccaacctgttgaacaggtgg
cagagtgagtttcagcagtgagaggacacccttaacaaagaactactggt
gctaggagttggaagttgggccaaagggaaacagatgctaacagggaggt
aatatgagaggcactgacagcatctgctacaaaactgtcccaaaagaaa
agatgggatacagctggttatgctgcagttaaaaagcaaccaagtattaa
tggcttaataccacaaaagttattttttcacttcttgttatcagGAGACC
TCTGTGGATTCTATAACTCAAAGACCCAGGCTGACGGCTGGTGAATAGC
TACCATCTCAAACATGGCGTGATGCTGCATCAGAGAGAAAAATAAGCTCT
TGCATTGACAATGAAATGTCTACCCTGT |

SEQ ID NO: 5 SATB1 1d variant >DB126439 (Human EST)
Normal text is exon 1
Bold text is exon 2
Underlined sequences are primer sites for detection of this transcript
ATG in italics indicates the translation start site in exon 2
CTCCTTCTCTTCCTTCCCTTGGCCCCGCGCGCTCGCTCGCTCCTCG
CCTCGCTCTCCCCTTTAAACGCCCACTTCGTATGGGAAAGAGGACAACT
TGAAGTCAAGTTGCAATTAACTTCCGCGGCAGCCGCAGCTCCGGCGGCGG
CGGCGGCGGCAGGAGAGGCAGAAGCCGCCGCCTCGGAAGTCCGACGCCGG
CGCGCCCGCCCGGGGAGCCGTTCTTGGTTTCAGGCCCGCACTCGACAGCC
ACCGCCGCCCCAACGTCCATGCCTGA**GTGATCTTTAGACAGTGACTGAG
TA*T*GGATCATTTGAACGAGGCAACTCAGGGGAAAGAACATTCAGAAAT**GT
CTAACAATGTGAGTGATCCGAAGGGTCCACCAGCCAAGATTGCCCGCCTG
GAGCAGAACGGGAGCCCGCTAGGAAGAGGAAGGCTTGGGAGTACAGGTGC
AAAAATGCAGGGAGTGCCTTTAAAACACTCGGGCCATCGTGATGAAACCA
ACCTTAGGAAAGGAACCATGCTGCCAGTTTTCTGTGTGGTGGAACATTAT
GAAAACGCCATTGAATATGATTG**

What is claimed is:

1. A method for treating a cancer in a human patient, the method comprising:
   determining, in a sample from primary tumor tissue from the human patient, a level of SEQ ID NO:2 transcripts that is at least 10-fold greater, when normalized, compared to the level in control normal tissue, by:
   obtaining or having obtained a nucleic acid sample comprising RNA from a primary tumor;
   detecting or having detected a level of SEQ ID NO:2 transcripts that is at least 10-fold greater in comparison to the level in control normal tissue, wherein the transcripts are the RNA version of SEQ ID NO:2; and
   administering a chemotherapy or immunotherapy agent to the human patient determined to have a level of SEQ ID NO: 2 transcripts that is at least 10-fold greater, when normalized, compared to the level in control normal tissue.

2. The method of claim 1, wherein the detecting step comprises performing a quantitative PCR reaction.

3. The method of claim 1 wherein the detecting step comprises performing an in situ hybridization reaction.

4. The method of claim 1, further comprising detecting the level of a SATB1 exon 1d transcript in the primary tumor sample.

5. The method of claim 4, wherein the step of detecting the level of the SATB1 exon 1d transcript comprises performing a quantitative PCR reaction or performing an in situ hybridization reaction.

6. The method of claim 1, wherein the cancer is breast cancer, pancreatic cancer, colon cancer, or prostate cancer.

7. A method of detecting the level of expression of an RNA version of the SAILOR sequence SEQ ID NO: 2 in a human tissue sample, wherein the method comprises performing a quantitative reverse transcriptase-PCR (RT-PCR) on RNA obtained from the human tissue sample using amplification oligonucleotides that amplify a fragment comprising at least 700 contiguous nucleotides of SEQ ID NO: 2.

8. A method of detecting the level of expression of an RNA version of the SAILOR sequence SEQ ID NO: 2 in a human tissue sample, wherein the method comprises performing a quantitative reverse transcriptase-PCR (RT-PCR) on RNA obtained from the human tissue sample using amplification oligonucleotides that amplify a fragment comprising at least 600 contiguous nucleotides of SEQ ID NO: 2, wherein the human tissue sample is from a breast cancer, pancreatic cancer, colon cancer, or prostate cancer.

9. The method of claim 7, wherein the human tissue sample is a blood sample.

10. A method of detecting the level of expression of an RNA version of the SAILOR sequence SEQ ID NO:2 in exosomes from a blood sample from a human patient that has cancer, wherein the method comprises (i) performing reverse transcription on RNA from exosomes obtained from the blood sample and quantifying the amount of the RNA version of SAILOR sequence SEQ ID NO:2 in an amplification reaction using amplification oligonucleotides that amplify a fragment comprising at least 35 contiguous nucleotides of SEQ ID NO:2; or (ii) sequencing cDNA transcribed from RNA from exosomes from the blood sample in a sequencing reaction or directly sequencing RNA from exosomes from the blood sample in a sequencing reaction; and quantifying the level of RNA fragments that comprise at least 35 contiguous nucleotides of SEQ ID NO:2.

11. The method of claim 10, wherein the method of (i) comprises performing quantitative RT-PCR.

12. The method of claim 10, further comprising detecting the presence of a SATB1 transcript in the exosome sample.

13. The method of claim 10, wherein the cancer is breast cancer, pancreatic cancer, colon cancer, or prostate cancer.

* * * * *